(12) United States Patent
Paralikar et al.

(10) Patent No.: US 10,971,943 B2
(45) Date of Patent: *Apr. 6, 2021

(54) MEDICAL DEVICE TEMPERATURE ESTIMATION

(71) Applicant: Medtronic, Inc., Minneapolis, MN (US)

(72) Inventors: Kunal Paralikar, Minneapolis, MN (US); Elizabeth A. Fehrmann, Falcon Heights, MN (US); Venkat R. Gaddam, Plymouth, MN (US); Boysie Morgan, Minneapolis, MN (US); David P. Olson, Minnetrista, MN (US); Jadin C. Jackson, Roseville, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/723,372

(22) Filed: Dec. 20, 2019

(65) Prior Publication Data

US 2020/0136417 A1 Apr. 30, 2020

Related U.S. Application Data

(63) Continuation of application No. 15/843,854, filed on Dec. 15, 2017, now Pat. No. 10,554,069.

(51) Int. Cl.
*H02J 7/00* (2006.01)
*H02J 50/10* (2016.01)
(Continued)

(52) U.S. Cl.
CPC ........ *H02J 7/007192* (2020.01); *A61B 5/686* (2013.01); *A61M 25/00* (2013.01);
(Continued)

(58) Field of Classification Search
CPC ........... H02J 7/007192; H02J 7/007188; H02J 50/10; H02J 7/0063; H02J 2007/0067;
(Continued)

(56) References Cited

U.S. PATENT DOCUMENTS

| 6,431,748 B1 * | 8/2002 | Baratta | G01N 25/18 374/45 |
| 6,681,135 B1 * | 1/2004 | Davis | A61N 1/3655 607/21 |

(Continued)

FOREIGN PATENT DOCUMENTS

| WO | 2013158238 A2 | 10/2013 |
| WO | 2016172530 A1 | 10/2016 |

OTHER PUBLICATIONS

Prosecution History from U.S. Pat. No. 10,554,069, dated May 1, 2019 through Sep. 17, 2019, 34 pp.

(Continued)

*Primary Examiner* — M Baye Diao
(74) *Attorney, Agent, or Firm* — Shumaker & Sieffert, P.A.

(57) ABSTRACT

Devices, systems, and techniques for monitoring the temperature of a device used to charge a rechargeable power source are disclosed. Implantable medical devices may include a rechargeable power source that can be transcutaneously charged. The temperature of an external charging device and/or an implantable medical device may be monitored to control the temperature exposure to patient tissue during a charging session used to recharge the rechargeable power source. In one example, a temperature sensor may sense a temperature of an internal portion of a device, wherein the housing of the device is not directly thermally coupled to the temperature sensor. A temperature for the housing of the device may then be estimated based on the sensed temperature provided by the non-thermally coupled (Continued)

temperature sensor. A processor may then control charging of the rechargeable power source based on the determined temperature for the housing.

24 Claims, 12 Drawing Sheets

(51) Int. Cl.
*A61B 5/00* (2006.01)
*A61N 1/378* (2006.01)
*G01K 7/00* (2006.01)
*G01K 13/00* (2006.01)
*A61N 1/372* (2006.01)
*A61M 25/00* (2006.01)
*A61N 1/36* (2006.01)

(52) U.S. Cl.
CPC ............. *A61N 1/3787* (2013.01); *G01K 7/00* (2013.01); *G01K 13/00* (2013.01); *H02J 7/007188* (2020.01); *H02J 50/10* (2016.02); *A61B 2560/0219* (2013.01); *A61M 2205/3368* (2013.01); *A61M 2205/3538* (2013.01); *A61M 2205/8243* (2013.01); *A61N 1/36007* (2013.01); *A61N 1/36062* (2017.08); *A61N 1/36071* (2013.01); *A61N 1/37223* (2013.01)

(58) Field of Classification Search
CPC ........ H02J 7/0072; H02J 7/0091; H02J 7/042; H02J 7/087; H02J 2007/10; H02J 7/125; H02J 7/007194; A61B 5/686; A61B 2560/0219; A61M 25/00; A61M 2205/3368; A61M 2205/3538; A61M 2205/8243; A61N 1/3787; A61N 1/36062; A61N 1/37223; A61N 1/36071; A61N 1/36007; G01K 7/00; G01K 13/00
USPC ........................................................ 320/137
See application file for complete search history.

(56) References Cited

U.S. PATENT DOCUMENTS

| | | | |
|---|---|---|---|
| 7,952,322 B2 | 5/2011 | Partovi et al. | |
| 8,244,367 B2 | 8/2012 | Wahlstrand et al. | |
| 8,335,569 B2* | 12/2012 | Aghassian | A61N 1/37223 607/60 |
| 8,496,646 B2* | 7/2013 | Kamen | A61M 5/1413 604/890.1 |
| 8,554,322 B2* | 10/2013 | Olson | H02J 50/12 607/33 |
| 8,784,364 B2* | 7/2014 | Kamen | A61M 5/142 604/65 |
| 8,901,878 B2 | 12/2014 | Prutchi et al. | |
| 9,176,163 B2* | 11/2015 | Heath | G01P 5/10 |
| 9,209,634 B2 | 12/2015 | Cottrill et al. | |
| 9,225,190 B2* | 12/2015 | Labbe | H02J 7/007 |
| 9,270,134 B2 | 2/2016 | Gaddam et al. | |
| 9,653,935 B2* | 5/2017 | Cong | H02J 7/0091 |
| 9,851,372 B2* | 12/2017 | Heath | G01F 1/688 |
| 9,929,584 B2* | 3/2018 | Aghassian | A61N 1/3787 |
| 10,554,069 B2 | 2/2020 | Paralikar et al. | |
| 2008/0272742 A1 | 11/2008 | Hart et al. | |
| 2010/0217360 A1* | 8/2010 | Henriksson | A61N 5/0601 607/96 |
| 2010/0256710 A1 | 10/2010 | Dinsmoor et al. | |
| 2013/0193914 A1 | 8/2013 | Gaddam et al. | |
| 2013/0278226 A1 | 10/2013 | Cong et al. | |
| 2014/0048174 A1* | 2/2014 | Lanigan | G05D 7/0647 141/349 |
| 2016/0187272 A1* | 6/2016 | Ishii | G01K 7/42 702/136 |

OTHER PUBLICATIONS

International Search Report and Written Opinion of International Application No. PCT/US2018/041536, dated Sep. 24, 2018, 12 pp.

* cited by examiner

MEDICAL DEVICE TEMPERATURE ESTIMATION

This application is a continuation of U.S. application Ser. No. 15/843,854, which was filed on Dec. 15, 2017. The entire content of application Ser. No. 15/843,854 is incorporated herein by reference.

TECHNICAL FIELD

The disclosure relates to medical devices and, more particularly, systems and methods for estimating temperatures of medical devices based on temperature sensor measurements.

BACKGROUND

Implantable medical devices (IMDs) may be used to monitor a patient condition and/or to deliver therapy to the patient. In long term or chronic uses, IMDs may include a rechargeable power source (e.g., comprising one or more capacitors or batteries) that extends the operational life of the medical device to weeks, months, or even years over a non-rechargeable device.

When the energy stored in the rechargeable power source has been depleted, the patient may use an external charging device to recharge the power source. Since the rechargeable power source is implanted in the patient and the charging device is external to the patient, this charging process may be wireless and referred to as transcutaneous charging. In some examples, transcutaneous charging may be performed via inductive coupling between a primary coil in the charging device and a secondary coil in the IMD.

When a current is applied to the primary coil and the primary coil is located in the area of the secondary coil, electrical current is induced in the secondary coil within the patient. Circuitry associated with the IMD uses the current induced in the secondary coil to charge a rechargeable power source, such as a battery, within the IMD. Therefore, the external charging device does not need to physically connect with the rechargeable power source for charging to occur.

SUMMARY

In general, the disclosure is directed to devices, systems, and techniques for estimating the temperature of a portion of a medical device that is not thermally coupled to a temperature sensor within the medical device. For example, a system may monitor the temperature of a medical device during charging of the rechargeable power source located within an implantable medical device. An implantable medical device (IMD) may include a rechargeable power source that can be transcutaneously charged and a temperature sensor that is not thermally coupled to other components such as the external housing the IMD. During the charging session, the process of inductive coupling may generate heat within the IMD, for example, by electrical current flowing within electrical components within the IMD as part of the charging process. Other sources of heating of the IMD, such as eddy currents generated in the external case forming a housing of the IMD, or increased surrounding tissue temperature from direct tissue heating, may also increase the temperature of various components of the IMD as a byproduct of the charging process.

The IMD and/or the external charger may monitor and/or control the temperature of the IMD through regulation of the power levels and/or the duration of the charging session to maintain a target temperature or temperature range during the charging process. As part of providing this protection to the patient, the IMD may include a temperature sensor configured to measure a temperature at a location within the medical device. However, the temperature sensor may or may not be located at the site where temperature monitoring or control is desired, as the temperature of one or more portions of the IMD may not be reflective of the temperature of the IMD at the location of the temperature sensor or of the IMD as a whole. For example, the temperature sensor may be coupled to an integrated circuit within the IMD, but it may be desirable to monitor the temperature of the external housing of the IMD, instead of the temperature of the integrated circuit, during the charging session to more accurately determine temperatures of the portions of the IMD that are in contact with patient tissue.

The devices, systems, and techniques described herein allow for the estimation of the temperature of a housing or other external surface(s) of an IMD during a recharging process based on temperatures sensed by one or more temperature sensors that are not thermally coupled to the housing, or the external surface, of the IMD. In other words, the IMD or an external device used for recharging of the IMD may be able to determine a temperature of a portion of the IMD that is not directly thermally coupled to the temperature sensor of the IMD. In some examples, various processes may be employed to estimate these temperatures from the measured temperature of the temperature sensor. By controlling the charging of the IMD based on the estimated temperature of the housing of the IMD, the IMD and/or external charger may provide faster recharge sessions while also maintaining safe operating temperatures of the IMD for the patient.

In one aspect, the disclosure is directed to a method comprising: sensing, by a temperature sensor, a temperature of an internal portion of an implantable medical device during a charging process; determining, by processing circuitry and based on the sensed temperature of the internal portion of the implantable medical device and an algorithm, a temperature of a housing of the implantable medical device, the temperature sensor sensing the temperature of the internal portion of the medical device without being thermally coupled to the housing of the medical device, wherein the algorithm is representative of an estimated temperature differential between the internal portion and the housing, the estimated temperature differential determined based on a transfer function; and controlling, by the processing circuitry, charging of a rechargeable power source of the medical device based on the determined temperature of the housing.

In another aspect, the disclosure is directed to a system comprising: an implantable medical device comprising a housing enclosing an internal portion; a temperature sensor disposed within the housing and configured to sense a temperature of the internal portion of the implantable medical device without being directly thermally coupled to the housing and without being configured to sense a temperature of the housing; and processing circuitry configured to determine a temperature of the housing based on the sensed temperature of the internal portion and an algorithm, and to control charging of a rechargeable power source of the implanted medical device based on the determined temperature of the housing, wherein the algorithm is representative of an estimated temperature differential between the internal portion and the housing determined based on a transfer function.

In another aspect, the disclosure is directed to a system comprising: means for sensing a temperature of an internal portion of an implantable medical device during a charging process without being directly thermally coupled to a housing of the implantable medical devices and without being configured to sense a temperature of the housing; means for determining a temperature of a housing of the implantable medical device based on the sensed temperature of the internal portion of the medical device and an algorithm, wherein the algorithm is representative of a temperature differential between the internal portion and the housing determined based on a transfer function; and means for controlling charging of a rechargeable power source of the implantable medical device based on the determined temperature of the housing.

The details of one or more examples are set forth in the accompanying drawings and the description below. Other features, objects, and advantages will be apparent from the description and drawings, and from the claims.

DETAILED DESCRIPTION

Figure 1:
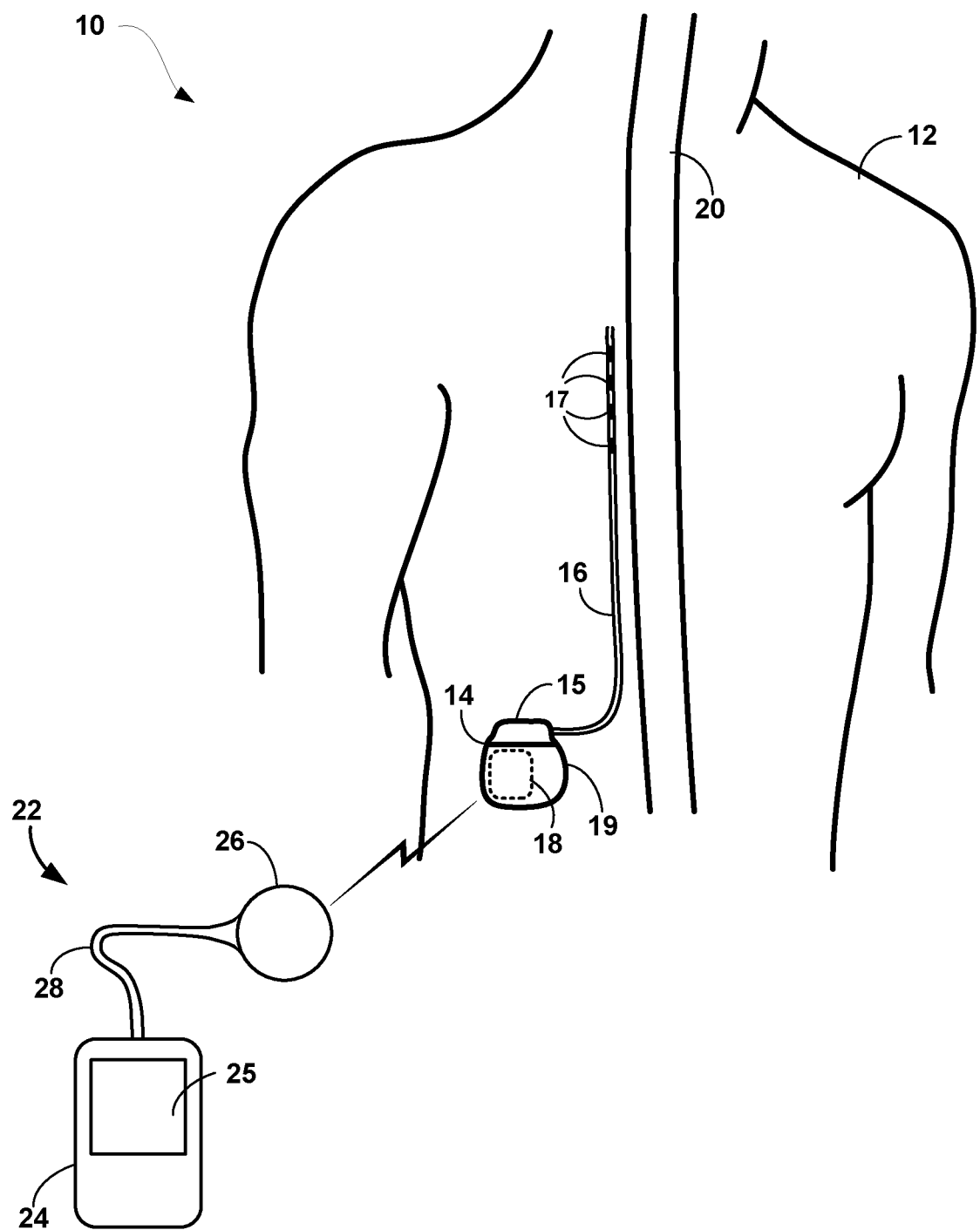
FIG. 1 is a conceptual diagram illustrating an example system that includes an implantable medical device (IMD) and an external charging device that charges a rechargeable power source of the IMD in accordance with the techniques described in this disclosure.

This disclosure is generally directed to devices, systems, and techniques for estimating the temperature of a portion of a medical device that is not thermally coupled to a temperature sensor within the medical device. For example, a system may monitor the temperature associated with charging a rechargeable power source of implantable medical devices (IMDs), and control of the charging session of the rechargeable power source located within the IMD based on the monitoring of at least this temperature.

Generally, IMDs may be implanted within a patient and perform one or more tasks, such as monitoring a parameter of the patient and/or delivering a therapy to the patient. To extend the operational life of the IMD, the IMD may include a rechargeable power source (e.g., one or more capacitors and/or batteries). When the rechargeable power source is being recharged from an external power source, the power transmitted to the IMD may generate heat that increases the temperature of the IMD during the recharging session. For example, inefficiencies with the coupling between the recharging circuitry of the IMD and the charging circuitry of the external charging device providing the power to recharge the IMD may generate heat in the internal circuitry of the IMD. Additional heat may be generated in the housing of the IMD due to eddy currents caused by the electrical fields present during the charging session. The electrical current flowing from the secondary coil of the IMD to the battery of the IMD and electrical current within the battery may generate heat within the IMD. Although the temperature of the IMD housing may not achieve a temperature sufficient to burn or necrose tissue adjacent to the housing of IMD, elevated temperatures may be undesirable, and could cause discomfort to the patient or even tissue damage in some cases.

Therefore, it may be desirable that the temperature of the IMD undergoing the charging session may be monitored and used to control the recharging of the rechargeable power source of the IMD and reduce the exposure of patient tissue to undesirable temperatures. In addition, monitoring the temperature of the IMD may allow the system to minimize the duration of a recharge session by transferring power from the charging device to the IMD at a higher rate for a longer period of time during the recharging session. Fast charging rates may result in a faster increase in the IMD temperature (e.g., the internal and external portions of the IMD) as compared to lower charging rates. However, monitoring a temperature of the housing or another external surface of the IMD during the recharging session may allow the external charging device to charge the rechargeable power source of the IMD at a high charge rate for as long as possible while remaining within safe temperature limits. In other words, systems in which the external surface temperature of the IMD is unknown may need to prematurely reduce charging rates to ensure that the external temperature of the IMD remains within predefined limits. In contrast, a system that monitors or estimates the temperature of the external surface of the IMD may provide higher charging rates until the monitored or estimated external temperature of the IMD indicates that the charging rate should be reduced and, as a result, provides shorter charging sessions.

IMDs may include one or more temperature sensors configured to sense a temperature at a particular location or portion of the IMD. These temperature sensor(s) may also be configured to provide temperature sensing of the particular location or portion of the IMD at which the temperature sensor is located. For example, an IMD may include a temperature sensor, such as a thermistor, a thermocouple, or other temperature sensor that is physically attached and thermally coupled to the surface of a target component (e.g., the component of which temperature is to be sensed) within the IMD. Alternatively, a thermocouple, thermistor, or other temperature sensor, may be disposed within an IMD to sense the ambient temperature within the IMD. However, ambient temperature sensors may not accurately measure different temperatures at specific regions of the IMD of interest or other portions that transfer heat to the patient. Thermistors and/or thermocouples can be directly coupled to a desired surface (e.g., an interior surface of the IMD housing), but these configurations may be difficult and/or expensive to manufacture.

In some examples described herein, one or more temperature sensors of an IMD may be mounted to a printed circuit board located within the IMD, or otherwise integrated into the electronic circuitry mounted to these board or boards, and configured to measure a temperature of the circuitry located on the printed circuit of the IMD. In some examples, devices with these temperature sensors as part of the circuitry mounted to the printed circuit board of the IMD are easier to manufacture than temperature sensors attached to an external housing. For example, when the housing is installed around the board and the temperature sensor(s), no components may need to be mounted to the housing to achieve the desired temperature measurement. Therefore, use of these temperature sensors may reduce assembly time, complexity, and cost as compared to sensors attached to a housing. However, these temperature sensors may not be thermally coupled or arranged to directly sense a temperature of desired structure of the IMD, such as the housing of the IMD.

In some examples, a system may utilize a tissue model in an attempt to estimate the temperature of tissue, or the amount of heat the tissue is exposed to, during the recharge session based on energy applied to the IMD and energy stored in the IMD battery, for example. However, since this approach is still estimating the amount of heat being transferred to the tissue, the actual temperature of the tissue is not being monitored during the charging session. As a result, the system may still need to take a conservative approach with respect to estimating how much heat has been lost, or estimating the temperature of the tissue, during the charging process. This conservative approach may include using lower power levels and/or reducing the charging rate at an earlier point in time during the charging session to ensure that the temperature of the tissue surrounding the IMD remains within a safe temperature range.

The devices, systems, and techniques described in this disclosure determine temperatures for an exterior surface or housing of an IMD based on sensed temperature measurements provided by one or more temperatures sensors within the IMD housing and that are not directly thermally coupled to the housing of the IMD. For example, one or more temperature sensors may be mounted to a printed circuit board of the IMD, and configured to provide temperature measurements associated with measured temperatures of the circuitry and/or the ambient temperature at the location of the temperature sensor coupled to the printed circuit board. Processing circuitry included in the IMD and/or in the recharging device may be configured to determine the current temperature and/or a series of temperatures of the exterior surface and/or the housing of the IMD based on these sensed temperatures.

Therefore, the IMD and/or external charging device may monitor external housing temperatures of the IMD without the need for a temperature sensor to be directly thermally coupled to the housing or to the exterior surface of the IMD. In other words, the IMD does not require the temperature sensor to be mounted to the housing or arranged to directly sense a temperature of the housing in order for the IMD and/or external charging device to monitor the temperature of the IMD housing which contacts patient tissue. Use of these temperature sensors located within the IMD but not directly thermally coupled to the housing or exterior surface of the IMD may reduce assembly time, complexity, and cost for construction of the IMD as compared to attaching a temperature sensor to the housing of the IMD.

Output from one or more temperature sensors that are not directly thermally coupled to the housing or the exterior surface of the IMD may be used by the IMD and/or external charging device to determine an estimation regarding the temperature of the housing and/or exterior surface of the IMD. For example, processing circuitry of the IMD or external charging device may use the measured temperature within the IMD and a calibration algorithm representative of a temperature differential between the portion of the IMD measured by the temperature sensor and the housing of the IMD that would occur during a recharge session. The calibration algorithm may utilize a temperature relationship between these two locations of the IMD during charging, and, in some examples, a temperature decay curve of the external housing may be used to identify one or more constants of the calibration algorithm. The temperature decay curve may be determined experimentally during manufacturing and/or during periods of recharge when the IMD is implanted within the patient.

The IMD and/or external charging device may use the estimated temperature of the IMD housing to control the charging of the implanted rechargeable power source. The IMD and/or external charging device may monitor one or more determined temperatures of the housing and/or exterior surface of the IMD to increase and/or decrease charge rates and/or charging durations to effectively limit temperatures of the IMD housing and the surrounding patient tissue adjacent the IMD and/or external charging device. For example, processing circuitry may provide instructions to reduce the power used during the charging session, to cycle the power to control heat imparted to tissue (e.g., cycle it on and off), reduce the duty cycle of a charging waveform, or to terminate the charging session, in response to the determined temperature for the housing and/or exterior surface of the IMD exceeding predetermined values during the charging process. In other examples, the temperature(s) determined using the techniques described herein may be used to perform other or additional functions. For example, processing circuitry of the IMD and/or the external charging device may compare the determined temperature(s) to a fault condition threshold and disconnect the rechargeable power source from at least one electrical circuit when the determined temperature(s) exceed(s) the fault condition threshold, which may be performed during a time when a charging process is underway and/or during a time when a charging process is not underway.

FIG. 1 is a conceptual diagram illustrating an example system 10 that includes an implantable medical device (IMD) 14 and an external charging device 22 that charges a rechargeable power source 18 of the IMD in accordance with the techniques described in this disclosure. Although the techniques described in this disclosure are generally applicable to a variety of medical devices including medical devices such as patient monitors, electrical stimulators, or drug delivery devices, application of such techniques to implantable neurostimulators will be described for purposes of illustration. More particularly, the disclosure will refer to an implantable neurostimulation system for use in spinal cord stimulation therapy, but without limitation as to other types of medical devices.

As shown in FIG. 1, system 10 includes an IMD 14 and external charging device 22 shown in conjunction with a patient 12, who is ordinarily a human patient. In the example of FIG. 1, IMD 14 is an implantable electrical stimulator that delivers neurostimulation therapy to patient 12, e.g., for relief of chronic pain or other symptoms. Generally, IMD 14 may be a chronic electrical stimulator that remains implanted within patient 12 for weeks, months, or even years. In the example of FIG. 1, IMD 14 and lead 16 may be directed to delivering spinal cord stimulation therapy. In other examples, IMD 14 may be a temporary, or trial, stimulator used to screen or evaluate the efficacy of electrical stimulation for chronic therapy. IMD 14 may be implanted in a subcutaneous tissue pocket, within one or more layers of muscle, or other internal location. IMD 14 includes rechargeable power source 18, such as a rechargeable battery. IMD 14 may be coupled physically and/or electrically to lead 16 by connector block 15. IMD 14 may include a housing 19 that may contact tissue of patient 12 in the area adjacent to the implant site of IMD 14. As used in this disclosure, housing 19 may comprise a housing and/or other structure(s) that provide one or more external portions of IMD 14, excluding lead 16, which may be brought into direct contact with tissue of a patient, such as patient 12, when IMD 14 is implanted within a patient. In general, a temperature measured for and/or determined for the housing 19 may be considered to also be a temperature measured for and/or determined for at least some portion of a housing of IMD 14.

Electrical stimulation energy, which may be constant current or constant voltage based pulses, for example, is delivered from IMD 14 to one or more targeted locations within patient 12 via one or more electrodes 17 of lead 16. The parameters for a program that controls delivery of stimulation energy by IMD 14 may include information identifying which electrodes 17 have been selected for delivery of stimulation according to a stimulation program, the polarities of the selected electrodes, i.e., the electrode configuration for the program, and voltage or current amplitude, pulse rate, pulse shape, and pulse width of stimulation delivered by the electrodes 17. Electrical stimulation may be delivered in the form of stimulation pulses or continuous waveforms, for example.

In the example of FIG. 1, lead 16 is disposed within patient 12, e.g., implanted within patient 12. Lead 16 tunnels through tissue of patient 12 from along spinal cord 20 to a subcutaneous tissue pocket or other internal location where IMD 14 is disposed. Although lead 16 may be a single lead, lead 16 may include a lead extension or other segments that may aid in implantation or positioning of lead 16. In addition, a proximal end of lead 16 may include a connector block 15 that electrically couples to a header of IMD 14. In various examples, connector block 15 may be considered part of the housing 19 and/or an external surface of IMD 14. Although only one lead 16 is shown in FIG. 1, system 10 may include two or more leads, each coupled to IMD 14 and directed to similar or different target tissue sites. For example, multiple leads may be disposed along spinal cord 20, or leads may be directed to spinal cord 20 and/or other locations within patient 12.

Lead 16 may carry one or more electrodes 17 that are placed adjacent to the target tissue, e.g., spinal cord 20 for spinal cord stimulation (SCS) therapy. One or more electrodes 17 may be disposed at a distal tip of lead 16 and/or at other positions at intermediate points along lead 16, for example. Electrodes 17 of lead 16 transfer electrical stimulation generated by an electrical stimulation generator in IMD 14 to tissue of patient 12. The electrodes 17 may be electrode pads on a paddle lead, circular (e.g., ring) electrodes surrounding the body of the lead, conformable electrodes, cuff electrodes, segmented electrodes at different circumferential positions around the lead, or any other type of electrodes capable of forming unipolar, bipolar or multipolar electrode configurations for therapy. In general, ring electrodes arranged at different axial positions at the distal ends of lead 16 will be described for purposes of illustration.

In alternative examples, lead 16 may be configured to deliver stimulation energy generated by IMD 14 to stimulate one or more sacral nerves of patient 12, e.g., sacral nerve stimulation (SNS). SNS may be used to treat patients suffering from any number of pelvic floor disorders such as pain, urinary incontinence, fecal incontinence, sexual dysfunction, or other disorders treatable by targeting one or more sacral nerves. Lead 16 and IMD 14 may also be configured to provide other types of electrical stimulation or drug therapy (e.g., with lead 16 configured as a catheter). For example, lead 16 may be configured to provide deep brain stimulation (DBS), peripheral nerve stimulation (PNS), gastric stimulation to treat obesity or gastroparesis, tibial nerve stimulation, or other deep tissue or more superficial types of electrical stimulation. In other examples, lead 16 may provide one or more sensors configured to allow IMD 14 to monitor one or more parameters of patient 12. The one or more sensors may be provided in addition to, or in place of, therapy delivery by lead 16.

IMD 14 delivers electrical stimulation therapy to patient 12 via selected combinations of electrodes 17 carried by lead 16. The target tissue for the electrical stimulation therapy may be any tissue affected by electrical stimulation energy, which may be in the form of electrical stimulation pulses or waveforms. In some examples, the target tissue includes nerves, smooth muscle, and skeletal muscle. In the example illustrated by FIG. 1, the target tissue for electrical stimulation delivered via lead 16 is tissue proximate spinal cord 20 (e.g., one or more target locations of the dorsal columns or one or more dorsal roots that branch from spinal cord 20). Lead 16 may be introduced into spinal cord 20 via any suitable region, such as the thoracic, cervical or lumbar regions. Stimulation of dorsal columns, dorsal roots, and/or peripheral nerves may, for example, prevent pain signals from traveling through spinal cord 20 and to the brain of the patient. Patient 12 may perceive the interruption of pain signals as a reduction in pain and, therefore, efficacious therapy results. For treatment of other disorders, lead 16 may be introduced at any exterior location of patient 12.

Although lead 16 is described as generally delivering or transmitting electrical stimulation signals, lead 16 may additionally or alternatively transmit electrical signals sensed from patient 12 to IMD 14 for monitoring. For example, IMD 14 may utilize detected nerve impulses to diagnose the condition of patient 12 or to adjust the delivered stimulation therapy. Lead 16 may thus transmit electrical signals to and from patient 12.

A user, such as a clinician or patient 12, may interact with a user interface of an external programmer (not shown) to program IMD 14. Programming of IMD 14 may refer generally to the generation and transfer of commands, programs, or other information to control the operation of IMD 14. For example, the external programmer may transmit programs, parameter adjustments, program selections, group selections, or other information to control the operation of IMD 14, e.g., by wireless telemetry or wired connection.

In some cases, an external programmer may be characterized as a physician or clinician programmer if it is primarily intended for use by a physician or clinician. In other cases, the external programmer may be characterized as a patient programmer if it is primarily intended for use by a patient. A patient programmer is generally accessible to patient 12 and, in many cases, may be a portable device that may accompany the patient throughout the patient's daily routine. In general, a physician or clinician programmer may support selection and generation of programs by a clinician for use by IMD 14, whereas a patient programmer may support adjustment and selection of such programs by a patient during ordinary use. In other examples, external charging device 22 may be included with, or form part of, an external programmer. In this manner, a user such as a clinician, other caregiver, or patient, may program and charge IMD 14 using one device or in some examples multiple devices.

IMD 14 may be constructed of any polymer, metal, or composite material sufficient to house the components of IMD 14 (e.g., components illustrated in FIG. 2) within patient 12. In this example, IMD 14 may be constructed with a biocompatible housing, such as titanium or stainless steel, or a polymeric material such as silicone or polyurethane, and surgically implanted at a site in patient 12 near the pelvis, abdomen, or buttocks. The housing 19 of IMD 14 may be configured to provide a hermetic seal for components, such as rechargeable power source 18. In addition, the housing of IMD 14 may be selected of a material that facilitates receiving energy to charge rechargeable power source 18.

As described herein, rechargeable power source 18 may be included within IMD 14. However, in other examples, rechargeable power source 18 could be located external to a housing of IMD 14, separately protected from fluids of patient 12, and electrically coupled to electrical components of IMD 14. This type of configuration of IMD 14 and rechargeable power source 18 may provide implant location flexibility when anatomical space for implantable devices is minimal. In any case, rechargeable power source 18 may provide operational electrical power to one or more components of IMD 14.

Rechargeable power source 18 may include one or more capacitors, batteries, or components (e.g. chemical or electrical energy storage devices). Example batteries may include lithium-based batteries, nickel metal-hydride batteries, or other materials. Rechargeable power source 18 is also rechargeable. In other words, rechargeable power source 18 may be replenished, refilled, or otherwise capable of increasing the amount of energy stored within the device after energy has been depleted from the rechargeable power source. Rechargeable power source 18 may be subjected to numerous discharge and recharge cycles (e.g., hundreds or even thousands of cycles) over the life of rechargeable power source 18 in IMD 14. Rechargeable power source 18 may be recharged when fully depleted or partially depleted.

External charging device 22 may be used to recharge the rechargeable power source 18 and IMD 14 when implanted in patient 12. External charging device 22 may be a handheld device, a portable device, or a stationary charging system. External charging device 22 may include a user interface 25. User interface 25 may include a display arranged to display information to a user, such as patient 12, related to external charging device 22 and/or recharging process(es) being performed by external charging device 22 and IMD 14. User interface 25 may also be arranged to allow for user inputs to be made to external charging device 22, for example in the form of a touch screen.

In any case, external charging device 22 may include components necessary to charge rechargeable power source 18 through tissue of patient 12. For example, external charging device 22 may include housing 24, charging cable 28, and charging head 26. Housing 24 may enclose or house at least some of the operational components of external charging device 22. For example, housing 24 may include a user interface, processor, memory, power source, and other components. Charging cable 28 may electrically couple charging head 26 to the power source within housing 24, such that charging cable 28 is configured to transmit power and/or information to charging head 26. Charging head 26 may include a coil (e.g., a component of charging head 26) for inductive coupling of components used to transmit power from charging head 26 to rechargeable power source 18. In other examples, charging cable 28 and/or charging head 26 may also be contained within or disposed on housing 24, or various ones of the components associated with external charging device 22 may be carried by cable 28 and/or charging head 26. Although a user may control the recharging process with a user interface, such as user interface 25 of the external charging device 22, charging may alternatively be controlled by another device (e.g., an external programmer).

In some examples, external charging device 22 may only perform charging of rechargeable power source 18. In other examples, external charging device 22 may be an external programmer or other device configured to perform additional functions. For example, when embodied as an external programmer, external charging device 22 may transmit programming commands to IMD 14 in addition to performing charging of rechargeable power source 18. In another example, external charging device 22 may communicate with IMD 14 to transmit and/or receive information related to the charging of rechargeable power source 18. For example, IMD 14 may transmit information regarding temperature of IMD 14 and/or rechargeable power source 18, received power during charging, the charge level of rechargeable power source 18, charge depletion rates during use, or any other information related to power consumption and recharging of IMD 14 and rechargeable power source 18. When external charging device 22 is arranged as an external programmer or other device configured to perform addition functions, user interface 25 may be configured to provide outputs to a user, such as visual display of information, and may be configured to allow a user, such as patient 12, to provide inputs to the external charging device 22, for example using touch screen features or buttons provided by user interface 25.

External charging device 22 and IMD 14 may utilize any wireless power transfer techniques that are capable of charging rechargeable power source 18 of IMD 14 when IMD 14 is implanted within patient 12. In one example, system 10 may utilize inductive coupling between a coil of external charging device 22 (e.g., a coil within charging head 26) and a coil of IMD 14 coupled to rechargeable power source 18. In inductive coupling, external charging device 22 is placed near implanted IMD 14 such that a primary coil of external charging device 22 is aligned with, e.g., placed over, a secondary coil of IMD 14. External charging device 22 may then generate an electrical current in the primary coil based on a selected power level for charging rechargeable power source 18. As further described below, the power level may be selected to control the temperature of IMD 14 and/or the charge rate of rechargeable power source 18. When the primary and secondary coils are aligned, the electrical current in the primary coil may magnetically induce an electrical current in the secondary coil within IMD 14. Since the secondary coil is associated with and is electrically coupled to rechargeable power source 18, the induced electrical current may be used to increase the voltage, or charge level, of rechargeable power source 18. Although inductive coupling is generally described herein, any type of wireless energy transfer may be used to charge rechargeable power source 18.

During the energy transfer process that charges rechargeable power source 18, some of the energy involved in the charging process may be converted into heat at rechargeable power source 18, at other components of IMD 14 such as the housing 19, and/or in the charging head 26, for example. When increased energy levels are used to charge rechargeable power source 18 at a higher rate, the temperature of IMD 14 and/or external charging device 22 may also increase. Although the temperature of the IMD 14 housing 19 and/or the exterior surface(s) of housing 19 may not achieve a temperature sufficient to burn or necrose tissue adjacent to the housing of IMD 14, elevated temperatures may be undesirable and could cause discomfort in some cases. Therefore, one or more devices of system 10 may monitor temperatures of any device or component that may come into contact with or otherwise affect tissue of patient 12. These monitored temperatures may be used as feedback in a closed-loop or partially closed-loop temperature control system. For example, external charging device 22 may control the power level, power cycle times, and/or charging time used to charge rechargeable power source 18 to reduce or minimize any undesirable temperatures of IMD 14 that could be caused by charging rechargeable power source 18. In addition, monitoring the temperature of IMD 14, including monitoring a determined temperature for the housing 19 and/or exterior surface(s) of the housing 19 of the IMD, may minimize patient discomfort during the charging process.

As described herein, system 10 may utilize one or more temperature sensors to sense, measure, or otherwise detect the temperature of a portion of a device such as IMD 14. In one example, a temperature sensor of system 10 may sense the temperature of a portion of an IMD, for example a temperature of electrical components mounted on a printed circuit board housed within IMD 14. This sensed temperature may then be used to determine a temperature of another portion of the medical device, such as the housing 19, e.g., the housing of IMD 14, that is non-thermally coupled with the component where the temperature sensor is directly sensing a temperature. These one or more temperature sensors are not limited to any particular type of temperature sensor(s), and may include one or a combination of temperature sensors, such as a thermistor, a thermocouple, or a resistance thermometer, that are arranged to sense a temperature of some portion of the IMD. In some examples, the one or more temperature sensors include temperature sensor(s), such as a silicon bandgap temperature sensor, that may be incorporated directly into one or more integrated circuits mounted to a printed circuit board enclosed within IMD 14, and arranged to sense a temperature of the electrical circuits and/or the ambient temperature adjacent to the electrical circuits.

In various examples, the measured temperatures provided by the one or more temperature sensors may be used to determine a temperature of the housing 19 and/or the exterior surface(s) of housing 19 of IMD 14, wherein the one or more temperature sensors are not arranged to directly measure a temperature of the housing or the housing 19, and are not directly thermally coupled to the housing 19 or to the exterior surface(s) of IMD 14. The one or more temperature sensors discussed herein are generally described as non-thermally coupled to the housing 19 or exterior surface(s) of the IMD. In other words, the temperature sensor(s) may not be arranged to physically contact or to make direct measurements to sense temperatures of the housing 19 or the exterior portions or the housing 19 of the IMD. Although the temperature sensor may be physically connected or mounted, through one or more members, to the housing of the medical device, the temperature of the housing 19 or the exterior surfaces of the housing portion of the IMD are not sensed or measured by the temperature sensor(s). For example, the temperature sensor(s) may be mounted on a circuit board, such as a printed circuit board of IMD 14, the circuit board may be mounted to a surface of the IMD housing, and the temperature sensor(s) may sense the temperature of the circuitry and/or the circuit board portion of the IMD. The circuit board may be indirectly thermally coupled to the housing of the IMD through a medium, e.g., through a vacuum, air, or another gas separating the temperature sensor(s) from the housing portion of the IMD. However, in various examples the temperature sensor(s) are not configured to measure, sense, or otherwise directly determine a temperature of the housing 19 or the exterior surface(s) of the housing 19 of the IMD.

In various examples, the sensed temperatures provided by the one or more temperature sensors are provided as a variable input to a calibration algorithm that may be used to determine the temperature of the housing 19 and/or exterior surface(s) of the housing 19 of the IMD 14 based on the sensed temperature(s). In some examples, the calibration algorithm used to determine of the temperature of the housing 19 and/or exterior surface(s) of the housing 19 of the IMD 14 based on the sensed temperature(s) provided by the one or more temperature sensors utilizes a transfer function comprising a formula. In various examples, the formula utilized by the calibration algorithm includes a plurality of determined constants derived from a temperature decay curve corresponding to temperature differences measured between the circuit board and the housing 19 of IMD 14, or a similar medical device, immediately following cessation of a recharging operation being performed on the IMD or on a similar medical device. In various examples, the determined constants are stored, for example, in a memory device, and utilized in conjunction with the measured temperatures provided by the one or more temperature sensors as inputs to the formula to determine a current temperature of the housing and/or exterior surface(s) of the housing 19 of IMD 14 during a charging process being performed on the IMD.

Processing circuitry included in system 10 (e.g., one or more processors housed by either the external charging device 22, the IMD 14, or both), may be configured to control charging of rechargeable power source 18 based on the determined temperature of housing 19 and/or exterior surface(s) of the housing 19 based on the sensed temperatures provided by the one or more temperature sensors. In this manner, the non-thermally coupled temperature sensor(s) may provide feedback regarding the temperature of the housing 19 and/or exterior surface(s) of the housing 19, which may then be used for controlling the charging of rechargeable power source 18. For example, external charging device 22 may control a current applied to a primary coil within charging head 26 based on the determined temperature of housing/exterior surface 19. Utilizing the determined temperature of the housing 19 and/or exterior surface(s) of housing 19 based on the techniques disclosed herein, for example using the algorithms described below, may allow a more aggressive recharging regime to be used. For example, utilization of the determined temperature for controlling the charging session may allow using higher power levels for more extended periods of times during the charging session, thus reducing the overall recharging time, while still maintaining safe temperatures levels with respect to patient safety and comfort.

In some examples, IMD 14 may include a single temperature sensor. In other examples, IMD 14 may include two or more temperature sensors. Multiple temperature sensors within the same device may be provided for different reasons. For example, each of the multiple temperature sensors may be configured to sense the temperature of the same portion of the device for redundant, backup, composite, or cross-correlated temperature measurement. If multiple temperature sensors are used, the multiple sensors may be similar or may instead be sensors of different types of non-thermally coupled temperatures sensors described herein.

In some examples, two portions of the IMD being sensed for temperature may be located adjacent to each other (e.g., different locations of a generally planar surface). In this example, two temperature sensors may be mounted to the same side of a circuit board. In other examples, each temperature sensor may be mounted on opposing sides of the circuit board such that one sensor senses temperature on one side of the circuit board and the other sensor senses temperature on the opposite side of the circuit board.

Each temperature sensor may sense temperatures simultaneously such that system 10 may process multiple sensed temperatures at the same time. Alternatively, one or more temperature sensors may be selectively enabled, for example by processing circuitry of the IMD. This selective temperature sensing may reduce power consumption from unnecessary temperature sensors. In addition, selective temperature sensing may reduce power consumption and/or processing speed needed to process signals from unneeded temperature sensors.

System 10 may control the charging of rechargeable power source 18 using one or more techniques. Using the determined temperature for housing 19 and/or exterior surface(s) of housing 19, processing circuitry may compare the determined temperature to a threshold temperature. The processing circuitry may be located within IMD 14 and/or external charging device 22. The threshold temperature may be a value stored by a memory located within IMD 14 and/or within external charging device 22. The threshold temperature may be selected based on tissue models, patient history, or any other information that may be used to determine when a charging session should be modified. The processing circuitry may then determine when the determined temperature of housing 19 and/or exterior surface(s) of housing 19 exceeds the threshold temperature. When the determined temperature exceeds the threshold temperature, the processing circuitry may control charging of rechargeable power source 18 by adjusting a power level used to charge rechargeable power source 18. In other words, the processing circuitry may reduce the power level when the temperature threshold is exceeded, turn the power off for a predetermined period of time before the power is again provided (e.g., cycle the power on and off) or even terminate the charging session.

Reducing the power level may reduce the energy used to charge rechargeable power source 18 and/or the rate at which rechargeable power source 18 is recharged. In other examples, control of the charging process may be based on the determined temperature for the housing 19 and/or exterior surface(s) of housing 19 in conjunction with the cumulative thermal dose provided to the patient during the charging process. The cumulative thermal dose may be a metric used to quantify or estimate the total temperature exposure to tissue adjacent to IMD 14. As such, the cumulative thermal dose may be an estimated cumulative thermal dose. In one example, the cumulative thermal dose may be calculated by integrating the tissue temperature over a period of time. The resulting cumulative thermal dose may be used to equate the delivered heat to a certain tissue temperature level for a certain period of time. For example, the clinician may want to limit tissue exposure to heat for 30 minutes at 43 degrees Celsius. However, the temperature of an IMD will likely vary from any one temperature over the charging period. Calculation of the cumulative thermal dose may thus allow a charging device and/or an IMD to determine when the desired limit to heat exposure is reached even if the actual tissue temperature varies over time. In other examples, the cumulative thermal dose may be calculated by adding the average temperature for multiple segments of the predetermined period of time. In any example, the cumulative thermal dose may be used to determine the total amount of heat or the extent of elevated temperature exposure for tissue surrounding and/or adjacent to an IMD implanted in a patient and for example during a recharging procedure being performed on the IMD.

When sensing a temperature of a component of IMD 14, the processing circuitry of IMD may merely transmit the sensed temperature or data representative of the temperature to external charging device 22. Processing circuitry of external charging device 22 may then determine the temperature of the housing 19 and/or exterior surface(s) of housing 19 of IMD 14 using the techniques described in this disclosure, and/or any equivalents thereof, to determine how to control the charging session being provided to IMD 14. Alternatively, the processing circuitry of IMD 14 may determine how to control the charging session, and transmit a respective command or commands to external charging device 22 to instruct external charging device 22 on how to control the charging session.

External charging device 22 may thus charge rechargeable power source 18 using one or more power levels or cycle times in some examples. In one example, external charging device 22 may select a "high" power level when first starting a charging session. External charging device 22 may then select a "low" power level, relative to the "high" power level, in response to one or more determined temperatures related to the housing 19 and/or exterior surface(s) of housing 19 of IMD 14 exceeding a threshold. In this manner, the "high" power level may charge rechargeable power source 18 at a high rate to reduce charging time while increasing the temperature of IMD 14. External charging device 22 may select the "low" power level to charge rechargeable power source 18 at a slower rate to reduce the temperature of IMD 14. The "low" power level may be sufficiently minimal so that any increase in temperature of IMD 14 may have minimal or no effect on surrounding tissue.

A "high" power level and a "low" power level may be subjective and relative to the charging power that external charging device 22 is capable of generating and transmitting to IMD 14. In some cases, the "high" power level may be the maximum power that external charging device 22 can generate. This "high" power level may be referred to as a "boost" or "accelerated" charging level because of the high rate of charge induced in rechargeable power source 18. This high rate of charge may minimize the amount of time patient 12 needs to recharge rechargeable power source 18. By determining the temperature of the housing 19 and/or exterior surface(s) of housing 19 of IMD 14, and using that determined temperature to control the recharging session, external charging device 22 may charge rechargeable power source 18 with the "high" power level for a longer period of time without damaging tissue surrounding IMD 14.

In one example, the "high" power level may be approximately 2.5 Watts and the "low" power level may be approximately 1.0 Watt (W). Other power levels and ranges may be selected for use, with such levels falling either within the above-described range or outside of this range. For instance, a "low" power level may be much lower than 1.0 W in an example wherein there is good coupling between primary and second coils and wherein recharge is to be conducted relatively slowly. An example charge current level may be approximately 100 milliamps (mA) for the "high" power level and approximately 60 mA for the "low" power level. An example primary coil voltage and current for a "high" power level may be approximately 450 V and approximately 800 mA, respectively, and an example primary coil voltage and current for a "low" power level may be approximately 250 V and approximately 500 mA. These values are merely examples, and other examples may include higher, lower, and/or different values for these power levels for use in accordance with the techniques described herein. In addition, more than two power levels may be defined (e.g., low, one or more intermediate levels, and a high level) to control charging.

In some cases, external charging device 22 may cycle the driving of the primary coil. For instance, external charging device 22 may drive the coil during a first period of time, and may discontinue driving the coil for a second period of time following the first period of time. This may be repeated multiple times, with the first and second time periods being selected to control an overall transmission of power (and hence heat generation/dissipation at IMD 14 and within the patient tissue.)

In some examples, IMD 14 may directly adjust the power level for charging (e.g., limit the charge current) instead of relying on a change in power level at external charging device 22. For example, as IMD 14 receives an alternating charging current, IMD 14 may employ a circuit that may change from full-wave rectification to half-wave rectification to reduce the charge rate and temperature of IMD 14 during charging. In other words, IMD 14 may utilize half-wave rectification as a means to reduce the electrical current delivered to rechargeable power source 18 instead of reducing the overall power received by IMD 14. Alternatively, IMD 14 may employ other mechanisms such as current and/or voltage limiters that may limit the charging rate of rechargeable power source 18.

As described herein, a temperature sensor may be used to sense a temperature of a portion of IMD 14, including rechargeable power source 18 and/or electronic circuitry enclosed within IMD 14. Processing circuitry then uses the sensed temperature information in an algorithm (e.g., a calibration algorithm) that determines (e.g., estimates or calculates) a temperature of the housing 19 and/or exterior surface(s) of housing 19 of IMD 14 based on the sensed temperature information. Based on the determined temperature of the housing 19 and/or exterior surface(s) of the housing 19, processing circuitry further controls an aspect of the charging session being provided to IMD 14. The processing circuitry configured to perform some or all of the functions described herein may be housed together with the one or more temperature sensors, for example within IMD 14, or separately from the temperature sensor(s), for example as part of external charging device 22 or as part of an external programming device.

Although an implantable rechargeable power source 18 is generally described herein, techniques of this disclosure may also be applicable to a rechargeable power source 18 that is not implanted. For example, rechargeable power source 18 may be external to the skin of patient 12 and in physical contact with the skin. Further, a recharging process may be performed on an IMD, for example by a manufacturer, prior to implantation of the IMD, in order to determine values for the constants used in the formula(s) included in the algorithm used to determine the housing 19 and/or exterior surface(s) temperatures of the housing of an IMD during a recharging session as described throughout this disclosure. Therefore, external charging device 22 may control the charging of rechargeable power source 18 with temperature(s) sensed within charging head 26 or IMD 14 even when the IMD is external to patient 12.

Figure 2:
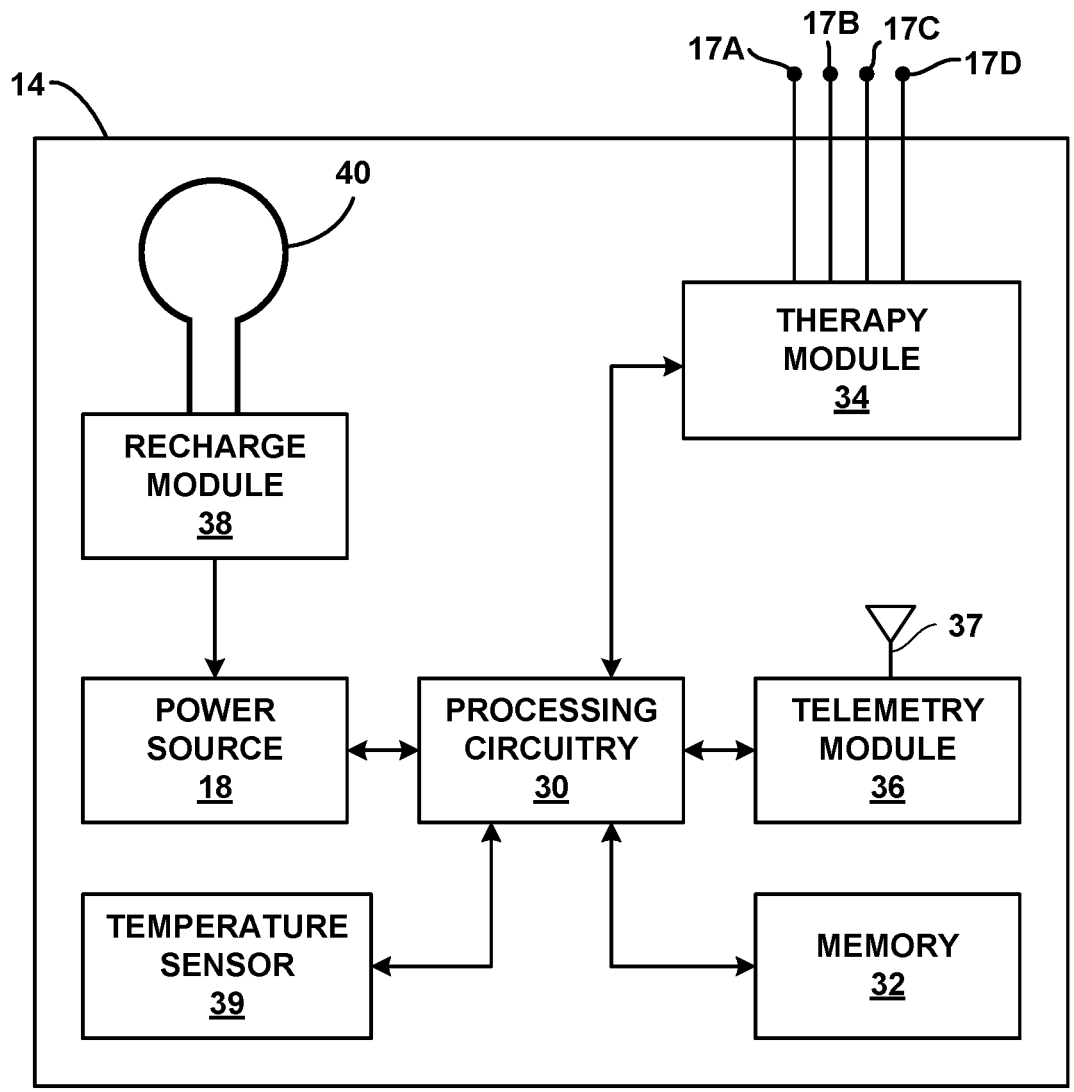
FIG. 2 is a block diagram of the example IMD of FIG. 1.

FIG. 2 is a block diagram illustrating example components of IMD 14 of FIG. 1. In the example illustrated in FIG. 2, IMD 14 includes temperature sensor 39, coil 40, processing circuitry 30, therapy module 34, recharge module 38, memory 32, telemetry module 36, and rechargeable power source 18. In other examples, IMD 14 may include a greater or a fewer number of components. In general, IMD 14 may comprise any suitable arrangement of hardware, alone or in combination with software and/or firmware, to perform the various techniques described herein attributed to IMD 14 and processing circuitry 30, and any equivalents thereof.

Processing circuitry 30 of IMD 14 may include one or more processors, such as one or more microprocessors, digital signal processors (DSPs), application specific integrated circuits (ASICs), field programmable gate arrays (FPGAs), or any other equivalent integrated or discrete logic circuitry, as well as any combinations of such components. IMD 14 may include a memory 32, such as random access memory (RAM), read only memory (ROM), programmable read only memory (PROM), erasable programmable read only memory (EPROM), electronically erasable programmable read only memory (EEPROM), flash memory, comprising executable instructions for causing the processing circuitry 30 to perform the actions attributed to this circuitry. Moreover, although processing circuitry 30, therapy module 34, recharge module 38, telemetry module 36, and temperature sensor 39 are described as separate modules, in some examples, some combination of processing circuitry 30, therapy module 34, recharge module 38, telemetry module 36 and temperature sensor 39 are functionally integrated. In some examples, processing circuitry 30, therapy module 34, recharge module 38, telemetry module 36, and temperature sensor 39 correspond to individual hardware units, such as ASICs, DSPs, FPGAs, or other hardware units.

Memory 32 may store therapy programs or other instructions that specify therapy parameter values for the therapy provided by therapy module 34 and IMD 14. In some examples, memory 32 may also store temperature data from temperature sensor 39, instructions for recharging rechargeable power source 18, thresholds, instructions for communication between IMD 14 and external charging device 22, or any other instructions required to perform tasks attributed to IMD 14. Memory 32 may be configured to store instructions for communication with and/or controlling one or more temperature sensors of temperature sensor 39. In various examples, memory 32 stores information related to determining the temperature of housing 19 and/or exterior surface(s) of housing 19 of IMD 14 based on temperatures sensed by one or more temperature sensors, such as temperature sensor 39, located within IMD 14.

For example, memory 32 may store one or more formulas, as further described below, that may be used to determine the temperature of the housing 19 and/or exterior surface(s) of housing 19 based on temperature(s) sensed by the temperature sensor 39. Memory 32 may store values for one or more determined constants used by these formulas. Memory 32 may store instructions that, when executed by processing circuitry such as processing circuitry 30, perform an algorithm, including using the formulas, to determine a current temperature, or temperatures over time, for the housing 19 and/or exterior surface(s) of the housing 19 of IMD 14 during a charging session and/or for some time after a charging session performed on IMD 14. In some examples, memory 32 may store instructions that, when executed by processing circuitry such as processing circuitry 30, perform an algorithm, including using one or more formulas, to determine a value to be assigned to one or more of the constants used in the algorithm to determine a temperature for the housing 19 and/or exterior surface(s) of the housing 19 of IMD 14 during a charging session and/or for some time after a charging session performed on IMD 14.

Generally, therapy module 34 may generate and deliver electrical stimulation under the control of processing circuitry 30. In some examples, processing circuitry 30 controls therapy module 34 by accessing memory 32 to selectively access and load at least one of the stimulation programs to therapy module 34. For example, in operation, processing circuitry 30 may access memory 32 to load one of the stimulation programs to therapy module 34. In such examples, relevant stimulation parameters may include a voltage amplitude, a current amplitude, a pulse rate, a pulse width, a duty cycle, or the combination of electrodes 17A, 17B, 17C, and 17D (collectively "electrodes 17") that therapy module 34 uses to deliver the electrical stimulation signal. Therapy module 34 may be configured to generate and deliver electrical stimulation therapy via one or more of electrodes 17A, 17B, 17C, and 17D of lead 16. Alternatively, or additionally, therapy module 34 may be configured to provide different therapy to patient 12. For example, therapy module 34 may be configured to deliver drug delivery therapy via a catheter. These and other therapies may be provided by IMD 14.

IMD 14 also includes components to receive power from external charging device 22 to recharge rechargeable power source 18 when rechargeable power source 18 has been at least partially depleted. As shown in FIG. 2, IMD 14 includes secondary coil 40 and recharge module 38 coupled to rechargeable power source 18. Recharge module 38 may be configured to charge rechargeable power source 18 with the selected power level determined by either processing circuitry 30 or external charging device 22. Recharge module 38 may include any of a variety of charging and/or control circuitry configured to process or convert current induced in coil 40 into charging current to charge power source 18. Although processing circuitry 30 may provide some commands to recharge module 38, in some examples, processing circuitry 30 may not need to control any aspect of recharging.

Secondary coil 40 may include a coil of wire or other device capable of inductive coupling with a primary coil disposed external to patient 12. Although secondary coil 40 is illustrated as a simple loop of in FIG. 2, secondary coil 40 may include multiple turns of conductive wire. Secondary coil 40 may include a winding of wire configured such that an electrical current can be induced within secondary coil 40 from a magnetic field. The induced electrical current may then be used to recharge rechargeable power source 18. In this manner, the electrical current may be induced in secondary coil 40 associated with rechargeable power source 18. The induction may be caused by electrical current generated in the primary coil of external charging device 22, where the level of the current may be based on the selected power level. The coupling between secondary coil 40 and the primary coil of external charging device 22 may be dependent upon the alignment of the two coils. Generally, the coupling efficiency increases when the two coils share a common axis and are in close proximity to each other. External charging device 22 and/or IMD 14 may provide one or more audible tones or visual indications of the alignment.

Although inductive coupling is generally described as the method for recharging rechargeable power source 18, other wireless energy transfer techniques may alternatively be used. Any of these techniques may generate heat in IMD 14 such that the charging process may need to be controlled by matching the determined temperature to one or more thresholds, modeling tissue temperatures based on the determined temperature, or using a calculated cumulative thermal dose as feedback.

Recharge module 38 may include one or more circuits that process, filter, convert and/or transform the electrical signal induced in the secondary coil to an electrical signal capable of recharging rechargeable power source 18. For example, in alternating current induction, recharge module 38 may include a half-wave rectifier circuit and/or a full-wave rectifier circuit configured to convert alternating current from the induction to a direct current for rechargeable power source 18. The full-wave rectifier circuit may be more efficient at converting the induced energy for rechargeable power source 18. However, a half-wave rectifier circuit may be used to store energy in rechargeable power source 18 at a slower rate. In some examples, recharge module 38 may include both a full-wave rectifier circuit and a half-wave rectifier circuit such that recharge module 38 may switch between each circuit to control the charging rate of rechargeable power source 18 and temperature of IMD 14.

Rechargeable power source 18 may include one or more capacitors, batteries, and/or other energy storage devices. Rechargeable power source 18 may deliver operating power to the components of IMD 14. In some examples, rechargeable power source 18 may include a power generation circuit to produce the operating power. Rechargeable power source 18 may be configured to operate through many discharge and recharge cycles. Rechargeable power source 18 may also be configured to provide operational power to IMD 14 during the recharge process. In some examples, rechargeable power source 18 may be constructed with materials to reduce the amount of heat generated during charging. In other examples, IMD 14 may be constructed of materials and/or using structures that may help dissipate generated heat at rechargeable power source 18, recharge module 38, and/or secondary coil 40 over a larger surface area of the housing of IMD 14.

Although rechargeable power source 18, recharge module 38, and secondary coil 40 are shown as contained within the housing of IMD 14, in alternative implementations, at least one of these components may be disposed outside of the housing. For example, in some implementations, secondary coil 40 may be disposed outside of the housing of IMD 14 to facilitate better coupling between secondary coil 40 and the primary coil of external charging device 22. These different configurations of IMD 14 components may allow IMD 14 to be implanted in different anatomical spaces or facilitate better inductive coupling alignment between the primary and secondary coils.

IMD 14 may also include temperature sensor 39. Temperature sensor 39 may include one or more temperature sensors configured to measure the temperature of respective portions of IMD 14. As described herein, these temperature sensor(s) may not be thermally coupled to, and may not be directly attached to, the portion of the device for which a temperature is to be determined based on the sensed temperature measured by temperature sensor 39. In one instance, the temperature sensor is not directly attached to the housing 19 or to the exterior surface(s) of housing 19 of the device. In other words, temperature measurement is not performed through direct contact or physical contact between the temperature sensor and the target portion to be measured. Although the temperature sensor may be physically attached to the target portion or target surface through one or more structures, thermal conduction that may occur between the target portion and the sensor is not directly used to measure the temperature of the target portion.

Temperature sensor 39 may be arranged to measure the temperature of a component, surface, or structure, e.g., secondary coil 40, power source 18, recharge module 38, and other circuitry housed within IMD 14. Temperature sensor 39 may be disposed internal of the housing of IMD 14 or otherwise disposed relative to the external portion of housing (e.g., tethered to an external surface of housing via an appendage cord, light pipe, heat pipe, or some other structure). As described herein, temperature sensor 39 may be used to make temperature measurements of internal portions of the IMD 14, the temperature measurements used as a basis for determining the temperature of the housing and/or external surface of IMD 14. For example, processing circuitry 30 or processing circuitry of external charging device 22 may use these temperature measurements to determine the housing/external surface temperatures of IMD 14. In other examples, temperature measurements may be used to determine temperatures of a specific portion of housing 19 or a component coupled thereto, such as header block 15, or another module that is coupled to IMD 14. For instance, IMD 14 may comprise an additional housing that is separate from, but affixed to, housing 19 that contains some components of IMD 14. As one specific example, a secondary coil such as secondary coil 40 may reside within an additional housing that is external to, but affixed to, main housing 19. Temperature measurements may be used to determine a temperature of a surface or portion of this additional housing or a structure within this housing such as the secondary coil itself. As another example, IMD 14 may carry an appendage protruding from housing 19 carrying one or more electrodes that serves as a stub lead for delivering electrical stimulation therapy. Temperature sensor 39 may be used to make temperature measurements that may be used as a basis for determining the temperature of a portion of this structure. The determined temperatures are then further used as feedback to control the power levels or charge times (e.g., cycle times) used during the charging session of rechargeable power source 18. In some examples, temperature sensor 39 may be used to obtain temperature measurements of a header block 15, or another module that is coupled to IMD 14. For instance, IMD 14 may comprise an additional housing that is separate from, but affixed to, housing 19 that contains some components of IMD 14. As one specific example, a secondary coil may reside within an additional housing. As another example, IMD 14 may carry an appendage protruding from housing 19 carrying one or more electrodes that serves as a stub lead for delivering electrical stimulation therapy. Temperature sensor 39 may be used to make temperature measurements that may be used as a basis for determining the temperature of a surface, or another portion, of these and other structures.

Although a single temperature sensor may be adequate, multiple temperature sensors may provide more specific temperature readings of separate components or of different portions of the IMD. Although processing circuitry 30 may continuously measure temperature using temperature sensor 39, processing circuitry 30 may conserve energy by only measuring temperatures during recharge sessions. Further, temperatures may be sampled at a rate necessary to effectively control the charging session, but the sampling rate may be reduced to conserve power as appropriate. Processing circuitry 30 may be configured to access memory, such as memory 32, to retrieve information comprising instructions, formulas, determined values, and/or one or more constants, and to use this information to execute an algorithm to determine a current temperature, and/or a series of temperatures over time, for the housing 19 and/or exterior surface(s) of housing 19 of IMD 14 based on the measured temperature(s) provided by temperature sensor 39.

Processing circuitry 30 may also control the exchange of information with external charging device 22 and/or an external programmer using telemetry module 36. Telemetry module 36 may be configured for wireless communication using radio frequency protocols or inductive communication protocols. Telemetry module 36 may include one or more antennas 37 configured to communicate with external charging device 22, for example. Processing circuitry 30 may transmit operational information and receive therapy programs or therapy parameter adjustments via telemetry module 36. Also, in some examples, IMD 14 may communicate with other implanted devices, such as stimulators, control devices, or sensors, via telemetry module 36. In addition, telemetry module 36 may be configured to control the exchange of information related to sensed and/or determined temperature data, for example temperatures sensed by and/or determined from temperatures sensed using temperature sensor 39.

In some examples, processing circuitry 30 may transmit additional information to external charging device 22 related to the operation of rechargeable power source 18. For example, processing circuitry 30 may use telemetry module 36 to transmit indications that rechargeable power source 18 is completely charged, rechargeable power source 18 is fully discharged, or any other charge status of rechargeable power source 18. In some examples, processing circuitry 30 may use telemetry module 36 to transmit instructions to external charging device 22, including instructions regarding further control of the charging session, for example instructions to lower the power level or to terminate the charging session, based on the determined temperature of the housing/external surface 19 of the IMD.

Processing circuitry 30 may also transmit information to external charging device 22 that indicates any problems or errors with rechargeable power source 18 that may prevent rechargeable power source 18 from providing operational power to the components of IMD 14. In various examples, processing circuitry 30 may receive, through telemetry module 36, instructions for algorithms, including formulas and/or values for constants to be used in the formulas, that may be used to determine the temperature of the housing 19 and/or exterior surface(s) of housing 19 of IMD 14 based on temperatures sensed by temperature sensor 39 located within IMD 14 during and after a recharging session performed on rechargeable power source 18.

Figure 3:
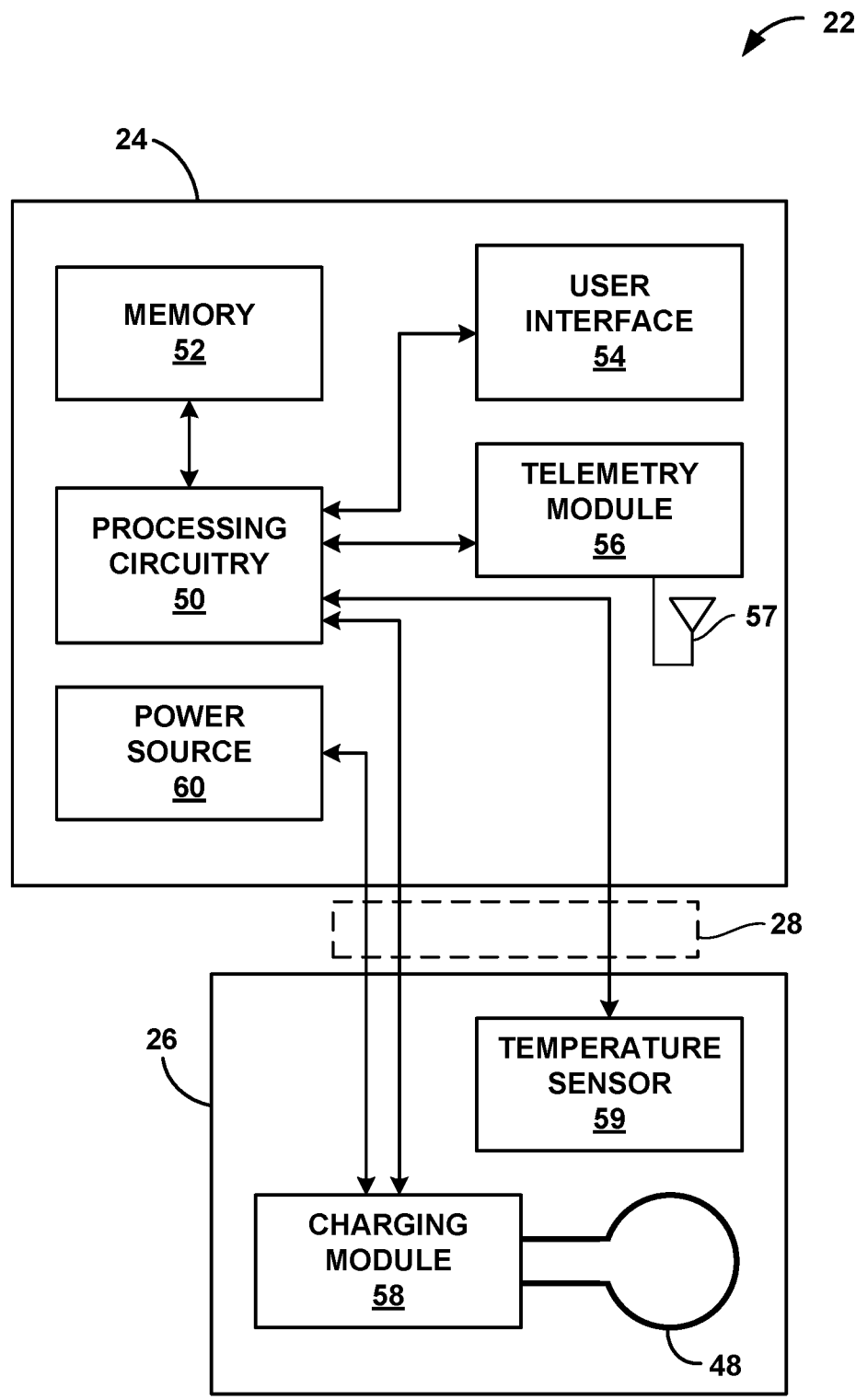
FIG. 3 is a block diagram of the example external charging device of FIG. 1.

FIG. 3 is a block diagram of an example external charging device 22 of FIG. 1. While external charging device 22 may generally be described as a hand-held device, external charging device 22 may be a larger portable device or a more stationary device. In addition, in other examples external charging device 22 may be included as part of an external programmer or include functionality of an external programmer. External charging device 22 may also be configured to communicate with an external programmer. As shown in FIG. 3, external charging device 22 includes two separate components. Housing 24 encloses components such as a processing circuitry 50, memory 52, user interface 54, telemetry module 56, and power source 60. Charging head 26 may include charging module 58, temperature sensor 59, and coil 48. As shown in FIG. 2, housing 24 is electrically coupled to charging head 26 via charging cable 28.

A separate charging head 26 may facilitate optimal positioning of coil 48 over coil 40 of IMD 14. However, charging module 58 and/or coil 48 may be integrated within housing 24 in other examples. Memory 52 may store instructions that, when executed by processing circuitry 50, causes processing circuitry 50 and external charging device 22 to provide the functionality ascribed to external charging device 22 throughout this disclosure, and/or any equivalents thereof.

External charging device 22 may also include one or more temperature sensors, illustrated as temperature sensor 59, similar to temperature sensor 39 of FIG. 2. As shown in FIG. 3, temperature sensor 59 may be disposed within charging head 26. In other examples, one or more temperature sensors of temperature sensor 59 may be disposed within housing 24. For example, charging head 26 may include one or more temperature sensors positioned and configured to sense the temperature of coil 48 and/or a surface of the housing of charging head 26. In some examples, external charging device 22 may not include temperature sensor 59.

In general, external charging device 22 comprises any suitable arrangement of hardware, alone or in combination with software and/or firmware, to perform the techniques ascribed to external charging device 22, and processing circuitry 50, user interface 54, telemetry module 56, and charging module 58 of external charging device 22, and/or any equivalents thereof. In various examples, external charging device 22 may include one or more processors, such as one or more microprocessors, DSPs, ASICs, FPGAs, or any other equivalent integrated or discrete logic circuitry, as well as any combinations of such components. External charging device 22 also, in various examples, may include a memory 52, such as RAM, ROM, PROM, EPROM, EEPROM, flash memory, a hard disk, a CD-ROM, comprising executable instructions for causing the one or more processors to perform the actions attributed to them. Moreover, although processing circuitry 50, telemetry module 56, charging module 58, and temperature sensor 59 are described as separate modules, in some examples, processing circuitry 50, telemetry module 56, charging module 58, and/or temperature sensor 59 are functionally integrated. In some examples, processing circuitry 50, telemetry module 56, charging module 58, and/or temperature sensor 59 correspond to individual hardware units, such as ASICs, DSPs, FPGAs, or other hardware units.

Memory 52 may store instructions that, when executed by processing circuitry 50, cause processing circuitry 50 and external charging device 22 to provide the functionality ascribed to external charging device 22 throughout this disclosure, and/or any equivalents thereof. For example, memory 52 may include instructions that cause processing circuitry 50 to control the power level used to charge IMD 14 in response to the determined temperatures for the housing/external surface(s) of IMD 14, as communicated from IMD 14, or instructions for any other functionality. In addition, memory 52 may include a record of selected power levels, sensed temperatures, determined temperatures, or any other data related to charging rechargeable power source 18. Processing circuitry 50 may, when requested, transmit any of this stored data in memory 52 to another computing device for review or further processing. Processing circuitry 50 may be configured to access memory, such as memory 32 of IMD 14 and/or memory 52 of external charging device 22, to retrieve information comprising instructions, formulas, and determined values for one or more constants, and to use this information to perform an algorithm to determine a current temperature, and/or a series of temperatures over time, for the housing 19 and/or exterior surface(s) of housing 19 of IMD 14 based on the measured temperature(s) provided by temperature sensors 39 of IMD 14.

Memory 52 may be configured to store instructions for communication with and/or control of one or more temperature sensors 39 of IMD 14. In various examples, memory 52 stores information related to determining the temperature of the housing 19 and/or exterior surface(s) of housing 19 of IMD 14 based on temperatures sensed by one or more temperature sensors, such as temperature sensors 39, located within IMD 14. For example, memory 52 may store one or more formulas, as further described below, that may be used to determine the temperature of the housing 19 and/or exterior surface(s) of housing 19 based on temperature(s) sensed by the temperature sensors 39. Memory 52 may store values for one or more determined constants used by these formulas. Memory 52 may store instructions that, when executed by processing circuitry such as processing circuitry 50, performs an algorithm, including using the formulas, to determine a current temperature, or a series of temperatures over time, for the housing 19 and/or exterior surface(s) of housing 19 of IMD 14 during a charging session and/or for some time after a charging session performed on IMD 14. In some examples, memory 52 may store instructions that, when executed by processing circuitry such as processing circuitry 50, perform an algorithm, including using one or more formulas, to determine a value to be assigned to one or more of the constants used in the algorithm used to determine the temperature(s) associated with the housing 19 and/or exterior surface(s) of housing 19 of IMD 14 during a charging session and/or for some time after a charging session performed on IMD 14.

User interface 54 may include a button or keypad, lights, a speaker for voice commands, a display, such as a liquid crystal (LCD), light-emitting diode (LED), or cathode ray tube (CRT). In some examples, the display may be a touch screen. As discussed in this disclosure, processing circuitry 50 may present and receive information relating to the charging of rechargeable power source 18 via user interface 54. For example, user interface 54 may indicate when charging is occurring, quality of the alignment between coils 40 and 48, the selected power level, current charge level of rechargeable power source 18, duration of the current recharge session, anticipated remaining time of the charging session, sensed temperatures, or any other information. Processing circuitry 50 may receive some of the information displayed on user interface 54 from IMD 14 in some examples.

User interface 54 may also receive user input via user interface 54. The input may be, for example, in the form of pressing a button on a keypad or selecting an icon from a touch screen. The input may request starting or stopping a recharge session, a desired level of charging, or one or more statistics related to charging rechargeable power source 18 (e.g., the cumulative thermal dose). User input may also include inputs related to temperature thresholds for the IMD that may be used to regulate for example a maximum housing/surface temperature the patient is willing to experience during a charging session of the IMD. The inputs related to threshold values may be store in memory 52, and/or transmitted through telemetry module 56 to IMD 14 for storage in a memory, such as memory 32, located within IMD 14. In this manner, user interface 54 may allow the user to view information related to the charging of rechargeable power source 18 and/or receive charging commands, and to provide inputs related to the charging process. In various examples, user interface 25 as shown and described with respect to FIG. 1 is arranged to perform and to provide the features and/or functions ascribed to user interface 54 as illustrated and described with respect to FIG. 3.

External charging device 22 also includes components to transmit power to recharge rechargeable power source 18 associated with IMD 14. As shown in FIG. 3, external charging device 22 includes primary coil 48 and charging module 58 coupled to power source 60. Charging module 58 may be configured to generate an electrical current in primary coil 48 from electrical energy stored in or provided by power source 60. Although primary coil 48 is illustrated as a simple loop in FIG. 3, primary coil 48 may include multiple turns of wire. Charging module 58 may generate the electrical current according to a power level selected by processing circuitry 50 based on the sensed and/or determined temperature or temperatures received from IMD 14 and/or a temperature sensor within external charging device 22. As described herein, processing circuitry 50 may select a "high" power level, a "low" power level, or a variety of different power levels to control the rate of recharge in rechargeable power source 18 and the temperature of IMD 14. In some examples, processing circuitry 50 may control charging module 58 based on a power level selected by processing circuitry 30 of IMD 14. The determined temperature of the housing 19 and/or exterior surface(s) of housing 19 of IMD 14 used as feedback for control of the recharge power level may be derived from a temperature sensed by a temperature sensor within IMD 14. Although processing circuitry 50 may control the power level used for charging rechargeable power source 18, charging module 58 may include processing circuitry including one or more processors configured to partially or fully control the power level based on the determined temperatures.

Primary coil 48 may include a coil of wire, e.g., having multiple turns, or other devices capable of inductive coupling with a secondary coil 40 disposed within patient 12. Primary coil 48 may include a winding of wire configured such that an electrical current generated within primary coil 48 can produce a magnetic field configured to induce an electrical current within secondary coil 40. The induced electrical current may then be used to recharge rechargeable power source 18. In this manner, the electrical current may be induced in secondary coil 40 associated with rechargeable power source 18. The coupling efficiency between secondary coil 40 and primary coil 48 of external charging device 22 may be dependent upon the alignment of the two coils. Generally, the coupling efficiency increases when the two coils share a common axis and are in close proximity to each other. User interface 54 of external charging device 22 may provide one or more audible tones or visual indications of the alignment.

Charging module 58 may include one or more circuits that generate an electrical signal, and an electrical current, within primary coil 48. Charging module 58 may generate an alternating current of specified amplitude and frequency in some examples. In other examples, charging module 58 may generate a direct current. In any case, charging module 58 may be capable of generating electrical signals, and subsequent magnetic fields, to transmit various levels of power to IMD 14. In this manner, charging module 58 may be configured to charge rechargeable power source 18 of IMD 14 with the selected power level.

The power level that charging module 58 selects for charging may be used to vary one or more parameters of the electrical signal generated for coil 48. For example, the selected power level may specify wattage, electrical current of primary coil 48 or secondary coil 40, current amplitude, voltage amplitude, pulse rate, pulse width, a cycling rate, or a duty cycle that determines when the primary coil is driven, or any other parameter that may be used to modulate the power transmitted from coil 48. In this manner, each power level may include a specific parameter set that specifies the signal for each power level. Changing from one power level to another power level (e.g., a "high" power level to a lower power level) may include adjusting one or more parameters. For instance, at a "high" power level, the primary coil may be substantially continuously driven, whereas at a lower power level, the primary coil may be intermittently driven such that periodically the coil is not driven for a predetermined time to control heat generation. The parameters of each power level may be selected based on hardware characteristics of external charging device 22 and/or IMD 14.

Power source 60 may deliver operating power to the components of external charging device 22. Power source 60 may also deliver the operating power to drive primary coil 48 during the charging process. Power source 60 may include a battery and a power generation circuit to produce the operating power. In some examples, a battery of power source 60 may be rechargeable to allow extended portable operation. In other examples, power source 60 may draw power from a wired voltage source such as a consumer or commercial power outlet.

External charging device 22 may include one or more temperature sensors shown as temperature sensor 59 (e.g., similar to temperature sensor 39 of IMD 14) for sensing the temperature of a portion of the device. For example, temperature sensor 59 may be disposed within charging head 26 and oriented to sense the temperature of the housing of charging head 26. In another example, temperature sensor 59 may be disposed within charging head 26 and oriented to sense the temperature of charging module 58 and/or coil 48. In other examples, external charging device 22 may include multiple temperature sensors 59 each oriented to any of these portions of device to manage the temperature of the device during charging sessions.

Telemetry module 56 supports wireless communication between IMD 14 and external charging device 22 under the control of processing circuitry 50. Telemetry module 56 may also be configured to communicate with another computing device via wireless communication techniques, or direct communication through a wired connection. In some examples, telemetry module 56 may be substantially similar to telemetry module 36 of IMD 14 described herein, providing wireless communication via an RF or proximal inductive medium. In some examples, telemetry module 56 may include an antenna 57, which may take on a variety of forms, such as an internal or external antenna. Although telemetry modules 56 and 36 may each include dedicated antennas for communications between these devices, telemetry modules 56 and 36 may instead, or additionally, be configured to utilize inductive coupling from coils 40 and 48 to transfer data.

Examples of local wireless communication techniques that may be employed to facilitate communication between external charging device 22 and IMD 14 include radio frequency and/or inductive communication according to any of a variety of standard or proprietary telemetry protocols, or according to other telemetry protocols such as the IEEE 802.11x or Bluetooth specification sets. In this manner, other external devices may be capable of communicating with external charging device 22 without needing to establish a secure wireless connection. As described herein, telemetry module 56 may be configured to receive a signal or data representative of a sensed temperature from IMD 14 or a determined temperature of the housing 19 and/or exterior surface(s) of housing 19 of the IMD based on the sensed temperature. The determined temperature may be determined using an algorithm, including use of formula(s) as further described below, based on measuring the temperature of the internal portion(s) of the IMD, such as circuitry mounted to a circuit board located within IMD 14. In some examples, multiple temperature readings by IMD 14 may be averaged or otherwise used to produce a single temperature value that is transmitted to external charging device 22. The sensed and/or determined temperature may be sampled and/or transmitted by IMD 14 (and received by external charging device 22) at different rates, e.g., on the order of microseconds, milliseconds, seconds, minutes, or even hours. Processing circuitry 50 may then use the received temperature information to control charging of rechargeable power source 18 (e.g., control the charging level used to recharge power source 18).

Figure 4A:
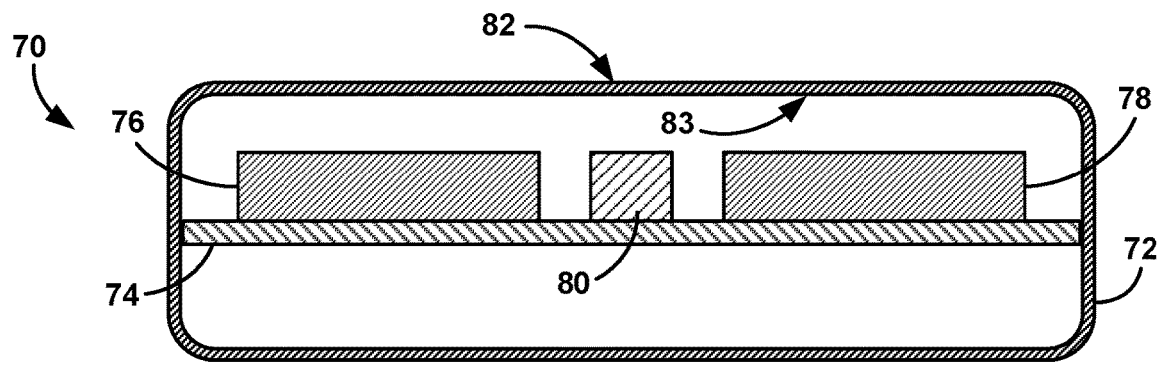
FIGS. 4A-4C are conceptual diagrams illustrating examples of temperature sensors disposed within respective IMDs.
Figure 4B:
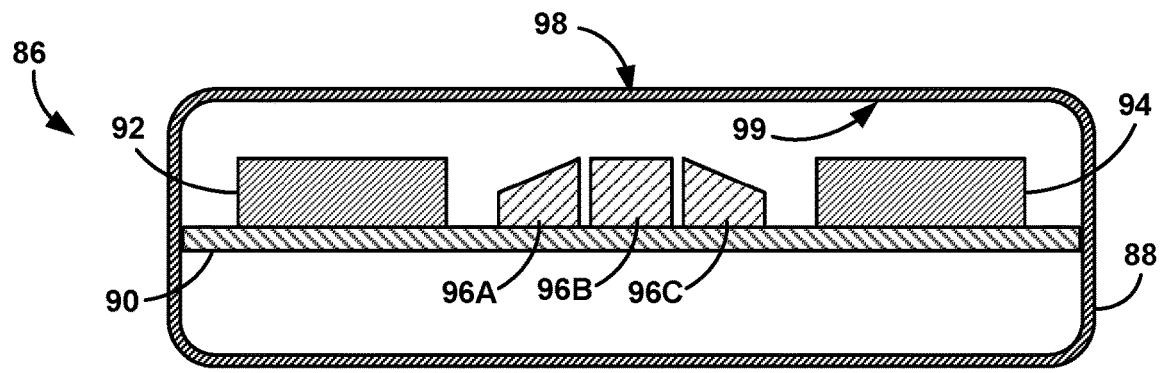
Figure 4C:
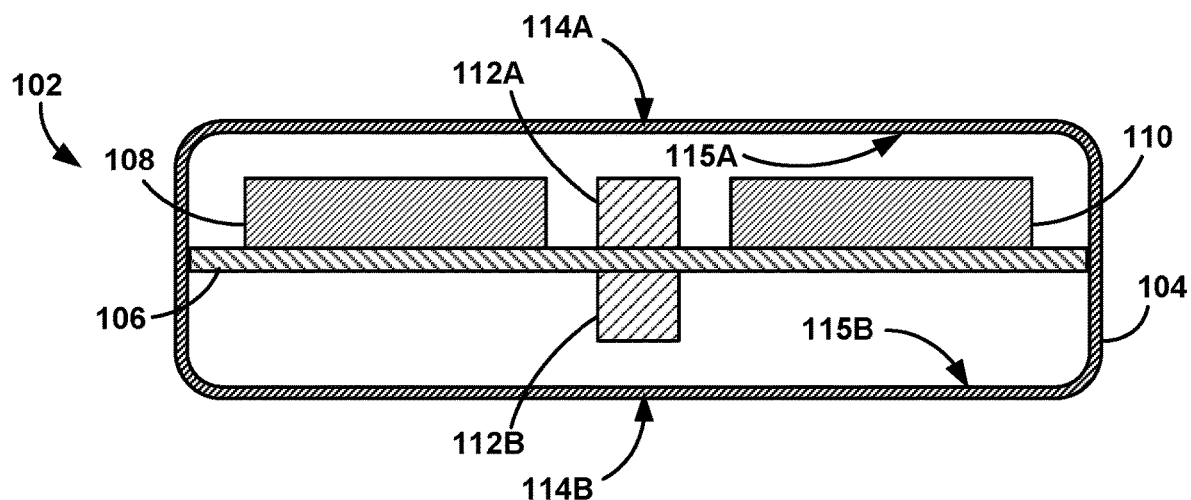

FIGS. 4A-4C are conceptual cross-sectional diagrams illustrating example temperature sensors 80, 96A-C, and 112A-B, disposed within respective IMDs 70, 86, and 102. IMDs 70, 86, and 102 may be examples of IMD 14, and each of temperature sensors 80, 96A-C, and 112A-B may be examples of temperature sensor 39. The IMDs described with respect to FIGS. 4A-4C are generally shown with rectangular cross-sections. However, temperature sensors 80, 96A-C, and/or 112A-B may be disposed within IMDs or any other devices of any shapes, dimensions, or sizes.

As shown in FIG. 4A, IMD 70 includes housing 72 which defines and includes an exterior surface 82 and an interior surface 83. Housing 72 encloses circuit board 74, which may be for example a printed circuit board or a hybrid attached to the printed circuit board, electronic circuits 76 and 78, and temperature sensor 80. Circuit board 74 may be mounted or secured within housing 72. Electronic circuits 76, 78 may be mounted to circuit board 74, or comprise hybrid circuit boards mounted to circuit board 74. Electronic circuits 76 and 78 may include various components such as a processing circuitry, memory, and associated circuitry, such as any of the circuitry shown in FIG. 2 included in IMD 14. Although not shown in FIG. 4A, a secondary coil and rechargeable power source may also be disposed within housing 72. Temperature sensor 80 may be mounted onto a surface of circuit board 74.

Temperature sensor 80 is not limited to any particular type of temperature sensor, and may be for example a thermistor, a thermocouple, a resistance thermometer, or a silicon bandgap temperature sensor. In some cases, temperature sensor 80 may be a dual-range temperature sensor, such as a sensor having a first, broad, less accurate range of measurement and a second, narrow, more accurate range of measurement. Temperature sensor 80 may be a single temperature sensor in some examples, configured to sense a temperature associated with circuit board 74 and/or electronic circuits 76, 78. In various examples, temperature sensor 80 is not directly thermally coupled to housing 72, and is not configured to directly sense a temperature of the housing 72 or the exterior surface 82 of IMD 70. Although temperature sensor 80 is illustrated in FIG. 4A as being physically separated from electronic circuits 76, 78, in some examples temperature sensor 80 may be directly physically coupled to, or for example built into, one or both of electronic circuits 76 and/or 78. The sensed temperature(s) provided by temperature sensor 80 may be processed according to the algorithm(s) described in this disclosure, or any equivalents thereof, to determine a temperature, or a series of temperatures over time, of the housing 72 and/or exterior surface 82 of IMD 70. The determined temperature and/or the series of determined temperatures may be used to control a charging process being performed on IMD 70.

As shown in FIG. 4B, IMD 86 includes housing 88 that includes exterior surface 98 and interior surface 99. Housing 88 encloses circuit board 90, which may be for example a printed circuit board or a hybrid attached to the printed circuit board, electronic circuits 92 and 94, and temperature sensors 96A, 96B, and 96C (collectively "temperature sensors 96"). Circuit board 90 may be mounted or secured within housing 88. Electronic circuits 92, 94 are mounted to circuit board 90, or comprise hybrid circuit boards mounted to circuit board 90. Electronic circuits 92 and 94 may include various components such as a processing circuitry, memory, and associated circuitry, such as any of the circuitry shown in FIG. 2 included in IMD 14. Although not shown in FIG. 4B, a secondary coil and rechargeable power source may also be disposed within housing 88. Temperature sensors 96 may be mounted onto a surface of circuit board 90. In various examples, temperature sensors 96 are not directly thermally coupled to housing 88, and are not configured to directly sense a temperature of the housing 88 or the exterior surface 98 of IMD 86. Although temperature sensors 96 are illustrated in FIG. 4B as being physically separated from electronic circuits 92, 94, in some examples one or more of temperature sensors 96 may be directly physically coupled to, or for example built into one or both of electronic circuits 92 and/or 94.

Temperature sensors 96 are not limited to any particular type of temperature sensor, and may be for example one or some combination of a thermistor, a thermocouple, a resistance thermometer, and/or a silicon bandgap temperature sensor. Temperature sensors 96 may be multiple temperature sensors in some examples, configured to sense a temperature or different temperatures associated with circuit board 90 and/or electronic circuits 92, 94. For example, temperature sensor 96A may be configured to sense a temperature of electronic circuit 92, temperature sensor 96B may be configured to sense a temperature of circuit board 90, and temperature sensor 96C may be configured to sense a temperature of electronic circuit 94. In some examples, more than one of temperatures sensors 96A, 96B and 96C are used at a same time for temperature sensing, these sensed temperatures may be combined for example averaged, to produce a single value for the temperature provided by temperature sensors 96. This single value may be processed according to the algorithm(s) described in this disclosure, and any equivalents thereof, to determine a temperature, or a series of temperatures over time, of the housing 88 and/or exterior surface 98 of IMD 86. In other examples, each sensed temperature provided individually by sensors 96A, 96B, and 96C may be provided separately for individual processing to determine a temperature, or a series of temperatures over time, of the housing 88 and/or exterior surface 98 of IMD 86. The multiple sets of determined temperatures and/or the series of determined temperatures may be used to control a charging process being performed on IMD 86.

As shown in FIG. 4C, IMD 102 includes housing 104 that includes exterior surfaces 114A-B (collectively "exterior surface 114") and interior surfaces 115A-B (collectively "interior surface 115"). Housing 104 encloses circuit board 106, which may be for example a printed circuit board or a hybrid attached to the printed circuit board, electronic circuits 108 and 110, and temperature sensors 112A and 112B (collectively "temperature sensors 112"). Circuit board 106 may be mounted or secured within housing 104. Electronic circuits 108, 110 are mounted to circuit board 106, or to hybrid circuit board(s) mounted to circuit board 106. Electronic circuits 108 and 110 may include various components such as a processing circuitry, memory, and associated circuitry such as any of the circuitry shown in FIG. 2 included in IMD 14. Although not shown in FIG. 4C, a secondary coil and rechargeable power source may also be disposed within housing 104.

As shown, in FIG. 4C, temperature sensors 112 may be mounted onto opposite sides of circuit board 106. In various examples, temperature sensors 112 are not directly thermally coupled to housing 104, and are not configured to sense a temperature of the housing 104 or the exterior surfaces 114 of IMD 102. Although temperature sensors 112 are illustrated in FIG. 4C as being physically separated from electronic circuits 108, 110, in some examples one or more of temperature sensors 112 may be directly physically coupled to, or for example built into, one or both of electronic circuits 108 and/or 110.

In some examples, sensing the temperature on opposing sides of the circuit board 106 of IMD 102 may be beneficial if IMD 102 becomes flipped within the tissue pocket containing IMD 102 within patient 12. In other words, IMD 102 may be configured to determine that a flip has occurred and/or measure the temperature of a desired surface 114A, 114B of housing 104 regardless of if IMD 102 has flipped within patient 12. In some examples, the differences in temperatures of surfaces 114A, 114B may be negligible due to the thermal conductance of the material used to form housing 104, and therefore determined temperatures based on sensed temperatures provided by either of temperature sensors 112A or 112B would be equally useful in determining the temperature of the exterior surfaces 114 of housing 104 using the techniques, and any equivalents thereof, as described in this disclosure. For example, temperature sensor 112A may be configured to sense a temperature of electronic circuits 108, 110, and temperature sensor 112B may be configured to sense a temperature of circuit board 106.

In some examples, more than one of temperatures sensors 112A, 112B are used at the same time for temperature sensing, these sensed temperatures may be combined, for example averaged, to produce a single value for the temperature provided by temperature sensors 112. This single value may be processed according to the algorithm(s) described in this disclosure, and any equivalents thereof, to determine a temperature, or a series of temperatures over time, of the housing 104 and/or exterior surfaces 114A, 114B of IMD 102. In other examples, each sensed temperature provided individually by sensors 112A, 112B may be provided separately for individual processing to determine a temperature, or a series of temperatures over time, of the housing 104 and/or exterior surface 114 of IMD 102. The determined sets of temperatures and/or the series of determined temperatures may be used to control a charging process being performed on IMD 102.

Figure 5A:
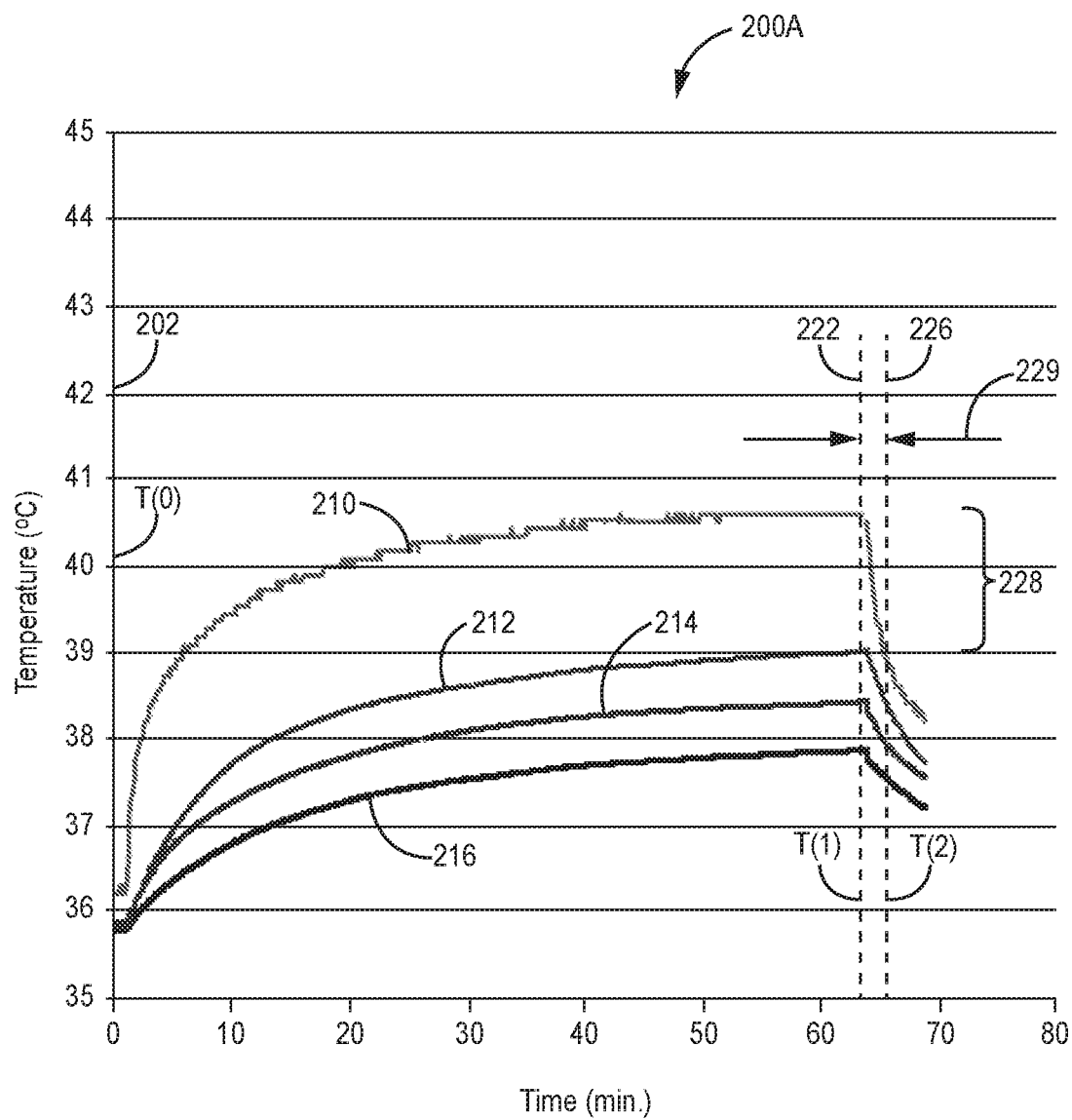
FIG. 5A is a graph of example temperatures generated at different portions of an IMD over a period of time during and after recharging a rechargeable power source of the IMD in accordance with the techniques described in this disclosure.

FIG. 5A is a graph 200A illustrating various examples of temperatures measurements of an implanted medical device during and just after a recharging process in accordance with various techniques described in this disclosure. Graph 200A includes a vertical axis representing temperature in degrees Celsius (° C.), and a horizontal axis representing time in minutes. At time T(0), as represented by vertical line 202 in graph 200A, a recharging process of an IMD is initiated. In various examples, the IMD is IMD 14 as illustrated and described with respect to FIG. 1.

Referring to FIG. 5A and graph 200A, various temperatures associated with the IMD are graphed over time relative to the rise in temperature associated with various portions of the IMD. For example, graphical line 210 in graph 200A represents a rise in temperature at internal electronic circuitry, such as electronic circuits 76, 78 as illustrated and described with respect to FIG. 4A. The temperature sensed by a temperature sensor within IMD 14 may correspond to the temperature of graphical line 210. Graphical line 212 as shown in FIG. 5A represents a rise in temperature of a front exterior surface of a case of the IMD, for example exterior surface 82 of IMD 70 as illustrated and described with respect to FIG. 4A. Graphical line 214 as shown in FIG. 5A represents a rise in temperature of a back exterior surface portion of a case of the IMD, for example a back exterior side of housing 72 opposite the top portion of exterior surface 82 of IMD 70, as illustrated and described with respect to FIG. 4A. Graphical line 216 as shown in FIG. 5A represents a rise in temperature of at a connector block of a case of the IMD, not specifically shown in FIG. 4A, but for example connector block 15 as shown in conjunction with IMD 14 in FIG. 1.

Referring again to FIG. 5A and graph 200A, the temperatures associated with each of graphical lines 210, 212, 214, and 216 rises at various rates and to various levels over the time period between time T(0) and time T(1), time T(1) represented by vertical dashed line 222 in graph 200A. At time T(1), as represented by vertical dashed line 222 in graph 200A, the recharging process being applied to the IMD is halted. The recharging process may be halted at time T(1), for example by removing the electrical power being applied to a primary coil being used to provide the recharging power to the IMD. Halting of the recharging process may occur based on a determination that the battery or other device within the IMD being recharged has reached a pre-defined level of recharge, such as the full charge capacity for the battery or other device being recharged.

Shortly after the recharging process is halted at time T(1), the temperatures associated with each of the portions of the IMD begin to decrease, as illustrated by the downward direction for each of graphical lines 210, 212, 214, and 216 following time T(1). As further illustrated in graph 200A, the rate of decrease in the temperature of the internal electronic circuitry of the IMD, as illustrated by graphical line 210, may be greater than the rate of decrease in temperature for the other portions of the IMD, as represented by graphical lines 212, 214, and 216 following the halting of the recharging process at time T(1). The rate of decrease of the temperature associated with the internal electronic circuitry after time T(1) may be generally described as an exponential decay, which may be referred to herein as a temperature decay curve.

A transfer function associated with the decay of the temperatures of the IMD as shown in FIG. 5A is generally related to one or more thermal properties of the IMD, and may be repeatedly consistent for a given IMD for any charging session. In addition, a same transfer function may also consistently apply to the decay in temperatures as illustrated in FIG. 5A for IMDs of a same general type and size, for example between individual instances of a plurality of IMDs of a same model. This feature allows the determined transfer function for a given IMD to be utilized to determine the external surface temperature, respectively, for any particular one of a plurality of IMDs of a same type and size, e.g., a same model IMD, during times when the particular IMD is undergoing a recharging process. By determining the parameters of the transfer function, the formula(s) and constant values determined for the transfer function can be applied to any of these same IMDs for use in determining the exterior surface temperatures of any of the IMDs during and following a recharging session performed on that IMD without having to individually test each IMD.

As shown in graph 200A, at time T(2), represented by vertical dashed line 226, the temperature of the internal electronic circuitry as illustrated by graphical line 210 has cooled to a temperature that has a same value as the temperature of the face of the IMD as represented by graphical line 212 at time T(2). The decrease in the internal temperature of the electronic circuitry between time T(1) and time T(2) is represented by the difference in temperature 228, and occurs over a time period 229 occurring between time T(1) and time T(2). The temperature difference 228 in some examples is the difference 40.6-39.0 degrees Celsius, representing the difference between the temperature indicated by graphical line 210 at time T(1) and time T(2), or approximately 1.6 degrees Celsius. The time difference 229 between time T(1) and T(2) may be in a range of two to three minutes.

The determined temperature difference 228, along with the determined time difference 229, can be used as input parameters to an algorithm that allows the output values provided by a sensor sensing the temperature of the internal electronic circuitry associated with graphical line 210 to be used to estimate a temperature for the housing/external surface(s) of the IMD without the need for a temperature sensor to be in direct thermal contact with the housing/external surface(s) of the IMD. As illustrated in FIG. 5A, when the recharge operation is turned off the temperature of the internal electronic circuitry at time $t_i$ can be approximated by Equation 1:

$$T_H(t_i) = T_f(t_i) + A_0 e^{-(t_i - t_0)/\tau} \quad \text{(Equation 1)}$$

wherein:
$T_H(t_i)$=the internal temperature (e.g., temperature of the electronic circuitry within IMD),
$T_f(t_i)$=temperature of the front face of the IMD,
$A_0$=temperature difference between $T_H$ and $T_f$ at $t_0$, the time recharge is shut off,
$\tau$=a time constant–the time required for a temperature difference between the IMD temperature $T_H$ and the temperature $T_f$ of the front face of the IMD to achieve a value of thirty-seven percent of the initial values for $A_0$ if $T_f$ were held constant.

At the instant the recharge process is shut off, $t_i = t_0$; then, $t = t_i - t_0 = 0$, $$T_H(t=0) = T_f(t=0) + A_0 e^{-0/\tau} \quad \text{(Equation 2)}$$

i.e.

$$T_H(t=0) = T_f(t=0) + A_0$$

Equation 1 can be rearranged for use in calculating the temperature of the face of the IMD based on the internal electronic circuitry temperature as follows:

$$T_f(t) = T_H(t) - A_0 e^{-t/\tau} \quad \text{(Equation 1A)}$$

To find $A_0$, first consider a scenario where the time constant $\tau$ is known. Two methods for estimation of $\tau$ are further described below. If the internal electronic circuitry temperature is measured at two different time-points—$t_1$ and $t_2$ on graph 200A—by obtaining the sensor's output values for internal temperature after shutting down the recharge process, $A_0$ may be estimated using Equations 3-7 as follows:

$$T_H(t=t_1) = T_H(t_1) = T_f(t_1) + A_0 e^{-t_1/\tau} \quad \text{(Equation 3)}$$

$$T_H(t_2) = T_f(t_2) + A_0 e^{-t_2/\tau} \quad \text{(Equation 4)}$$

$$\begin{aligned}\Delta T_H(t_1, t_2) &= T_H(t_1) - T_H(t_2) \quad \text{(Equation 5)}\\ &= (T_f(t_1) + A_0 e^{-t_1/\tau}) - (T_f(t_2) + A_0 e^{-t_2/\tau})\\ &= T_f(t_1) - T_f(t_2) + A_0 e^{-t_1/\tau} - A_0 e^{-t_2/\tau}\\ &= (T_f(t_1) - T_f(t_2)) + A_0 e^{-t_1/\tau} - A_0 e^{-t_2/\tau}\\ &= \Delta T_f(t_1, t_2) + A_0(e^{-t_1/\tau} - e^{-t_2/\tau})\end{aligned}$$

Assuming $t_1$ and $t_2$ are relatively close in time to each other and that the rate of temperature change at the exterior of IMD is much slower that the rate of decay of the internal temperature, a conservative estimate can be made that: $T_f(t_1) \sim T_f(t_2)$ and $\Delta T_f(t_1, t_2) \approx 0$. Based on these assumptions, the change in temperature between times $t_1$ and $t_2$ can be calculated as follows:

$$\Delta T_H(t_1, t_2) = A_0(e^{-t_1/\tau} - e^{-t_2/\tau}) \quad \text{(Equation 6)}$$

Isolating Equation 6 for $A_0$ provides:

$$A_0 = [T_H(t_1)] - [T_H(t_2)]/[e^{-t_1/\tau} - e^{-t_2/\tau}] \quad \text{(Equation 7)}$$

In order to determine $A_0$, a value for $\tau$ is needed, which can be determined using various approaches. In some examples, temperature data from temperatures sensors, such as thermistors, is collected for temperatures of the front case of the IMD and from electronic circuitry within the IMD for varying coupling conditions. A value for $\tau$ may be determined based on this data. Collection of data may include determining variability of the value of τ for differing coupling conditions.

Figure 6:
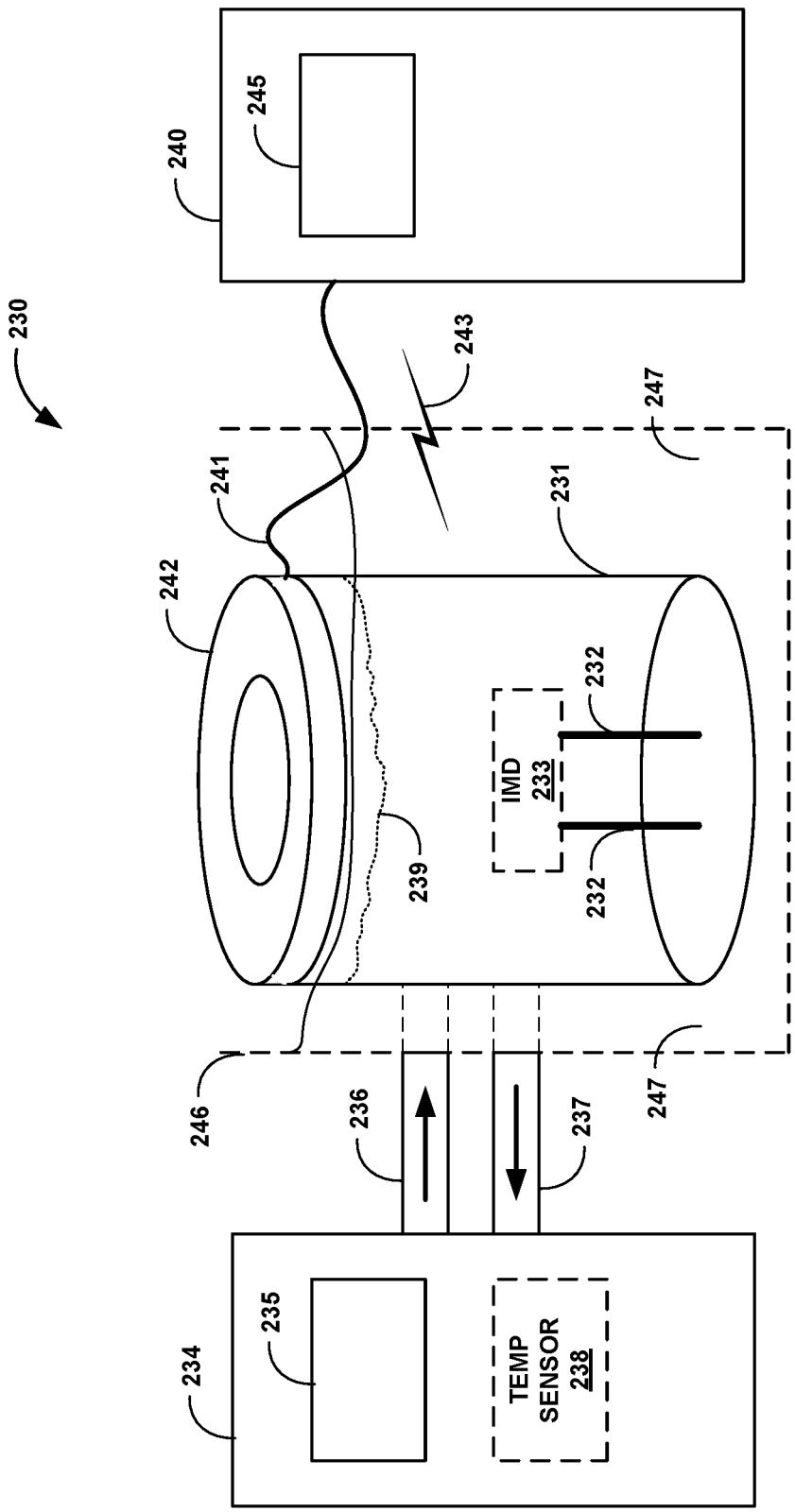
FIG. 6 is a layout diagram illustrating a system including a test chamber that may be used to determine one or more constant values associated with thermal properties of an IMD in accordance with the techniques described in this disclosure.

In an example approach to determine the value for τ, a test chamber into which the IMD is placed may be utilized (such as system 230 of FIG. 6). The test chamber is arranged to maintain a constant temperature $T_{Test}$, for example at 37° Celsius. When the IMD is placed within the test chamber, the IMD itself is allowed to remain in the test chamber for some period of time so that the temperature of the front face of the IMD and the IMD will be at this same temperature $T_{Test}$. A temperature sensor, for example the temperature sensor sensing the temperature of the electronic circuitry within the IMD, is calibrated to the temperature $T_{Test}$ once it has been determined that the IMD has reached a steady-state temperature of $T_{Test}$. A recharging process of the IMD is then begun for a period of time that is sufficient to result in a charge current flow to the battery or other power source within the IMD that results in increase of the temperature at the sensor, but without changing the external temperature of the face of the IMD appreciably. For example, any increase in the temperature of the face of the IMD would be no more than a variation in temperature due to the noise in the temperature measurement.

At the end of this charging period, and immediately after turning off the power being provided to perform the charging process, a reading of the temperature sensed by the electronic circuitry temperature sensor is taken. This sensed temperature is $T_H(t_0)=A_0+T_{Test}$. After turning off the power being used for the recharging process and collecting the sensed temperature of the electronic circuitry temperature sensor, the temperature of the IMD is allowed to stabilize toward $T_{Test}$. Because the temperature of the test chamber is being maintained at $T_{Test}$, the temperature of the IMD, and the temperature at the sensor sensing the electronic circuitry temperature, should begin to decrease, and eventually to stabilize at the temperature $T_{Test}$. For $t=t_i-t_0$ and for any time $t_i>t_0$, $$T_H(t)-T_{Test}=A_0 e^{-t/\tau}=(T_H(t_0)-T_{Test})e^{-t/\tau} \quad \text{(Equation 8)}$$

The value for τ may be obtained by solving Equation 8.

$$\tau = -t/[\ln((T_H(t)-T_{Test})/A_0)]$$
$$= -t/[\ln(T_H(t)-T_{Test}) - \ln(T_H(t_0)-T_{Test})]$$

Using this technique, is not required that the temperature of the IMD at time $t_0$ returns to the $T_{Test}$ temperature. Further, it is not necessary that the recharging process be halted only when the power source of the IMD being recharged has been fully recharged in order to collect measurements of the temperature differential 228 and the time period 229. Measurements to determine values for temperature differential 228 and the time period 229 in order to determine a transfer function as described above may be collected by halting a recharging process, either temporarily or permanently, at different points along the recharging process where the rate of change between the sensed temperature of the electronic circuitry (as depicted by line 210) and the exterior surface of the IMD (as depicted for example by line 212) have stabilized relative to one another. These areas of the curves represented in graph 200A may exist after about a five minute time period following initiation of the recharging process shown in FIG. 5A. In using the test chamber as described above, the relationship between the locations of the primary coil and the location of the IMD, and hence the coupling conditions between the primary coil and the recharging circuitry of the IMD, can be precisely controlled and repeated, for example using an automated system. Using such a system, multiple estimates for τ can be made at different times $t_i>t_0$. In some examples, the values obtained for these multiple estimates of τ may be averaged to provide an average value for τ that reduces the error due to measurement noise. A test chamber that may be used to perform the above described techniques is illustrated and described below with respect to FIG. 6.

As similar technique may be utilized to provide estimates for τ after an IMD is implanted in a patient. The techniques may build upon the procedure described above with respect to use of a test chamber, and further refine the transfer function based on the particular pocket condition of the patient where the IMD is implanted.

In using the technique on an implanted IMD, at some time when the IMD is not being charged by an external charging device, for example just before a recharging cycle is to be commenced, temperature being sensed by the temperature sensor associated with the electronic circuitry temperature of the implanted IMD is collected as a baseline temperature, $T_{Patient}$. A recharging of the IMD is begun for a short period of time, e.g., less than one minute, at an energy level sufficient to generate a recharging current flow in the recharging circuitry of the IMD that raises the temperature at the temperature sensor without raising the external temperature of the face of the IMD, referred to as $T_f$, for example more than a variation in the temperature of the due to measurement noise. At the end of this short recharging period, the power being provided to the recharging process is removed, and immediately after removing the recharging power, the temperature above being sensed by the electronic circuitry temperature sensor is captured. This temperature is $T_H(t_0)=A_0+T_{Patient}$, assuming $T_{Patient}$ is stable and therefore approximately constant.

After turning off the power being used for the recharging process and collecting the sensed temperature of the electronic circuitry temperature sensor, the temperature of the IMD is allowed to stabilize toward $T_{Patient}$. The above described algorithm may again be used as the temperature profile of the electronic circuitry temperature sensor as the sensed temperature returns to a value of $T_{Patient}$.

Again, for $t=t_i-t_0$, and for any $t_i>t_0$:

$$\tau = -t/[\ln((T_H(t)-T_{Patient})/A_0)] \quad \text{[Equation 9]}$$
$$= -t/[\ln(T_H(t)-T_{Patient}) - \ln(T_H(t_0)-T_{Patient})]$$

Multiple estimates of τ, in a manner similar to that described above, may be made for the implanted IMD, and for example averaged to reduce the error due to measurement noise. In addition, this process for an implanted IMD may be repeated at various intervals over the lifetime of the IMD to recalibrate and/or to average the determined value of τ for the implanted IMD. The calibration algorithm used to determine the temperature of the housing of IMD 14 may use, or be based on, any of the equations 1-9 above.

In addition, calculated values for τ obtained over a lifetime of an implanted IMD may be an indication of a change in the integrity of the device. For example, sudden changes, or a trend of change in the values for τ may be an indication of conditions such as, but not limited to a change in the physical condition of the IMD. The measured values for τ may be used as a warning sign, as part of a diagnostic system, to indicate that such a deterioration or other comprising condition of the IMD is taking place. In this manner, IMD 14, or external charging device 22 or another device, may monitor any changes to τ, with respect to one or more thresholds, rates of change, or other metrics. In response to determining that a change to τ has exceeded one of these thresholds or rates, IMD 14 or another device may, for example, flag the change for a user or even take one or more actions such as reduce charging rates or disable one or more components of IMD 14.

Once values for $A_0$ and the time constant τ have been determined, these values may be stored in a memory of the IMD, such as memory 32 as described with respect to FIG. 2, and retrieved by processing circuitry, such as processing circuitry 30 or processing circuitry 50, for use in a formula, such as Equation 1/1A, to calculate the temperature of the housing or external surface of the IMD based on the value of the sensed temperature provided by the temperature sensor(s) located within the IMD and sensing a temperature associated for example with the circuitry housed within the IMD. Because the determined values of $A_0$ and the time constant τ are properties related to the thermal properties of the IMD itself, these same determined constants will be applicable to IMDs having the same physical construction from one IMD to another IMD. In other words, a manufacturer may determine the values of $A_0$ and for the time constant τ for a particular model of IMD. These same values may be stored into memory and used by other IMDs of the same model to provide the feature of being able to determine the temperature of the housing/external surface of each of these IMDs during a recharging session without the need to measure and establish these constant values for each IMD individually.

In some examples, the values for $A_0$ and the time constant τ may be determined, for example using the test chamber example described above, for a particular model of IMD. These determined values may then be stored into the memory of each of a plurality of IMD of that same model, for example by the manufacturer and prior to implantation of the IMD. The stored values may then be used by each individual IMD during a charging session performed on that particular IMD to determine a temperature of the housing and/or external surface of the IMD based on the sensed temperatures provided by one or more temperature sensors located within the IMD but not directly thermally coupled to the housing or the external surfaces of the IMD. The determined temperatures may be used by the IMD and/or a recharging device to control and optimize the recharging process being performed on the individual IMD. In some examples, the value for example for τ for an individual IMD may be retested and/or replaced in memory by performing the post-implant test procedure described above, for an individual IMD that has been implanted and remains implanted in a patient.

Figure 5B:
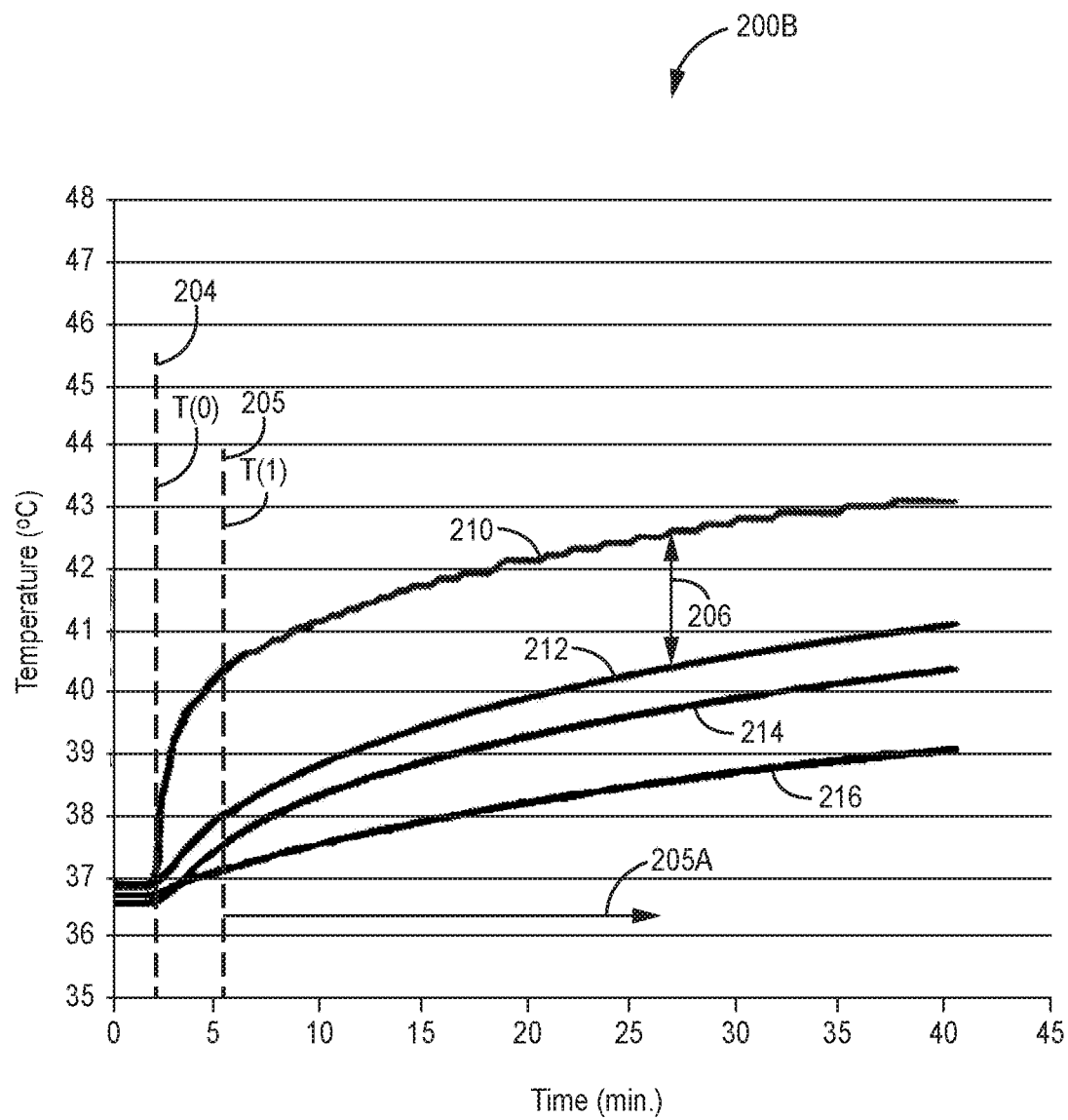
FIG. 5B is a graph of example temperatures generated at different portions of an IMD over a period of time during recharging a rechargeable power source of the IMD in accordance with the techniques described in this disclosure.

FIG. 5B is a graph 200B of example temperatures generated at different portions of an IMD over a period of time during recharging a rechargeable power source of the IMD in accordance with the techniques described in this disclosure. Graph 200B includes a vertical axis representing temperature in degrees Celsius (° C.), and a horizontal axis representing time in minutes. At time T(0), as represented by vertical line 204 in graph 200B, a recharging process of an IMD is initiated. In various examples, the IMD is IMD 14 as illustrated and described with respect to FIG. 1.

Referring to FIG. 5B and graph 200B, various temperatures associated with the IMD are graphed over time relative to the rise in temperature associated with various portions of the IMD. The temperatures illustrated in graph 200B are examples of measured temperatures measured at various portions of an IMD, such as IMD 14 described above, during a recharging session, wherein the IMD was placed in a controlled environment similar to that described below with respect to FIG. 6. Referring again to FIG. 5B, graphical line 210 in graph 200B represents a rise in temperature at internal electronic circuitry, such as electronic circuits 76, 78 as illustrated and described with respect to FIG. 4A. The temperature sensed by a temperature sensor within the IMD may correspond to the temperature of graphical line 210. Graphical line 212 as shown in FIG. 5B represents a rise in temperature of a front exterior surface of a case of the IMD, for example exterior surface 82 of IMD 70 as illustrated and described with respect to FIG. 4A. Graphical line 214 as shown in FIG. 5B represents a rise in temperature of a back-exterior surface portion of a case of the IMD, for example a back-exterior side of housing 72 opposite the top portion of exterior surface 82 of IMD 70, as illustrated and described with respect to FIG. 4A. Graphical line 216 as shown in FIG. 5B represents a rise in temperature of at a connector block of a case of the IMD, not specifically shown in FIG. 4A, but for example connector block 15 as shown in conjunction with IMD 14 in FIG. 1.

Referring again to FIG. 5B and graph 200B, during the time period prior to time T(0) no power is being delivered to the IMD for recharging, and the temperatures of the front and back exterior surfaces and the connector block of the case IMD, as represented by lines 212, 214, and 216, respectively, approximately correspond to the temperature at internal electronic circuitry as represented by line 210. At time T(0) the recharging of the IMD is initiated, and as shown in graph 200B, the temperatures associated with each of graphical lines 210, 212, 214, and 216 rises at various rates and to various levels over the time period between time T(0) and time T(1), time T(1) represented by vertical dashed line 205 in graph 200B. During the time period between time T(0) and T(1), the temperature at the internal electronic circuitry, as represented by line 210, increases at a more rapid rate compared to the increase in the other temperatures depicted in graph 200B, for example compared to the rate of increase in the temperature of the front exterior surface of the IMD as illustrated by line 212 between time T(0) and T(1). During the recharging of the IMD following time T(1), as illustrated in graph 200B by arrow 205A, the temperature differences between the front exterior surface of the IMD as illustrated by graphical line 212 and the internal electronic circuitry as represented by graphical line 210 substantially stabilizes to an almost steady value.

Once this stabilization of the temperature differences has been reached during a recharging process, for example following a blanking time period (such as the time period between time T(0) and time T(1)), a temperature difference 206 (temperature A) may be defined by one or more transfer functions based on one or more parameters associated with the IMD. These one or more transfer functions may be used to estimate a temperature at the front exterior surface of the IMD, as represented by graphical line 212 in graph 200B, based on a sensed temperature associated with the internal electronic circuitry, as represented by graphical line 210 in graph 200B. The one or more transfer functions may be a function of one or more electrical parameters and/or one or more thermal parameters associated with the IMD and the devices being used to recharge the IMD for the recharging of the rechargeable power source within the IMD. These electrical parameters may include measured parameters such a as battery level percentage (charge level) of a battery of the IMD being recharged, the battery voltage of the battery of the IMD, a charge current ($I_{BATT}$) being provided to the battery of the IMD, a battery power level of the battery of the IMD, a coil resistance of the coil of the IMD that is receiving the inductively induced current used to recharge the battery of the IMD during the recharge process, a power level in the primary coil or tank power ($P_{TANK}$) used to provide the power applied to the IMD for recharging. Thermal parameters associated with the transfer functions may also include a heat loss associated with the IMD ($Q_{IMD}$). The term "battery" as used in this disclosure is not limited to a particular type of power source, and is intended to include any type of power source that may be included within an implantable medical device, including a battery such as a lithium battery, or other electrical device, such as a capacitor or a supercapacitor, that may be configured to store energy and provide an electrical power output that may be used to power electrical circuitry of the implantable medical device and/or to provide power for electrical stimulation therapy provided by the implantable medical device.

In one example, a transfer function that may be used to estimate the temperature of the front exterior surface of an IMD during the recharging of the IMD and during the stability period represented by arrow 205A following a threshold time T(1) based on the sensed temperature at internal electronic circuitry (e.g., as represented by graphical line 210) is provided as:

$$\text{Avg. Front} = \text{Avg. IC} - (C_1 + C_2 * I_{BATT}); \quad \text{(Equation 10)}$$

wherein:
Avg. Front=estimated temperature at the front exterior surface of the IMD;
Avg. IC=average sensed temperature at the internal electronic circuitry of the IMD;
$C_1$=is a first constant value;
$C_2$=a second constant value;
$I_{BATT}$=charging current (in amps) that is applied to the battery or a power source of the IMD that is being recharged.

Equation 10 is an example of an equation that may be used to estimate the temperature at an exterior surface, such as a front exterior surface, of an IMD using an average sensed temperature at the internal electronic circuitry of the IMD, a charging current that is applied to the battery of the IMD, and two constant values. In applying Equation 10, the use of a value for $I_{BATT}$ assumes that the level of current provided as $I_{BATT}$ has not changed for some minimum amount of time, for example for a minimum of 2 minutes, to allow the temperature differential between the exterior surface of the IMD and the internal temperature of the electronic circuitry to stabilize based on the $I_{BATT}$ value. For example, if during the recharging process the power level applied is changed, for example from a "High" power level to a lower power level, and thus causing the $I_{BATT}$ current level to be reduced, the use of Equation 10 should include a "blanking period" following the change in the $I_{BATT}$ current level before Equation 10 is applied to estimate the temperature of the exterior surface of the IMD. Equation 10 is illustrative of equations that may be used to provide such estimated temperatures at the exterior surface of an IMD during times when the IMD is being recharged. Other equations that may include more than two constants and/or higher order equations are possible. Examples of such equations are Equations 11 and 12 further described below.

In various examples, a constant value of −0.340 is used for the value of $C_1$, and a constant value of 0.02265 is used for the value of $C_2$ in Equation 10. The average sensed temperature at the internal electronic circuitry (Avg. IC) may be an average temperature sensed over a predefined time window, such as an average temperature sensed at a sample rate of once every second over a time period of 24 seconds. The average sensed temperature Avg. IC in some examples may be based on a single value for a sensed temperature of the internal electronic circuitry sensed at a given sample time rather than a plurality of sensed temperatures sensed over a predefined time window. Based on the value determined for the Avg. IC, and using a known or measured value for $I_{BATT}$, the transfer function may be used in an algorithm to calculate a value for Avg. Front, and thus provide an estimated temperature for the front exterior surface of the IMD during the portion of the recharge session associated with the Avg. IC sensed temperature. In various examples, over a range of at least 20 to 100 milliamperes (mA) for $I_{BATT}$, use of Equation 10 results in less than a one percent error in estimating the temperature Avg. Front of the front exterior surface of the IMD throughout the stabilized portion of the recharging session.

In another example, a transfer function that may be used to estimate the temperature of the front exterior surface of an IMD during the recharging of the IMD and during the stability period represented by arrow 205A following a threshold time T(1) based on the sensed temperature at internal electronic circuitry, (e.g., as represented by line 210) is provided as:

$$\text{Avg. Front} = \text{Avg. IC} - (C_3 + C_4 * I_{BATT} - C_5 * Q_{IMD}), \quad \text{(Equation 11)}$$

wherein:
Avg. Front=estimated temperature at the front exterior surface of the IMD;
Avg. IC=average sensed temperature at the internal electronic circuitry of the IMD;
$C_3$=is a first constant value;
$C_4$=a second constant value;
$C_5$=is a third constant value;
$I_{BATT}$=charging current (in amps) that is applied to the battery or a power source of the IMD that is being recharged; and
$Q_{IMD}$=heat-loss value (in watts) for the IMD.

In various examples, a constant value of −0.382 is used for the value of $C_3$, a constant value of 0.02936 is used for the value of $C_4$, and a constant value of 0.507 is used for the value of $C_5$ in Equation 11. The average sensed temperature at the internal electronic circuitry (Avg. IC) may be an average temperature sensed over a predefined time window, such as an average temperature sensed at a sample rate of once every second over a time period of 24 seconds. The average sensed temperature Avg. IC in some examples may be based on a single value for a sensed temperature of the internal electronic circuitry sensed at a given sample time rather than a plurality of sensed temperatures sensed over a predefined time window. $Q_{IMD}$ is based on a determined value for heat-loss associated with the IMD as measured in Watts. The total power delivered to the primary (recharging) coil in a recharging system is either lost as heat in the primary coil or inductively transferred to the secondary (receiving coil) of the IMD. Further, the inductively transferred portion is either lost as heat in the IMD or delivered to charge the rechargeable power source of the IMD. In other words, the Recharge Power Delivered=loss in the primary coil+power delivered to the rechargeable power source+loss in the IMD, wherein:

Recharge Power Delivered=$V$primary*$I$primary

Loss in Primary Coil=$I^2$primary*$R$primary

Power Delivered to the Rechargeable Power Source=$V$batt*$I$charge

Loss in the IMD in Watts=$V$primary*$I$primary−$I^2$primary*$R$primary−$V$batt*$I$charge Wherein Vprimary, Iprimary, Rprimary=voltage, current and resistance in the primary coil circuit, and Vbatt, Icharge=voltage and current in the IMD during recharge.

Based on the value determined for the Avg. IC, and using a known or measured value for $I_{BATT}$, the transfer function may be used in an algorithm to calculate a value for Avg. Front, and thus provide an estimated temperature for the front exterior surface of the IMD during the portion of the recharge session associated with the Avg. IC sensed temperature. In various examples, over a range of at least 20 to 100 milliamperes (mA) for $I_{BATT}$, use of Equation 11 results in less than a 0.7 percent error in estimating the temperature Avg. Front of the front exterior surface of the IMD throughout the stabilized portion of the recharging session.

In another example, a transfer function that may be used to estimate the temperature of the front exterior surface of an IMD during the recharging of the IMD and during the stability period represented by arrow 205A following a threshold time T(1) based on the sensed temperature at internal electronic circuitry, (e.g., as represented by line 210) is provided as:

Avg. Front=Avg. $IC-(C_6+C_7*I_{BATT}+C_8*I_{BATT}*I_{BATT})$, (Equation 12)

wherein:
Avg. Front=estimated temperature at the front exterior surface of the IMD;
Avg. IC=average sensed temperature at the internal electronic circuitry of the IMD;
$C_6$=is a first constant value;
$C_7$=a second constant value;
$C_8$=is a third constant value;
$I_{BATT}$=charging current (in amps) that is applied to the battery or a power source of the IMD that is being recharged.

In various examples, a constant value of −0.005 is used for the value of $C_6$, a constant value of 0.00698 is used for the value of $C_7$, and a constant value of 0.000130 is used for the value of $C_8$ in Equation 12. The average sensed temperature at the internal electronic circuitry (Avg. IC) may be an average temperature sensed over a predefined time window, such as an average temperature sensed at a sample rate of once every second over a time period of 24 seconds. The average sensed temperature Avg. IC in some examples may be based on a single value for a sensed temperature of the internal electronic circuitry sensed at a given sample time rather than a plurality of sensed temperatures sensed over a predefined time window. Based on the value determined for the Avg. IC, and using a known or measured value for $I_{BATT}$, the transfer function may be used in an algorithm to calculate a value for Avg. Front, and thus provide an estimated temperature for the front exterior surface of the IMD during the portion of the recharge session associated with the Avg. IC sensed temperature. In various examples, over a range of at least 20 to 100 milliamperes (mA) for $I_{BATT}$, use of equation 10 results in less than a 0.7 percent error in estimating the temperature AVG. Front of the front exterior surface of the IMD throughout the stabilized portion of the recharging session.

Figure 5C:
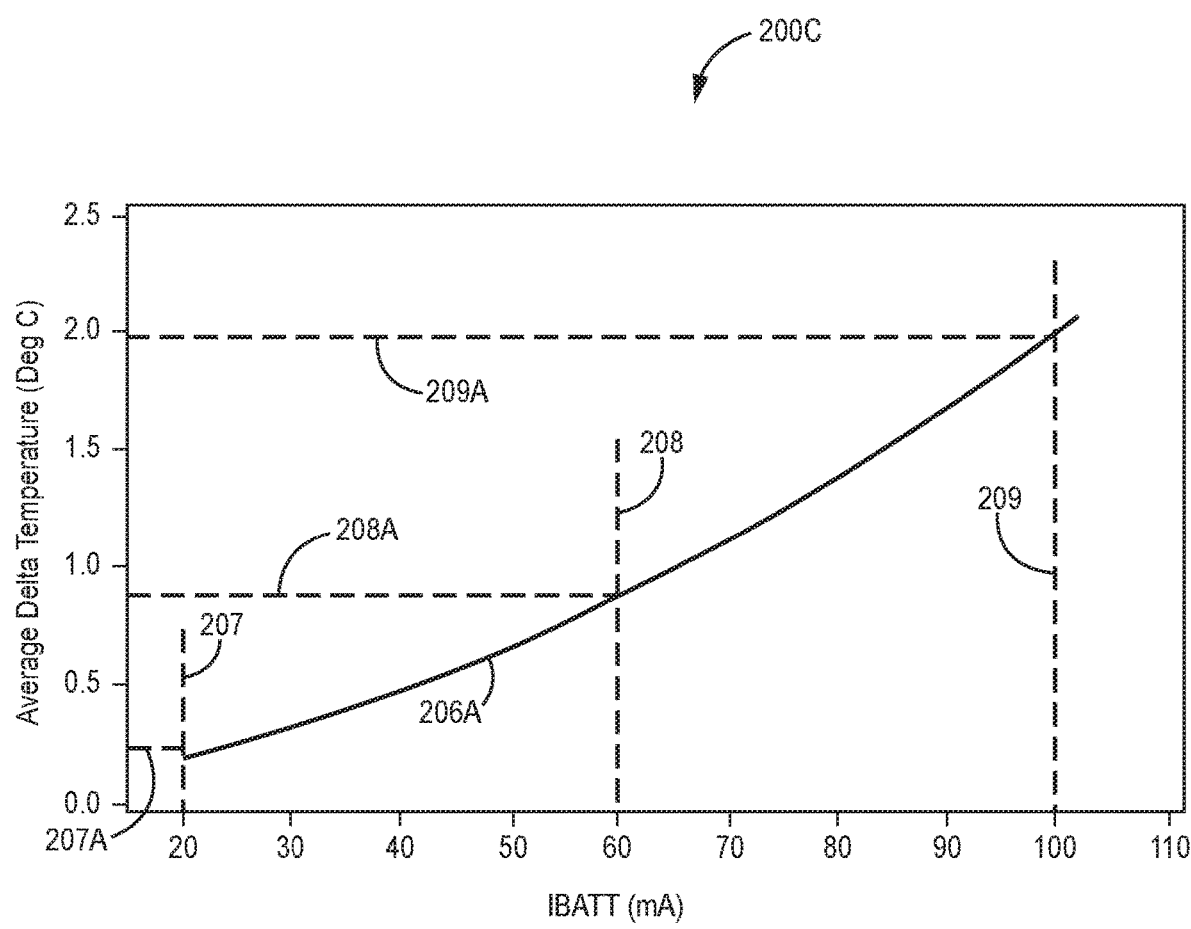
FIG. 5C is a graph of an example transfer function of temperature differentials generated between different portions of an IMD during recharging a rechargeable power source of the IMD in accordance with the techniques described in this disclosure.

FIG. 5C is a graph 200C of temperature differentials generated between different portions of an IMD during recharging a rechargeable power source of the IMD in accordance with various techniques described in this disclosure. These temperature differentials may be used to generate a transfer function characterizing the temperature of the housing as a function of the measured current to the battery, for example. Graph 200C includes a vertical axis representing the average temperature difference (Delta) in degrees Celsius (C) between the exterior front surface of an IMD and the temperature at the internal electronic circuitry of the IMD during a stabilized portion of a recharging process being performed on the IMD, and a horizontal axis representing a battery charging current $I_{BATT}$ in mA. As shown in graph 200C, the transfer function extends over a range of charging currents ranging from 20 mA to 100 mA, as represented by curved line 206A. Curved line 206A is a graphical indication of a fitted line based on one example of measured temperature data that was measured when the $I_{BATT}$ charging current was maintained at approximately a fixed value during the stabilized portion of the recharging session, and using differed fixed values for the $I_{BATT}$ charging current during separate charging sessions. Data collected from twelve sample runs, four runs using an $I_{BATT}$ of 20 mA, four runs using an $I_{BATT}$ of 60 mA, and four runs using and $I_{BATT}$ of 100 mA. Data for one example of the twelve samples runs is summarized in Table 1 as follows:

TABLE 1

Temperature data for various $I_{BATT}$ charging currents

| Run-Order | $I_{BATT}$ (mA) | (x, y, z) | Power (W) | $Q_{IMD}$ (W) | Measured $I_{BATT}$ (mA) | Delta ($T_{IC} - T_{Front}$) | MAX-Temp Front |
|---|---|---|---|---|---|---|---|
| 1 | 20 | 0, 20, 10 | 0.475 | 0.272 | 20 | 0.1752 | 38.188 |
| 2 | 100 | 0, 20, 10 | 1.975 | 1.454 | 99 | 1.795 | 42.75 |
| 3 | 60 | 0, −15, 20 | 1.160 | 0.5585 | 61.8 | 0.9877 | 39.322 |
| 4 | 20 | 0, −15, 20 | 0.490 | 0.189 | 20.7 | 0.2318 | 37.856 |
| 5 | 20 | 0, −15, 20 | 0.490 | 0.189 | 21 | 0.2178 | 37.874 |
| 6 | 100 | 0, 20, 10 | 1.975 | 1.466 | 102.375 | 1.8277 | 42.863 |
| 7 | 60 | 0, 20, 10 | 1.055 | 0.7713 | 59.6 | 0.7721 | 40.248 |
| 8 | 20 | 0, 20, 10 | 0.455 | 0.25348 | 20 | 0.1499 | 37.975 |
| 9 | 60 | 0, −15, 20 | 1.060 | 0.5659 | 61.4 | 0.9948 | 39.383 |
| 10 | 100 | 0, −15, 20 | 2.100 | 1.109599 | 99.75 | 2.1666 | 41.2 |
| 11 | 60 | 0, 20, 10 | 1.055 | 0.7295 | 60.38 | 0.82149 | 40.07 |
| 12 | 100 | 0, −15, 20 | 2.100 | 1.12125 | 100.714 | 2.23867 | 40.894 |

In Table 1, the first column (Run-Order) indicates a sequential number for the test runs, the second column ($I_{BATT}$(mA)) indicates the targeted milliampere level for charging the battery used during the run, the third column ((x,y,z)) indicates one of two possible tilt angles used to position the primary coil used to provide the charging current to the IMD, the fourth column (Power(W)) represents the power provided by the primary coil to the recharging of the IMD, the fifth column ($Q_{IMD}$(W)) represents the estimated heat-loss from the IMD during the recharging session, the sixth column (Measured $I_{BATT}$ (mA)) represents the measured charge current at the battery of the IMD, the seventh column (Delta ($T_{IC}$-$T_{Front}$)) represents the measured temperature difference between the measured temperature sensed by the internal electronic circuitry temperature sensor of the IMD and the measured temperature sensed at the front external surface of the IMD, and the eight column (MAX-temp Front) represents the maximum measured temperature at the front external surface of the IMD for each of the runs. The data was plotted and fitted using regression analysis to develop the curved line 206A, wherein for the regression fit, Delta=0.0052+0.006977 True IBATT+0.000130 True$I_{BATT}$**2; R-Sq=97.1%.

As shown in graph 200C, curved line 206A increased in value with respect to the temperature difference as the charging current $I_{BATT}$ increased over the range from 20 mA to 100 mA. For example, when applying a charging current $I_{BATT}$ of 20 mA to an IMD during the stabilized portion of a charging session of an IMD, a temperature differential in the range of approximately 1.5 to 1.8 degrees C. may exist between the front exterior portion of the IMD and the temperature at the internal electronic circuitry of the IMD. This temperature differential may be graphically illustrated in FIG. 5B and by graph 200B in FIG. 5C by temperature difference 206 between a temperature of the front exterior surface of the IMD as represented by graphical line 212 and the temperature at the internal electronic circuitry of the IMD as represented by line 210 wherein a value of temperature difference 206 is in a range of temperatures surrounding the temperature difference 207A estimated by the transfer function 206A of FIG. 5C.

Referring again to FIG. 5C, when applying a charging current $I_{BATT}$ of 60 mA to an IMD (indicated by vertical dashed line 208), during the stabilized portion of a charging session of an IMD, a temperature differential in the range of approximately 0.7 to 1.0 degrees C. may exist between the front exterior portion of the IMD and the temperature at the internal electronic circuitry of the IMD. This temperature differential may be graphically illustrated in FIG. 5B and by graph 200B in FIG. 5C by temperature difference 206 between a temperature of the front exterior surface of the IMD as represented by line 212 and the temperature at the internal electronic circuitry of the IMD as represented by line 210, but wherein the estimated value of temperature difference 206 is in a range of temperatures surrounding the temperature difference 208A estimated by the transfer function 206A of FIG. 5C.

Referring again to FIG. 5C, when applying a charging current $I_{BATT}$ of 100 mA to an IMD (indicated by vertical dashed line 209), during the stabilized portion of a charging session of an IMD, a temperature differential in the range of approximately 1.8 to 2.2 degrees C. may exist between the front exterior portion of the IMD and the temperature at the internal electronic circuitry of the IMD. This temperature differential may be graphically illustrated in FIG. 5B by graph 200B, and in FIG. 5C by temperature difference 206 between a temperature of the front exterior surface of the IMD as represented by line 212 and the temperature at the internal electronic circuitry of the IMD as represented by line 210. When applying a charge current $I_{BATT}$ of 100 ma, this estimated value of temperature difference may be in a range of temperatures surrounding the temperature 209A estimated by the transfer function 206A of FIG. 5C.

In various examples, the transfer function illustrated in graph 200C of FIG. 5C represents a transfer function derived using each of the transfer functions described above with respect to Equations 10, 11, and 12. In some examples, use of the transfer function provided by Equation 11 and/or 12 may provide an increase in the overall accuracy of the estimated temperature, by reducing the error in the estimated temperature value by a fraction of a percent over use of Equation 10.

Use of Equations 10, 11, or 12 that have at least one parameter related to a charging current, (e.g., $I_{BATT}$), may require a stabilization period, for example a five minute period of time, following initiation of a recharging process before applying these equations to estimate the housing temperature of the device. This stabilization period may be required in order to allow stabilization of the temperature differential between the internal temperature of the device being sensed and a temperature at an exterior surface, e.g., the housing, of the device.

In addition, use of the equations such as Equations 10, 11, or 12 that include at least one instance of a parameter related to a charging current may also require a minimum time to have elapsed during which the value of the charging current has been maintained at a constant level. For example, when using Equations 10, 11, or 12 for the purpose of estimating a temperature of the housing of an implantable medical device, a level of charging current (e.g., $I_{BATT}$ in these equations), should be maintained at a constant level, (such as the 20, 60, or 100 mA levels as depicted in FIG. 5C), for some minimum amount of time before relying on the use of any of these equations for providing a temperature estimation. The minimum amount of time is not limited to any particular amount of time, and may in some examples be in a range of two to three minutes. The minimum amount of time may be a different amount of time for different levels of charging current and/or relative to the direction of a change in a level of charging current being provided as part of a recharging procedure.

For example, changing from a higher level of charging current, (e.g. 100 mA) to a lower level of charging current (e.g., 60 mA) may require a first minimum amount of time for the temperatures of the device to stabilize based on the new level of charging current. Thus, going from a higher level charging current to a lower level charging current may require the first amount of time following the change in the charging current to have elapsed before the equations including use of the value for the charging current could be applied for estimation of the housing temperature of the device. The first amount of time may be a longer period of time compared to changes in current level from higher to lower current levels because the housing temperature may need to cool down as a result of the lower charging current being applied. On the other hand, changing from a lower level of charging current, (e.g. 60 mA) to a higher level of charging current (e.g., 100 mA) may require a second (smaller) minimum amount of time for the temperatures of the device to stabilize based on the new level of charging current. Thus, going from a lower level charging current to a higher level charging current may require the second (smaller) amount of time following the change in the charging current to have elapsed before the equations including use of the value for the charging current could be applied for estimation of the housing temperature of the device. This shorter period of time may be required because the housing temperature may heat up more rapidly due to the increase in the charging current compared to a rate of cool-down for the device when transitioning from the higher level to a lower level charging current.

The transition times, and the relative minimum amount(s) of time to stabilize the temperature differentials when transitioning between different levels of charging currents may be device specific, and may vary from one type and/or model of device to another. In various examples, values for these minimum amounts of time associated with one or more transitions in the levels of charging currents may be stored values that are utilized by the algorithms applied to estimate the housing temperatures. The algorithms used to determine the estimated temperature for a housing of a device using these formulas may be further configured to determine if the requisite minimum amount of time has elapsed for a given charging current or a transition in the level of charging current being applied during a recharging session before applying these formulas to determine the estimated temperature.

Use of these techniques for estimating the housing temperature of a device such as an implantable medical device during a recharging session being performed on the device is not limited to use of just one technique or to use of only one equation or type of equation. For example, at any time following the initial stabilization period for a recharging session, and having the minimum amount of time for stabilization for a particular charging current being applied to the recharging process having elapsed, temperature estimations for the housing temperate of the device may be calculated using one or more of the equations, such as Equations 10, 11, and 12 above, that rely on the sensed internal temperate of the device and the level of charging current being applied. If multiple equations are used, the results of each calculation using the different equations may be compared, and for example must be found to fall within a pre-defined tolerance value for one another as a redundancy check. In some examples, if these determine temperature calculations using the different equations do not correspond, e.g., do not fall with the pre-defined tolerance relative to one another, an alarm output signal may be generated. The alarm output signal that may provide an indication, for example to a technician or a physician, that there may be an issue with the temperature estimation calculation. The alarm output signal may in some examples be used to pause, either temporarily or permanently, the recharging process being performed on the device. The alarm signal in some examples may cause the device or devices performing the recharging process to proceed using a default recharging process that is known to provide a safe level of heat control.

In addition, use of the transfer function based on the decay curve, for example using Equation 1A, may be used in conjunction with and/or as a gap fill for use of the equations based on charging current, such as Equations 10, 11, and 12 described above. For example, the temperature of the housing of a device undergoing a recharging procedure may be estimated using sensed temperatures and based on an algorithm using a transfer function comprising a decay curve of Equation 1A. During the recharging procedure, the recharging power may be interrupted briefly, for example for a period of thirty seconds, and the temperature differentials measured while the charging current is not being applied to the device in order to apply Equation 1A. At times when the charging current is being applied as part of the recharging procedure, and allowing for any minimum stabilization times to have elapsed, any of Equations 10, 11, and/or 12 may be used to estimate a housing temperature for the device. As described above, the temperature or temperature estimated using the decay curve equation may be compared to the temperature or temperatures estimated using the charging current equations (Equations 10, 11, and/or 12), and any discrepancies may be compared to the pre-defined temperature difference threshold as described above. Discrepancies between the calculated temperatures using the different equations that exceed the pre-defined temperature different threshold may generate the alarm output signal having any of the features and configured to provide any of the function as described above.

In addition, the decay curve of Equation 1A may be utilized during times when Equations 10,11, and 12 may not be available for temperature estimations. For example, as described above, when a charging current being applied during a recharging session transitions from one level of current to a different level of current, a minimum amount of time may need to elapse before any of Equations 10, 11, and 12 may be used to estimate the housing temperature. During these times following a transition in charging current and before the minimum amount of time has elapsed, the charging current may be temporarily turned off, for example for a period of thirty seconds, and temperature differentials during that period may be sensed for use in estimating the housing temperature based on Equation 1A. As such, the transfer function may be used at times when the equations such as Equations 10, 11, and 12 that rely on a stabilized level of charging currents are not available for temperature estimates. These examples of use of combinations of equations and techniques for estimating a housing temperature of a device undergoing a charging procedure are intended to be non-limiting examples. Other combinations for using multiple equations for temperature estimation are possible and are contemplated for use in the devices, systems, and methods described in this disclosure. For example, in some examples use of Equation 1A and one or more of Equations 10, 11, and 12 may be utilized simultaneously to estimate a temperature for the housing using each of these equations, and/or an estimate of the temperature of the housing based on for example an average of the temperatures calculated using each of these formulas simultaneously.

FIG. 6 is a layout diagram illustrating a system 230 including a test chamber that may be used to determine one or more constant values associated with thermal properties of an IMD in accordance with the techniques described in this disclosure. System 230 may be used to determine one or more values for constants during manufacturing on some or all devices prior to shipment in some examples. As shown in FIG. 6, a test chamber includes a vessel 231, for example made of clear plastic, that has a hollow interior volume arranged to hold a liquid material 239. In some examples, liquid material 239 comprises a gel/saline solution, a material that has thermal properties designed to simulate the thermal properties of tissue of a human patient.

In system 230, vessel 231 is coupled to an environmental controller 234 through an inlet tube 236 and an outlet tube 237. Environmental controller 234 is arranged to circulate liquid material 239 from the environmental controller through inlet tube 236 into vessel 231, and the draw the liquid material out of vessel 231 back to the environments controller. Environmental controller 234 includes control devices (not shown in FIG. 6) and control circuitry (also not shown in FIG. 6) that allows the environmental controller 234 to monitor the temperature of the liquid material 239, and to regulate the temperature of the liquid material 239 as the liquid material is circulated between the vessel 231 and the environmental controller. In various examples, environmental controller 234 includes control devices that may cool and/or heat the liquid material 239, for example to maintain a constant temperature of the liquid material 239 circulating through vessel 231. In various examples, environmental controller 234 includes one or more temperature sensors, illustratively shown as temperature sensors 238 in FIG. 6. Temperature sensors 238 may be located within environmental controller 234, or in some examples, one or more of the temperature sensors may be located within vessel 231, and coupled, either wirelessly or by a wired connection, to the environmental controller.

In an alternative example, vessel 231 is itself is at least partially submersed in a second vessel 246. Second vessel 246 is filled to a certain level with a liquid 247, such as water, that surrounds at least some portions of vessel 231, and offers a thermal mass that helps maintain the temperature surrounding vessel 231. In examples where second vessel 246 is included, inlet tube 236 and outlet tube 237 may terminate within second vessel 246 without extending to vessel 231. In these instances, environmental controller 234 may be configured to circulate and control a temperature associated with liquid 247 in a manner similar to that described above with respect to liquid material 239. In some examples, some portion of the environmental controller 234 may physically extend into secondary vessel 246 and/or into liquid 247 in order to perform some of the functions ascribed to the environmental controller. For the remainder of the description related to system 230 and FIG. 6, any references to interactions between environmental controller 234 and liquid material 239 may be applicable to liquid 247 in examples of system 230 that include second vessel 246 and liquid 247.

As shown in FIG. 6, vessel 231 may include one or more support structures 232 that are arranged to provide a support for an implantable medical device, such as IMD 233, as shown in FIG. 6. When IMD 233 has been positioned on support structures 232, and vessel 231 includes a level of liquid material 239 that is above and surrounds IMD 233, support structures 232 allow circulation of the liquid material 239 to all sides of IMD 233, at least to some extent, other than the areas of IMD 233 that are in contact with some portion of the support structures 232. When IMD 233 is arranged within vessel 231 and surrounded by liquid material 239, environmental controller is arranged to circulate and/or to control the temperature of the liquid material 239, and to circulate the temperature controlled liquid material throughout the vessel 231. In this manner, environmental controller 234 may be arranged to maintain a constant temperature within the liquid material circulating in vessel 231. The circulation of liquid material through vessel 231 may therefore provide a medium for transfer of any heat generated by IMD 233 to the environmental controller for cooling. In addition, environmental controller 234 may also heat the liquid material 239, if required, to some predefined temperature level. The predefined temperature level may be a typical temperature that would be present in the area of an implanted medical device such as IMD 233 when the IMD is implanted in a patient. As such, vessel 231 and environmental controller may be arranged to simulate the environmental conditions that IMD 233 may experience when implanted in a patient.

Environmental controller 234 may include a user interface 235, such as a touchscreen, that is configured to allow a user to input parameters, such as a set temperature that is to be maintained within vessel 231, or parameters related to a temperature profiles including temperatures that occur within the liquid material 239 over a predefined time schedule, and that the user wants to have system 230 provide to IMD 233.

System 230 as shown in FIG. 6 also includes an external charging device 240, including a primary coil 242 coupled to the external charging device 240, for example through cable 241. In various examples, external charging device 240 is external charging device 22, and primary coil 242 is charging head 26, as illustrated and described with respect to FIG. 1. In various examples, external charging device 240 and primary coil 242 may provide any of the features and perform any of the functions related to recharging and communications with an IMD that were described above for external charging device 22 and/or charging head 26.

For example, external charging device 240 may be configured to provide a charging session of a rechargeable power source (not specifically shown in FIG. 6, but for example rechargeable power source 18 of IMD 14 as shown in FIG. 2), including initiating a charging session with IMD 233, varying the power level and/or modulating the power level(s), being applied to primary coil 242, and terminating the charging session. Using system 230, the distance between the primary charging coil 242 and IMD 233 may also be repeatable and controllable, and thus the system of 230 may be arranged to simulate one or more typical charging arrangements that would typically be encountered when attempting to recharging an implanted IMD.

External charging device 240 may also be configured to wirelessly communicate with IMD 233, for example using wireless link 243, which may include use of any of the communication techniques and/or protocol described throughout this disclosure, and any equivalents thereof. Wireless link 243 may be used by IMD 233 to communicate data related to temperature(s) being sensed by a temperature sensor located within IMD 233. In various examples, the temperature sensor located within IMD 233 is configured to sense a temperature of an internal portion of the IMD, such as an integrated circuit (IC) or a hybrid or printed circuit board located within IMD, and is not directly thermally coupled to a housing or exterior surface(s) of IMD 233, and is not configured to sense a temperature of the housing or of any exterior surfaces of IMD 233. In addition, one or more temperature sensors (not specifically shown in FIG. 6), such as a thermistor or a thermocouple device, may be attached and thermally coupled to the housing of IMD 233 to allow sensing the actual temperature of one or more exterior surfaces of the housing of the IMD during any of the procedures performed on the IMD., including recharging procedures performed by system 230 on the IMD. Information sensed by the sensor(s) may be wirelessly transmitted to the external charging device 240, or coupled to external charging device 240 via a wired connection.

Using the sensed temperature information provided by IMD 233 during a charging session, and by controlling the temperature of the liquid material 239 within vessel 231, and controlling the charging process using external charging device 240 and primary coil 242, one or more of the test procedures as described above related to test chambers may be performed using IMD 233 to obtain the data used to determine the thermal properties of the IMD. These thermal properties may include the data related to the transfer function for the thermal decay of the temperatures associated with the IMD at and following the termination of a charging session, as described above with respect to FIG. 5A. The data related to the transfer function may then be used to determine values for the constants that may be used in the formulas applied as part of the algorithm (e.g., calibration algorithm) that allows determination of the temperature of the housing and/or the external surface(s) of the IMD based on the sensed temperatures provided by the internal temperature sensors located within the IMD.

In some examples, these determined values for the constants, along with the formulas and procedural steps for using the constants and the formulas, may be stored in a memory included within IMD 233. These same determined values for the constants, along with the corresponding formulas, may also be stored in other IMDs of a same type, size, and model as IMD 233, for example by a manufacture of the IMDs, prior to sale and implantation of the IMDs. Using these stored values, each of the IMDs may then access these constant values, the stored formulas, and the associated algorithms for use in determining a temperature of the housing and/or external surface(s) of the IMD during a charging process being performed on the IMD. The determined temperatures may then be used to further control the charging process in order to optimize the process. Optimization of the charging process may include reducing the total time required to recharge the rechargeable power source located within the IMD being charged by controlling the power level(s) applied at various times throughout the charging process, while maintaining a proper temperature level of the IMD with respect to patient comfort and safety throughout the charging session.

Figure 7:
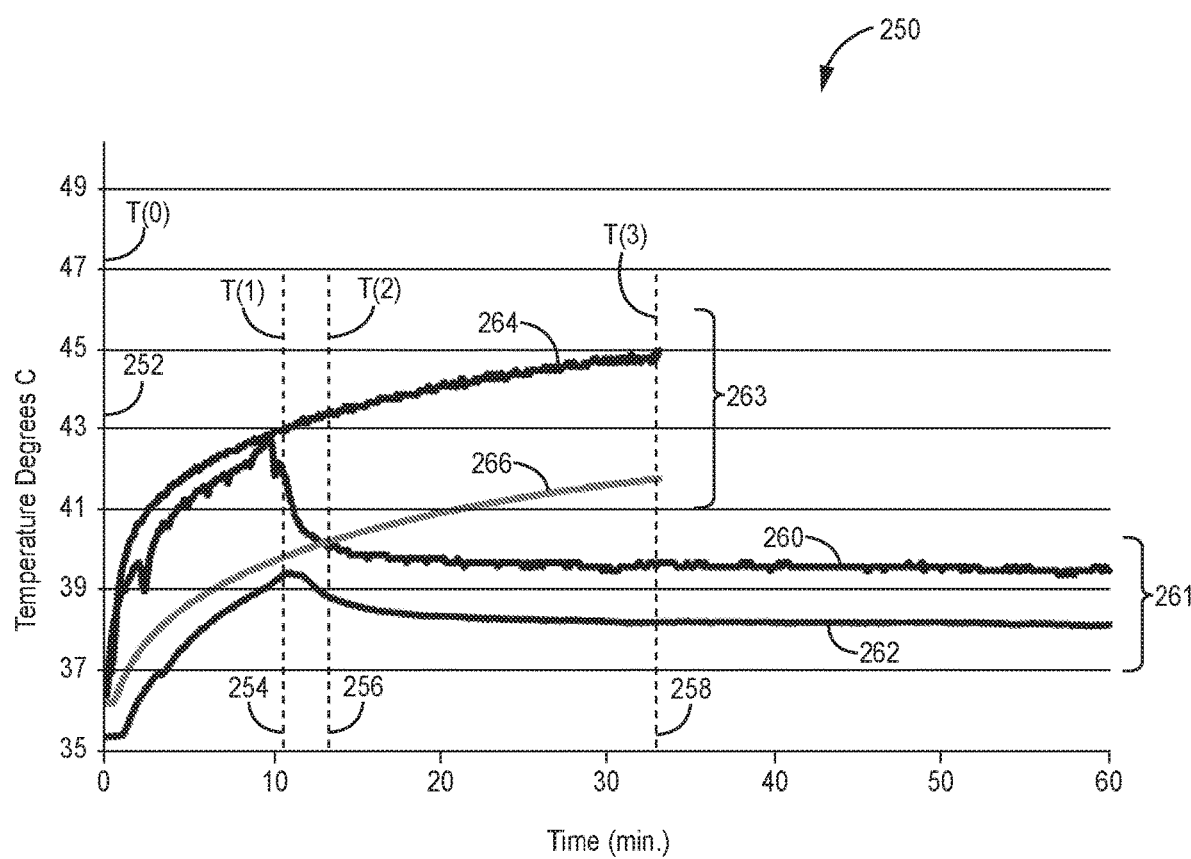
FIG. 7 is a graph of an example comparison of temperatures generated at different portions of an IMD over a period of time using different temperature sensing and estimation techniques to control a recharging process performed on the IMD in accordance with the techniques described in this disclosure.

FIG. 7 is a graph 250 illustrating various examples of temperatures of an implanted medical device during a recharging process in accordance with various techniques. Graph 250 includes a vertical axis representing temperature in degrees Celsius (° C.), and a horizontal axis representing time in minutes. Beginning at time T(0), as represented by vertical line 252 in graph 250, a graph of temperatures 261 associated with a first recharging process that may be performed on an IMD without using the external temperature determination techniques described in this disclosure is illustrated. In addition, a graph of temperatures 263 associated with a second recharging process that utilizes one or more of the external temperature determination techniques described in this disclosure is also included within graph 250. Temperature 264 represents an illustrative temperature curve of sensed temperature values, for example of temperatures sensed within the IMD, and temperature 266 represents an illustrative temperature curve generated, using the constants, algorithm(s), and formula(s) described herein, as determined temperatures at the face of IMD 70 that may occur during the second recharging process, thus allowing a shortened overall recharging period, while still maintain patient safety and comfort during the second recharging process.

In various examples, the second recharging process may be performed on an IMD, such as IMD 70 of FIG. 4A, that includes at least one temperature sensor, such as temperature sensor 80, that is configured to sense a temperature of an internal portion of the IMD, wherein the temperature sensor is not directly thermally coupled to the housing/exterior surface 82 of the IMD, and is not configured to directly or indirectly sense a temperature of the housing/exterior surface 82 of the IMD.

Various temperatures associated with the IMD are illustrated in graph 250 over time relative to the changes in temperature associated with various portions of the IMD throughout each of these two example recharging processes. For comparison purposes, the first charging process and the second charging process may be performed at different times but using a same device, and/or a same model or version of an IMD. For illustrative purposes, the lines representative of temperatures 260 and 262 in graph 250 may be associated with temperatures that occur at various portions of the IMD undergoing the first charging process, which does not utilize the techniques including the algorithms and/or the formulas described in this disclosure. Also shown in graph 250, the lines representative of temperatures 264 and 266 may be associated with temperatures that occur at various portions of the IMD undergoing the second recharging process that does utilize the techniques including the algorithms and/or the formulas describes in this disclosure, for determining a temperature of the housing/exterior surface of the IMD, and for controlling the recharging provided during the second recharging process based the determined temperature of the housing/exterior surface of the IMD.

For example, temperature 260 in graph 250 represents one possible temperature curve illustrative of measured temperatures sensed at an internal electronic circuitry of the IMD, such as electronic circuitry 76, 78, by temperature sensor 80 as illustrated and described with respect to FIG. 4A. Temperature 260 as shown in FIG. 7 represents sensed temperatures when recharging the IMD using a first recharging process that does not utilize the temperature estimation algorithm described above with respect to FIG. 5A. Temperature 262 as shown in FIG. 7 represents a temperature curve of a front face (e.g., housing or exterior surface) of a case of the IMD, for example front face 82 of IMD 70 as illustrated and described with respect to FIG. 4A. Temperature curve 262 corresponds to temperature of the face of the IMD when using the first recharging process that again does not utilize the temperature estimation algorithm or formulas described above with respect to FIG. 5A.

During the first recharging process as illustrated in FIG. 7, sensing a temperature of a component of IMD 70, a processor circuitry of IMD 70, for example, may merely transmit the calculated temperature or data representative of the temperature to a charging device, such as external charging device 22. A processing circuitry of external charging device 22 may then determine how to control the first recharging process. Alternatively, the processing circuitry of IMD 70 may determine how to control the first recharging process, and transmit a respective command to the external charging device. The external charging device may thus charge a rechargeable power source within IMD 70 using one or more power levels, and/or cycle times in some examples. In one example, the charging device may select a "high" power level when first starting a charging session. For example, upon initiation of the first recharging process at time T(0), the external charging device may apply a "high" power level to the primary coil of the charging device. As a result, the sensed temperature at the electronic circuitry of the IMD 70, represented by line 260, rises from an initial value below 37° Celsius to a value of approximately 43° Celsius at time T(1), represented by vertical dashed line 254, approximately 10 minutes into the first recharging process.

Using the sensed temperature, processing circuitry either in the IMD or in the external charging device may compare the sensed temperature 260 to a threshold temperature as part of the first recharging process. The threshold temperature may be selected based on tissue models, patient history, or any other information that may be used to determine when a charging session should be modified. In some examples, because the sensed temperature provided by the electronic circuitry temperature sensor is not thermally coupled to the face of the IMD, the model, and thus the threshold, may be based on a conservative estimate of the temperature of the face of the IMD. For example, a temperature value of 43°

Celsius may be selected as the threshold value for the first recharging process. When a determination has been made, for example with respect to temperature 260 at time T(1), that the sensed temperature has reached the threshold temperature, the first recharging process may be arranged to control the recharging of IMD 70 by adjusting a power level used to charge the rechargeable power source. In other words, the first recharging process may be arranged to reduce the power level when the temperature threshold is reached, turning the power off for a predetermined period of time before the power is again provided (e.g., cycle the power on and off) or even terminate the charging session. Reducing the power level may reduce the energy used to charge IMD 70, and thus lower the temperature of the electronic circuitry within the IMD.

For example, at time T(1) in the first recharging process illustrated in graph 250, the sensed temperature 260 reached the threshold temperature of 43° Celsius, and the first recharging process lowers the power level being applied to the recharging process, for example to the "low" power level as described above. Due to the reduced power level being applied to the first recharging process following time T(1), the sensed temperature of the electronic circuitry of IMD drops to a level between 39° and 41° Celsius, as illustrated by temperature 260 between time T(1) and time T(2), wherein time T(2) is indicated in graph 250 by vertical dashed line 256. Following time T(2) in graph 250, the first recharging process may be arranged to continue the recharging process at the lower power level, or using a combination of low and high power levels, in order to maintain the temperature level of the electronic circuitry of IMD 70, as represented by temperature 260 between 39° and 41° Celsius, throughout the remainder of the first recharging process.

Temperature 262 represents the temperatures of the face (e.g., the exterior surface of the housing) of the IMD throughout the first recharging process. As illustrated in graph 250, temperature 262 has an initial value just over 35° Celsius (C) at the initiation of the first recharging process at time T(0), and raises to a value of approximately 39° C. at time T(1). At time T(1) the power level being applied to the first recharging process is reduced. Temperature 262 initially continues to rise following time T(1), but then falls back to a value of approximately 39° C. at time T(2), and continues to drop following time T(2) to a value below 39° C. for the remainder of the first recharging process. Because the power level used during the first recharging process is reduced following time T(1), for example at ten minutes into the recharging process, the overall time required to complete the first recharging process may be extended. For example, as illustrated in graph 250, the first recharging process continues for a time period of almost sixty minutes.

Termination of the first recharging process may be based on a determination of the charge level of the power source of IMD 70, or based on a calculated thermal dose applied to the patient during the first recharging process. Further, as described above, the temperature 262 of the face of the IMD is maintained at a temperature below some temperature level, for example the 43° C. temperature, throughout the first recharging process. However, in various examples, the actual temperatures that may occur on the face of the IMD that may still be considered safe for the patient may be much higher than any of the temperature levels occurring at the face of the IMD using the first charging process. For example, a temperature level at the face of the of IMD not to exceed 43° C. may be estimated as the limit for a safe temperature that may occur on the face of the IMD. As shown in graph 250, the temperature 262 of the face of the IMD was maintained well below this 43° C. safety level, based for example on the conservative model used to control the power levels applied by the first charging process. These relatively low temperature levels occurring at the face of the IMD during the first charging process provide sub-optimal charging with respect to the possibility of using the higher power level(s) to shorten the overall time required to complete the charging process in order to be assured of maintaining the temperature of the face of the IMD below the established safety level.

In the alternative, the second charging process generating temperatures 263 in graph 250 represents alternative temperature curves 264, 266 that illustrate temperatures that may occur at different portions of the IMD undergoing the second recharging process. As described above, the second recharging process utilizes the algorithm(s) and one or more of the equations described in this disclosure for determining a temperature of the housing/exterior surface of the IMD based on a sensed temperature provided by a temperature sensor within the IMD that is not directly thermally coupled to the housing/exterior surface of the IMD, and that is not configured to sense a temperature of the housing/exterior surface of the IMD. For purposes of illustration, reference again will be made to IMD 70, temperature sensor 80, electronic circuits 76, 78, and front face 82 of IMD 70 as illustrated and described with respect to FIG. 4A.

As shown in FIG. 7, temperature 264 represents an illustrative temperature curve of sensed temperature values, for example of temperatures at electronic circuits 76, 78, provided by temperature sensor 80 during the second recharging process. Temperature 266 represents an illustrative temperature curve generated, using the constants, algorithm(s), and formula(s) described herein, as determined temperatures at the face 82 of IMD 70 that may occur during the second recharging process.

During the second recharging process as illustrated in FIG. 7, processing circuitry of IMD 70 may access values for constants stored in a memory of IMD 70, and apply these constant values to one or more formulas that allows the processing circuitry to calculate an estimated temperature for the face of the IMD (as illustratively shown as temperature 266), based on the sensed temperatures (illustratively shown as temperature 264), being provided by temperature sensor 80. The processing circuitry of IMD 70 may then determine how to control the second recharging process based on the determined temperature 266 of the face 82 of IMD 70, and transmit a respective command or commands to the external charging device. The external charging device may thus charge a rechargeable power source within IMD 70 using one or more power levels, and/or cycle times in some examples, based on these instructions provided by IMD 70. In one example, the charging device may select a "high" power level when first starting the second recharging process. For example, upon initiation of the second recharging process at time T(0), the charging device may apply a "high" power level to the primary coil of the external charging device. As a result, the sensed temperature 264 at the electronic circuits 76, 78 of the IMD 70 rises from an initial value below 37° Celsius to a value of approximately 43° Celsius at time T(1), represented by vertical dashed line 254, approximately 10 minutes into the first recharging process.

Using the sensed temperature 264 to calculate the determined temperature using the constant values, algorithm(s), and/or formula(s) disclosed herein, processing circuitry of IMD 70 determines that the temperature 266 at the face of the IMD 70 is below 41° Celsius at time T(1), which is still below the threshold value of 43° Celsius used as a safe value for surrounding tissue. As such, processing circuitry of IMD 70 may control the second recharging process to continue to provide a "high" level of power to the second recharging process following time T(1). This approach is in contrast to the approach used in the first recharging process, wherein during the first recharging process the overall power level being applied to the first recharging process was lowered following time T(1).

As shown in FIG. 7, temperatures 263 continue to rise following time T(1), as a "high" or at least a higher overall level of power continues to be applied to the second recharging process as compared to the power level applied to the first recharging process following time T(1). As shown in FIG. 7, the sensed temperature 264 being sensed by temperature sensor 80 continues to rise to a temperature of just under 45° Celsius at time T(3), time T(3) represented by vertical dashed line 258. In some examples, at time T(3) the processing circuitry of IMD 70 may terminate the second recharging process for any of the reasons described above with respect to the first recharging process, including terminating the second recharging process based on a determination that the power source within the IMD has been fully recharged.

In some examples, time T(3) represents a time of less than 35 minutes from the start time T(0) of the second recharging process. The corresponding rise in the determined temperature 266 of the face 82 of IMD 70 also rises following time T(1), but only to a temperature approximately halfway between 41 and 43° Celsius. The temperature 266 at the face of IMD 70 had not risen to the 43° Celsius threshold temperature at any time during the second recharging process. In some examples, by maintaining a higher overall level of power applied to the second recharging process between time T(0) and T(3), a same level of charge may be provided to the rechargeable power source of IMD 70 as was provided by the first recharging process illustrated in FIG. 7, but using a much shorter overall time period, and while still maintaining the temperature of the surface 82 of IMD 70 below the threshold temperature of 43° Celsius. Thus, using the second recharging process, including utilizing the constant values, algorithm(s) and formula(s) described herein to determine the surface temperature of an IMD during a charging session of the IMD, the overall time required to perform the charging session may be optimized, e.g., minimized, while still maintaining the required patient comfort and levels of safety. In the case where determined temperature associated with temperature 266 on the face or exterior surfaces of the IMD may be approaching the 43° Celsius threshold, IMD 14 and/or external charging device 22 may control the reduction in charging power at that time to maintain the determined temperature of the face/exterior surfaces below the 43° Celsius threshold, while potentially still maintaining a more efficient and more optimal recharging process.

In various examples, the second recharging process may be customized to each particular patient. For example, each IMD may initially be programmed with a pre-defined threshold temperature level, such as 43° Celsius, that may be used compare the determined surface temperatures of the IMD against the pre-defined threshold value during a charging session for the purpose of regulation the power level(s) being applied to the IMD during the charging session. In various examples, the pre-defined threshold temperature level is programmable, and may be set to a threshold temperature determined for each individual IMD and patient. For example, the value for the pre-defined threshold temperature level may be programmed with a value other than 43° Celsius that is better suited for the particular patient having the implanted IMD. For some patients, and for example depending on the location where the IMD is implanted, a threshold value higher than the 43° Celsius may be programmed into a memory of the IMD implanted in a patient. During a charging session, the processing circuitry of the IMD accesses the stored value for the threshold temperature programmed into the IMD for that particular patient, and controls the charging process based on the determined temperature of the face/exterior surface(s) of the IMD relative to the value set for the pre-defined threshold temperature value.

In other examples, for patient requiring a higher level of comfort and/or based on the implanted location of the IMD, a lower value for the pre-defined threshold temperature level may be program into the implanted IMD, and that lower threshold temperature level used in the control of the charging process for that IMD. In this manner, temperature profiles provided by the second charging process as described above, may be customized to each individual patient. This ability to program the threshold temperature for each individual IMD can be used to modify the threshold temperature setting multiple times over the lifespan of the implanted IMD, for example to adjust to changing patient and/or implant conditions during the time the implant is being utilized by the patient.

Figure 8:
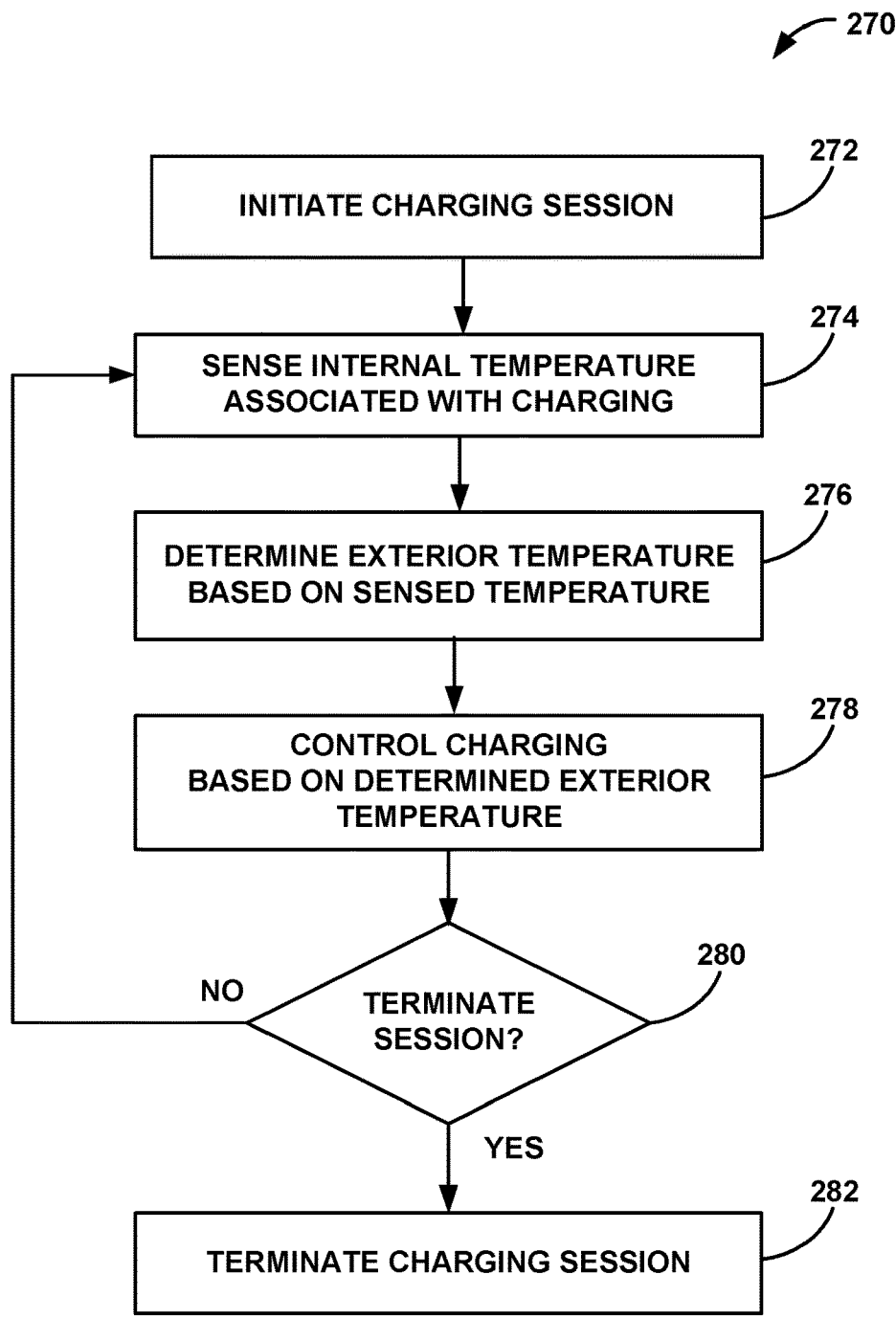
FIG. 8 is a flow diagram that illustrates an example technique for controlling the charging of an implantable rechargeable power source based on a determined housing temperature of an IMD in accordance with the techniques described in this disclosure.

FIG. 8 is a flow diagram 270 that illustrates an example method for charging a rechargeable power source of an IMD in accordance with various techniques described in this disclosure. Processing circuitry 30 of IMD 14 will be described as generally performing the technique of FIG. 8. However, other processing circuitry or devices may contribute to the technique of FIG. 8. For example, the processing circuitry 50 of external charging device 22 may perform one or more of the functions described with respect to the method of FIG. 8.

Processing circuitry 30 may initiate a charging session of a rechargeable power source 18 of IMD 14 in response to receiving a command from a user or other received instructions (block 272). Using a temperature sensor within IMD 14, such as temperature sensor 39 located within IMD 14, processing circuitry 30 may sense the temperature of electronic circuitry housed within IMD 14 associated with the charging session (block 274). The temperature sensor may not be directly thermally coupled to the housing or an exterior surface of IMD 14, and may not be configured to directly sense a temperature of the housing or of the exterior surface of IMD 14. Processing circuitry 30 may then determine (e.g., estimate) an exterior temperature of IMD 14, such as a temperature of exterior surface 19 of IMD 14, based on the sensed temperature provide by the temperature sensor 39 located within IMD 14 (block 276). In various examples, processing circuitry 30 determines the temperature of the exterior surface of IMD 14 using any of the constants, algorithm(s), and/or formula(s) described in this disclosure, or any equivalents thereof. In some cases, processing circuitry 30 may determine multiple temperatures of respective different portions of the exterior of IMD 14 (e.g., connector block, front surface, back surface, side surface) using techniques described herein.

For example, processing circuitry 30 may access a memory, such as memory 32 of IMD 14, to retrieve values for one or more constants previously defined for IMD 14 and that are used in a formula to determine the exterior temperature(s) of one or more portions of IMD 14 based on the sensed temperature(s) of the electronic circuitry or other internal components, such as electronic circuitry, a printed circuit board, and/or a hybrid board included within the housing of IMD 14. The values for these constants may have been determined based on a temperature decay curve corresponding to thermal properties of IMD 14, as described above. In various examples, processing circuitry 30 may apply the values for the determined constants, along with the sensed temperature(s), to determine a current temperature, or a series of determined temperatures, for one or more exterior surface(s) or components of IMD 14, for example using the formula of Equation 1/1A, described above.

Using the determined temperature(s) for the one or more exterior surface(s) 19 or exterior portions of IMD 14, processing circuitry 30 controls the charging session (block 278). Processing circuitry 30 may control the charging session by comparing the determined current temperature of the exterior surface(s) 19 to a threshold value or to respective threshold values, and for example provide instructions for lowering and/or modulating the power level provided to the charging session when the current determined temperature of the exterior surface exceeds a threshold value. Processing circuitry 30 may control the charging session by computing, in one example, a cumulative thermal dose associated with the charging session based on the determined temperature of the exterior surface 19 over some portion of or throughout the entirety of the charging session up to the current time of the charging session. The cumulative thermal dose may be used instead of a temperature threshold to reflect the quantity of heat the tissue has been exposed to. Processing circuitry 30 may control the charging process, for example by providing instructions for lowering and/or modulating the power level provided to the charging session based on the calculated thermal dose. In one example, one portion of the IMD may exceed a respective temperature or cumulative thermal dose threshold before another portion of the IMD exceeds a respective threshold. Processing circuitry 30 may control the charging process based on the first portion of the IMD to exceed a respective threshold in one example.

Processing circuitry 30 may evaluate criteria in order to make a decision to terminate the charging session (block 280). In some examples, processing circuitry 30 uses the determined temperature as a decision criterion for termination of the charging session. For example, processing circuitry 30 compares the determined temperature to a threshold value, and if the determined temperature exceeds a threshold value, processing circuitry may terminate the charging session rather than continue the charging session at some lower or modulated power level. In some examples, processing circuitry 30 compares the thermal dose provided during the charging session to a threshold value, and if the thermal dose exceeds a threshold value, processing circuitry 30 may terminate the charging session. In some examples, processing circuitry 30 may decide to terminate the charging session for other reasons based on criteria not related to the determined temperature. For example, processing circuitry 30 may determine that rechargeable power source 18 is nearly or fully charged, and that further charging is not required. In some examples, processing circuitry 30 may determine that there is some type of error or other malfunction related to the rechargeable power supply 18, and/or other circuitry of IMD 14, which requires the termination of the charging process. In some examples, termination of the charging process may occur when batteries of an external recharger that is powering the primary coil used in the recharging process are depleted.

If processing circuitry 30 determines that the charging session does not need to be terminated, (the "NO" branch at block 280), processing circuitry 30 may continue to sense internal temperatures (block 274), and to determine the exterior temperature to control the charging session (blocks 276, 278). In the alternative, processing circuitry 30 may determine that the charging session should be terminated, (the "YES" branch of block 280), wherein processing circuitry 30 terminates the charging session (block 282). Termination of the charging session in some examples includes processing circuitry 30 transmitting instructions to the external charging device 22 to terminate the charging session, including transmitting instructions to external charging device 22 to remove the power that is being provided by the external charging device for the charging of the rechargeable power source 18.

Figure 9:
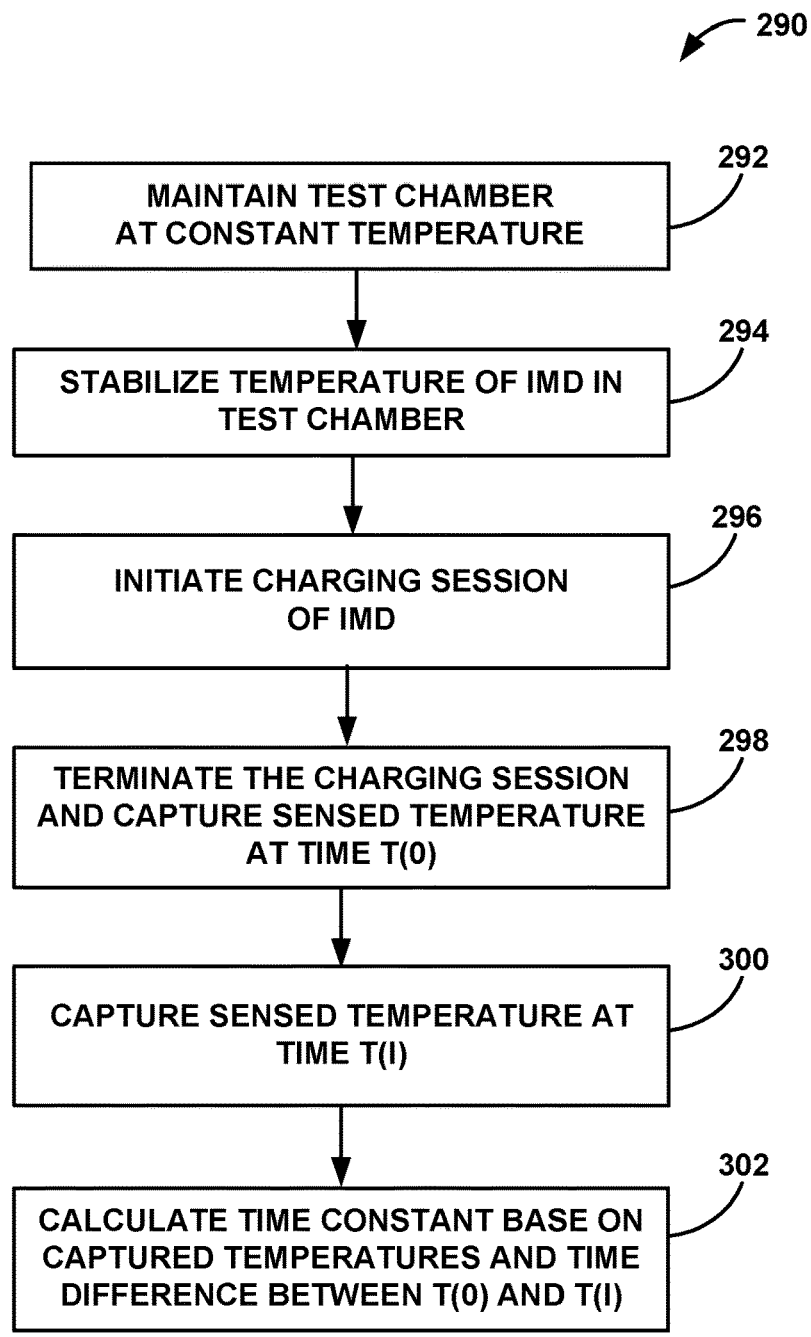
FIG. 9 is a flow diagram that illustrates an example technique for determining values for constants used in an algorithm for determining a housing temperature of an IMD in accordance with the techniques described in this disclosure.

FIG. 9 is a flow diagram that illustrates an example method 290 for determining values for one or more constants that may be applied in formula(s) used to determine the external temperature of an IMD during charging of the IMD in accordance with various techniques described in this disclosure. Instrumentation associated with a test chamber and processing circuitry 30 of IMD 14 will be described as generally performing the technique of FIG. 9. However, other processing circuitry or devices may contribute to the technique of FIG. 9. For example, the processing circuitry, temperature measuring instruments, and/or computer controlled devices included as part of the test chamber system may be used to perform some portion of the method of FIG. 9.

Method 290 includes setting and maintaining a test chamber at a pre-defined constant temperature (block 292). In some examples, the functions of setting and maintaining a test chamber at a pre-defined constant temperature is performed by control circuitry and instrumentation, including temperature sensor(s), that are associated with the test chamber, for example environmental controller 234 and temperature sensor 238 as illustrated and described with respect to FIG. 6. In some examples, the predefined constant temperature is selected to be 37° C.

Referring to FIG. 9, once the predefined constant temperature has been established within the test chamber, method 290 proceeds with stabilizing the temperature of the IMD, such as IMD 14 of FIG. 2, in the test chamber (block 294). In various examples, stabilizing the temperature of the IMD in the test chamber includes placing IMD on support structures within the test chamber so that IMD is surrounded on most exterior surfaces of the IMD by a medium that may transfer heat and maintain a temperature of the exterior surfaces of the IMD, such as liquid medium 239 of system 230 in FIG. 6. In various examples, stabilizing the temperature of the IMD include determining that the temperature of the IMD has stabilized at the predefined constant temperature of the test chamber, and that the internal portions of the IMD are at least stabilized at an internal temperature that does not include any residual heating caused by a previous recharging session, and described above with respect to the test procedures associated with system 230 and FIG. 6.

As shown in FIG. 9, once the temperature of the IMD has been stabilized, e.g., is the same as the constant temperature of the test chamber, and while IMD 14 remains in the test chamber while the test chamber maintains the predefined constant temperature, method 290 proceeds with processing circuitry 30 initiating a charging session the IMD 14 (block 296). In various examples, initiation of a charging session of the IMD includes an external charging device coupled to a primary coil providing electrical energy to the primary coil to induce a charging current in a secondary coil of the IMD for the purpose of initiating the recharging of a power source located within the IMD. In some examples, the external charging device is external charging device 240 and the primary coil is coil 242 of system 230 illustrated and described with respect to FIG. 6.

Referring to FIG. 9, while the recharge session is underway, and when a predefined set of parameters exists with respect to IMD 14, method 290 proceeds by having processing circuitry 30 terminate the recharging session, and capture the sensed temperature provided by a temperature sensor within the IMD, such as temperature sensor 39, at time T(0) (block 298). Time T(0) is indicative of the time the recharging session is terminated. In some examples, the set of parameters used to determine when to terminate the charging session is based on performing the charging session for a period of time that is sufficient to result in a charge current flow to the battery or other power source within the IMD that results in an increase of the temperature at the sensor, but without changing the external temperature of the face of the IMD appreciably. For example, any increase in the temperature of the face of the IMD would be no more than a variation in temperature due to the noise in the temperature measurement.

During this charging process, additional temperature sensors may be located on the exterior surfaces 19 of the IMD in order to confirm that the external temperature of the external surfaces has not increased. In various examples, the sensed temperature is provided by a temperature sensor, such as temperature sensor 39, that is located within IMD 14 and that is not directly thermally coupled to the exterior surface or the housing of IMD 14, and is not configured to directly sense a temperature of the exterior surface or of the housing of IMD 14.

At some time T(1) following termination of the charging session, method 290 proceeds to capture the sensed temperature again that is being provided by the same temperature sensor used to capture the temperature associated with IMD 14 at time T(0) (block 300). Based on the captured temperatures at time T(0) and T(1), and based on the time difference measured between time T(0) and T(1), method 290 includes calculating a time constant based on these sensed temperatures and the calculated time difference (block 302). In various examples, calculating the time constant including calculating a value for the time constant $\tau$, wherein $\tau$ is a time constant having a value of the time required for a temperature difference between the IMD temperature $T_H$ at the internal temperature sensor and the temperature $T_f$ of the front face of the IMD to achieve a value of thirty-seven percent of the initial values for $A_0$ if $T_f$ were held constant, wherein $A_0$ is the temperature difference between $T_H$ and $T_f$ at the time recharge is shut off. Once a value of time constant $\tau$ is determined, method 290 may also calculate a value of $A_0$, for example using Equation 7 described above.

In various examples, method 290 at block 302 further includes storing the values for the constants $\tau$ and $A_0$ into a memory of the IMD for later retrieval during a charging process. The retrieved values may be used during a charging session in one or more formulas, such as Equation 1/1A described above, to calculate a determined temperature for the exterior surface of the IMD based on the sensed temperatures provided by the temperature sensor located within the IMD that is not directly thermally coupled to the exterior surface of the IMD, and is not configured to sense the temperature of the external surface of the IMD.

Figure 10:
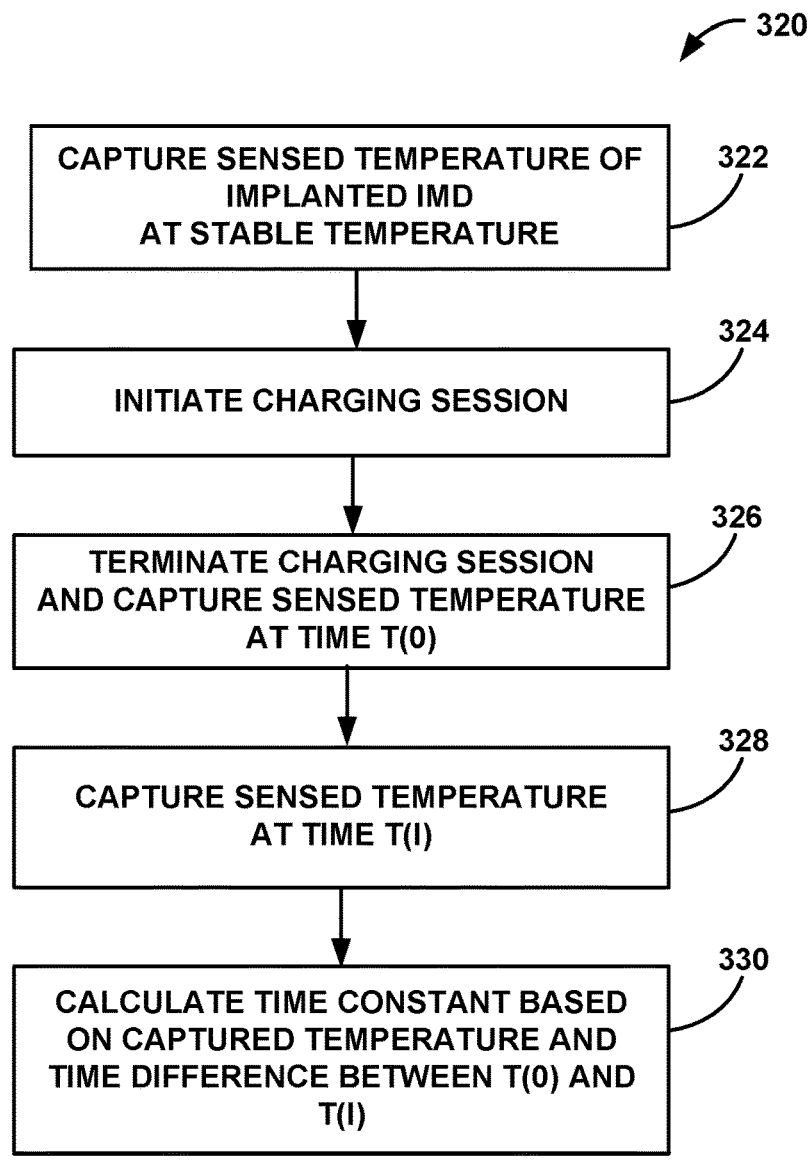
FIG. 10 is a flow diagram that illustrates another example technique for determining values for constants used in an algorithm for determining a housing temperature of an IMD in accordance with the techniques described in this disclosure.

FIG. 10 is a flow diagram that illustrates an example method 320 for determining values for one or more constants that may be applied in formula(s) used to determine the external temperature of an IMD during charging of the IMD in accordance with various techniques described in this disclosure. Processing circuitry 30 of IMD 14 will be described as generally performing the technique of FIG. 10. However, other processing circuitry or devices may contribute to the technique of FIG. 10. For example, the processing circuitry 50 of external charging device 22 as illustrated and described with respect to FIG. 3, may perform one or more of the functions described with respect to the method of FIG. 10.

Method 320 as shown in FIG. 10 may be used to calculate and/or recalculate values for constants used by the algorithm(s) and formula(s) described herein to determine temperature of a housing and/or external surface of an already implanted IMD. As shown in FIG. 10, method 320 includes processing circuitry 30 capturing a sensed temperature of IMD 14 when IMD 14 is at a stable temperature (block 322). A stable temperature may exist when no heating of the IMD 14, residual or otherwise, is present related to a charging session, and the housing and/or external surface of the IMD 14 are at a same temperature as the patient tissue that surrounds and/or contacts the housing or exterior surfaces of the IMD. In addition, any temperatures within IMD 14 are at or have returned to the temperatures that normally exist within the IMD when any and all excess heating of the components due to recharging has dissipated, and for example only normal operating temperatures exist for all portions of the IMD.

After capturing the sensed temperature of the implanted IMD 14 at a stable temperature, method 320 proceeds to initiate a charging session of IMD 14 (block 324). While the charging session is underway, and when a predefined set of parameters exists with respect to IMD 14, method 320 proceeds to terminate the charging session, and to capture the sensed temperature provided by a temperature sensor within the IMD, at time T(0), T(0) being indicative of the time the recharging session is terminated (block 326). In some examples, the set of parameters used to determine when to terminate the charging session is based on performing the charging session for a period of time that is sufficient to result in a charge current flow to the battery or other power source within the IMD that results in an increase of the temperature at the sensor, but without changing the external temperature of the face of the IMD appreciably. For example, any increase in the temperature of the face of the IMD would be no more than a variation in temperature due to the noise in the temperature measurement. The sensed temperature may be provided by a temperature sensor, such as temperature sensor 39, that is located within IMD 14 and that is not directly thermally coupled to the exterior surface or the housing of IMD 14, and is not configured to sense a temperature of the exterior surface or of the housing of IMD 14.

At some time T(1) following termination of the charging session, method 320 proceeds to capture the sensed temperature again that is being provided by the same temperature sensor previously used to capture the temperature associated with IMD 14 at time T(0), (block 328). In various examples, this same temperature sensor may be temperature sensor 39 of IMD 14.

Based on the captured temperatures at time T(0) and T(1), and based on the time difference measured between time T(0) and T(1), method 320 includes calculating a time constant based on these sensed temperatures and the calculated time difference (block 330). In various examples, calculating the time constant including calculating a value for the time constant τ, wherein τ is a time constant having a value of the time required for a temperature difference between the IMD temperature $T_H$ at the internal temperature sensor and the temperature $T_f$ of the front face of the IMD to achieve a value of approximately thirty-seven percent of the initial values for $A_0$ if $T_f$ were held constant, wherein $A_0$ is the temperature difference between $T_H$ and $T_f$ at the time recharge is shut off. The value for τ determined at block 330 may include use of Equation 9 as described above. Once a value of time constant is determined, method 290 may also calculate a value of $A_0$, using for example Equation 7 described above.

In various examples method 320 at block 330 further includes storing the values for the constants τ and $A_0$ into a memory of the IMD for later retrieval during a charging process. The recalculated values may be used in the formulas, such as Equation 1/1A described above, to calculate a determined temperature for the exterior surface of the IMD based on the sensed temperatures provide by the temperature sensor located within the IMD that is not directly thermally coupled to the exterior surface of the IMD, and is not configured to sense the temperature of the external surface of the IMD. Multiple estimates of τ made at different times T(i)>T(0) can be averaged to reduce possible errors due to noise in the measurements.

The ability to calculate and/or to recalculate these constant values following implantation of the IMD may provide several benefits. For example, this process may be run repeatedly across the lifespan of the implant to average repeated estimates of τ for honing the precision of the value assigned to τ for the IMD. Further, changes in τ over the lifetime of the implant may result from a change in the integrity of the IMD. Thus, analysis of the changes and/or trends in the estimated value of τ over time may be used in a warning system or as part of a preventative diagnostic program used to help detect potential issues with the IMD.

According to the techniques and devices described herein, an IMD may include one or more temperature sensors (e.g., a thermistor, a thermocouple, a resistance thermometer, or a silicon bandgap temperature sensor) configured to sense the temperature of a portion of the IMD internal to the IMD where the sensor is not directly thermally coupled to the housing or the exterior surface of the IMD, and is not configured to sense a temperature of the housing or the exterior surface of the IMD. These temperature sensors may be mounted on a PCB or hybrid board within the IMD, or built directly into an integrated circuit or other electronic circuitry located within the IMD, and configured to sense a temperature of the portion of the IMD where the sensor is located. The sensed temperatures provided by the internal sensor may be provided to an algorithm that incorporates one or more formulas and one or more determined constants associated with the thermal properties of the IMD to determine a temperature of the housing and/or exterior surfaces of the IMD. The determined temperatures may then be used to control a charging session in order to minimize the time that a patient needs to spend recharging the IMD, while maintaining temperatures of the IMD and patient tissue in the vicinity of the IMD within the required levels of comfort and safety for the patient.

Various features and advantages of the devices, systems, and techniques of the present disclosure have been described throughout the disclosure. These features and advantages may include any combination of the following capabilities. The ability to determine device surface temperature using a temperature sensor internal to the IMD. This feature in some examples may be further enhanced by establishing a low thermally resistive path between the temperature sensor and the surface of the IMD. The ability to modulate recharge energy during a charging session based on the said absolute/relative temperature measurements. The ability to measure pocket temperature where the IMD is implanted to initiate and guide recharge energy delivery. The ability to detect near-full battery-state and to modulate or stop recharge energy delivery based on this detected state. The ability to detect coupling-quality changes during a charging session based on detection of a sudden/abnormal change in the determined temperature of the external surface of the IMD. For example, a change in the temperature profile based on monitoring a series of determined exterior surface temperatures over time may indicate a change in the coupling conditions during a charging session, (which an accelerometer output can corroborate). The ability to embed multiple temperature sensors within the IMD and to compute temperature of the IMD surface based on their cumulative outputs. The ability to compute temperatures on different surfaces of the IMD based on a single or multiple temperature sensors embedded within the IMD. The ability to detect abnormal/unsafe IMD surface temperature increases in real time due to events such as MRI exposure, Electrosurgery/Cautery, and any other environmental conditions. The ability to determine device constants and calibration constants used in the proposed algorithms described herein during manufacturing of the IMD. The ability to determine calibration constants used in the proposed algorithm while the device is implanted in the patients.

The temperature sensor-based closed loop recharge algorithm as described herein may provide for a safer, more efficient, less burdensome recharge experience for patients. This disclosure aims to provide targeted, consistent solutions for each individual patient by accounting for their temperature tolerance threshold. Further, the devices, systems, and techniques disclosed herein, may also reduce the burden on the physician to instruct the patient to follow certain precautions during recharge, it reduces the burden on the patient to follow these precautions, and it reduces the burden on the medical device manufacturer to supplement their product labeling with these precautions. Moreover, the method of determining temperature of the IMD surface in the recharge-OFF state utilizing the temp-sensor-output decay characteristics offers a method of determining device surface temperature using only the temperature sensor output of a temperature sensor located within the IMD that is not directly thermally coupled to the device surface.

Further, use of the devices, systems, and techniques described in this disclosure are not limited to use in devices, such as implantable or wearable medical devices only during recharging sessions applied to the devices. In some examples, the temperature estimation techniques may be applied to estimating the temperature of the exterior surface of a passive device based on sensed temperatures provided by a temperature sensor located within the passive device that is not thermally coupled to the exterior surface of the device. In some examples, the passive device may not include an internal power source capable of storing electrical energy, and may only operate when energized from an external power source, for example by receiving power from an external device through either being directly coupled to the external device, or through inductively coupled electrical energy provided by the external device. When operating such devices, temperature readings from an internal temperature sensor may be used to estimate a temperature of the external surface of the device. The estimated temperature may be determined using any of the transfer functions and/or equations described throughout this disclosure. The estimated temperature(s) determined during the operation of these passive devices may be utilized for any of the functions and to provide any of the features, such as features and/or functions related to patient safety, as described throughout this disclosure. Use of the one or more of the temperature estimation techniques described herein may be utilized whenever the passive device is being powered to operate in some examples. In other examples, the temperature estimation techniques may only be utilized when the implanted device is being operated in particular modes. For example, certain operations or modes, such as when a heavy load level of data transmission is being performed between the implanted device and external device(s) that require a higher level of power consumption, and thus a potentially higher rise in the temperate levels of the device. In some examples, use of the temperature estimation techniques described herein may be controlled so that they only are utilized for example during the defined higher power level operations to assure that the temperatures of the device does not exceed predefined level related to patient and device safety during the higher power level consuming operations.

For example, when powering a passive device from inductively coupled electrical power provide by an externally powered device, an estimation of the temperature of the housing of the passive device may be made using an algorithm based sensed internal temperatures and a transfer function comprising a decay curve defined by Equation 1A $(T_f(t)=T_H(t)-A_0 e^{-t/\tau})$. In some examples, when powering a passive device from inductively coupled electrical power provide by an externally powered device, an estimation of the temperature of the housing of the passive device may be made using an algorithm based on sensed internal temperatures and a transfer function including use of a measured operating current for the device, such as any of Equation 10 (Avg. Front=Avg. IC$-(C_1+C_2*I_{BATT})$, Equation 11 (Avg. Front=Avg. IC$-(C_3+C_4*I_{BATT}-C_5*Q_{IMD})$, and/or Equation 12(Avg. Front=Avg. IC$-(C_6+C_7*I_{BATT}+C_8*I_{BATT}*I_{BATT})$. When applying any of Equations 10, 11, and/or 12 to estimate the housing temperature of a passive device being powered though inductively coupled power provided by an externally powered device, the "$I_{BATT}$" parameter in these equations represent an operating current level being drawn by the device from the inductively received power.

The disclosure also contemplates non-transitory computer-readable storage media comprising instructions to cause a processor circuitry to perform any of the functions and techniques described herein. The computer-readable storage media may take the form of any volatile, nonvolatile, magnetic, optical, or electrical media, such as a RAM, ROM, NVRAM, EEPROM, flash memory, or any other digital media. The computer-readable storage media may be non-transitory in that the storage media is not an electromagnetic carrier wave. However, this does not mean that the storage media is not transportable or that it is non-volatile. A programmer, such as patient programmer or clinician programmer, may also contain a more portable removable memory type to enable easy data transfer, such as transfer of data related to sensed and/or estimated temperature data for IMDs, or for offline data analysis.

The techniques described in this disclosure, including those attributed to IMD 14, external charging device 22, or various constituent components, may be implemented, at least in part, in hardware, software, firmware or any combination thereof. For example, various aspects of the techniques may be implemented within one or more processors included in processor circuitry, including one or more microprocessors, DSPs, ASICs, FPGAs, or any other equivalent integrated, discrete, or analog logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. While the techniques described herein are primarily described as being performed by processing circuitry 30 of IMD 14, processing circuitry 50 of external charging device 22, or any one or more parts of the techniques described herein may be implemented by a processor of one of IMD 14, external charging device 22, or another computing device, alone or in combination with each other.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

Various examples have been described. These and other examples are within the scope of the following claims.

What is claimed is:

1. A method comprising:
    sensing, by a temperature sensor, a temperature of a first portion of a device during a charging process of a rechargeable power source of the device;
    determining, by processing circuitry and based on the temperature of the first portion of the device and an algorithm, a temperature of a second portion of the device,
        wherein the first portion is not thermally coupled to the second portion of the device, and
        wherein the algorithm is representative of an estimated temperature differential between the first portion and the second portion, the estimated temperature differential determined based on a transfer function, and
        wherein the transfer function is based on an electrical parameter measured from an electrical component associated with the charging process, and
    controlling, by the processing circuitry, the charging process of the rechargeable power source of the device based on the determined temperature of the second portion of the device.

2. The method of claim 1, wherein the device comprises an implantable medical device.

3. The method of claim 1, wherein the temperature sensor comprises one of a thermocouple or a thermistor.

4. The method of claim 1,
    wherein the device comprises an implantable medical device,
    wherein the implantable medical device comprises the temperature sensor, and
    wherein an external charging device comprises the processing circuitry.

5. The method of claim 1,
wherein the first portion comprises an internal portion of the device,
wherein the second portion comprises a housing of the device, and
wherein the internal portion is not thermally coupled to the housing of the external charging device.

6. The method of claim 1,
wherein the first portion comprises a housing of the device,
wherein the second portion comprises an internal portion of the device, and
wherein the internal portion is not thermally coupled to the housing of the external charging device.

7. The method of claim 1, wherein the first portion comprises a first material and the second portion comprises a second material different than the first material.

8. The method of claim 1, wherein the transfer function is based on a temperature decay curve of the second portion of the device.

9. The method of claim 1, wherein controlling the charging process of the rechargeable power source of the device based on the determined temperature of the second portion of the device comprises:
terminating the charging process of the rechargeable power source of the device at a time such that the charging process results in an increase in a first temperature at the first portion of the device without changing a second temperature of the second portion of the device.

10. The method of claim 1, wherein controlling the charging process of the rechargeable power source of the device based on the determined temperature of the second portion of the device comprises:
decreasing a charge rate of the charging process of the rechargeable power source of the device based on the determined temperature of the second portion of the device.

11. The method of claim 1, wherein controlling the charging process of the rechargeable power source of the device based on the determined temperature of the second portion of the device comprises:
increasing a charge rate of the charging process of the rechargeable power source of the device based on the determined temperature of the second portion of the device.

12. The method of claim 1, wherein the electrical parameter is at least one of:
a charging current applied to the rechargeable power source within the device during the charging process;
a battery charge level of the rechargeable power source during the charging process;
a battery voltage of the rechargeable power source during the charging process;
a battery power level of the rechargeable power source during the charging process;
a coil resistance of a charging coil of the device during the charging process; or
a power level of a primary coil applied by a charging device during the charging process.

13. The method of claim 1, wherein the electrical component comprises at least one of:
the rechargeable power source of the device;
a charging coil of the device; or
a primary coil of a charging device.

14. A device comprising:
a first portion;
a second portion not thermally coupled to the first portion of the device;
a rechargeable power source;
a temperature sensor configured to sense a temperature of the first portion during a charging process of the rechargeable power source; and
processing circuitry operably coupled to memory, the processing circuitry configured to:
determine, based on the temperature of the first portion and an algorithm, a temperature of the second portion, wherein the algorithm is representative of an estimated temperature differential between the first portion and the second portion, the estimated temperature differential determined based on a transfer function, and wherein the transfer function is based on an electrical parameter measured from an electrical component associated with the charging process; and
control the charging process of the rechargeable power source based on the determined temperature of the second portion.

15. The device of claim 14, wherein the device comprises an implantable medical device.

16. The device of claim 14, wherein the temperature sensor comprises one of a thermocouple or a thermistor.

17. The device of claim 14,
wherein the first portion comprises an internal portion of the device,
wherein the second portion comprises a housing of the device, and
wherein the internal portion is not thermally coupled to the housing of the external charging device.

18. The device of claim 14,
wherein the first portion comprises a housing of the device,
wherein the second portion comprises an internal portion of the device, and
wherein the internal portion is not thermally coupled to the housing of the external charging device.

19. The device of claim 14, wherein the first portion comprises a first material and the second portion comprises a second material different than the first material.

20. The device of claim 14, wherein the transfer function is based on a temperature decay curve of the second portion of the device.

21. The device of claim 14, wherein to control the charging process of the rechargeable power source of the device based on the determined temperature of the second portion of the device, the processing circuitry is configured to:
terminate the charging process of the rechargeable power source of the device at a time such that the charging process results in an increase in a first temperature at the first portion of the device without changing a second temperature of the second portion of the device.

22. The device of claim 14, wherein the electrical parameter is at least one of:
a charging current applied to a battery within the device during the charging process;
a battery charge level of the rechargeable power source during the charging process;
a battery voltage of the rechargeable power source during the charging process;
a battery power level of the rechargeable power source during the charging process;

a coil resistance of a charging coil of the device during the charging process; or a power level of a primary coil applied by a charging device during the charging process.

23. The device of claim 14, wherein the electrical component comprises at least one of:

the rechargeable power source of the device;

a charging coil of the device; or a primary coil of a charging device.

24. A non-transitory computer-readable medium comprising instructions that, when executed, are configured to cause processing circuitry of a device to:

receive a temperature, sensed by a temperature sensor, of a first portion of the device during a charging process of a rechargeable power source of the device;

determine, based on the temperature of the first portion of the device and an algorithm, a temperature of a second portion of the device, wherein the first portion is not thermally coupled to the second portion of the device, and wherein the algorithm is representative of an estimated temperature differential between the first portion and the second portion, the estimated temperature differential determined based on a transfer function, and wherein the transfer function is based on an electrical parameter measured from an electrical component associated with the charging process, and control the charging process of the rechargeable power source of the device based on the determined temperature of the second portion of the device.

* * * * *